US012807573B2

(12) United States Patent
Hoffmann-Emery et al.

(10) Patent No.: US 12,807,573 B2
(45) Date of Patent: Nov. 24, 2026

(54) PROCESS FOR THE PREPARATION OF BIHETEROARYL COMPOUNDS AND CRYSTAL FORMS THEREOF

(71) Applicants: Genentech, Inc., South San Francisco, CA (US); Hoffmann-La Roche Inc., Little Falls, NJ (US)

(72) Inventors: Fabienne Hoffmann-Emery, Weil am Rhein (DE); Manuel Konrath, Basel (CH); Christian Lautz, uml u+ee llheim (DE); Katrin Monika Niedermann, Bad Ragaz (CH); Ugo Jonathan Orcel, Basel (CH); Diane Elizabeth Carrera, Redwood City, CA (US)

(73) Assignee: Hoffmann La Roche Inc., Branchburg, NJ (US)

( * ) Notice: Subject to any disclaimer, the term of this patent is extended or adjusted under 35 U.S.C. 154(b) by 643 days.

(21) Appl. No.: 18/194,423

(22) Filed: Mar. 31, 2023

(65) Prior Publication Data

US 2023/0312473 A1 Oct. 5, 2023

Related U.S. Application Data

(63) Continuation of application No. PCT/US2021/053005, filed on Sep. 30, 2021.

(60) Provisional application No. 63/087,109, filed on Oct. 2, 2020.

(51) Int. Cl.

| | |
|---|---|
| ***C07D 213/61*** | (2006.01) |
| ***C07D 207/08*** | (2006.01) |
| ***C07D 207/16*** | (2006.01) |
| ***C07D 239/38*** | (2006.01) |
| ***C07D 491/08*** | (2006.01) |

(52) U.S. Cl.

CPC ......... *C07D 213/61* (2013.01); *C07D 207/08* (2013.01); *C07D 207/16* (2013.01); *C07D 239/38* (2013.01); *C07D 491/08* (2013.01); *C07B 2200/13* (2013.01)

(58) Field of Classification Search

None

See application file for complete search history.

(56) References Cited

U.S. PATENT DOCUMENTS

| | | | | |
|---|---|---|---|---|
| 9,266,862 | B2 * | 2/2016 | Estrada | .................. A61P 27/06 |
| 2018/0133219 | A1 | 5/2018 | Estrada et al. | |

FOREIGN PATENT DOCUMENTS

| | | | |
|---|---|---|---|
| WO | 2011/050192 | A1 | 4/2011 |
| WO | 2014/177060 | A1 | 11/2014 |
| WO | 2016/075130 | | 5/2016 |

OTHER PUBLICATIONS

Caira, M.R., Design of Organic Solids "Crystalline Polymorphism of Organic Compounds" Weber, E, Aoyama, Y, et al, eds., Berlin, Heidelberg-Germany:Springer, vol. 198:163-208 (1998).

Rewcastle et al., "Synthesis and Biological Evaluation of Novel Analogues of the Pan Class I Phosphatidylinositol 3-Kinase (PI3K) Inhibitor 2-(Difluoromethyl)-1-[4,6-di(4-morpholinyl)-1,3,5-triazin-2-yl]-1H-benzimidazole (ZSTK474)" J. Med Chem 54(20):7105-7126 (2011).

"International Preliminary Report on Patentability—PCT/US2021/05005" (Report Issuance Date: Mar. 28, 2023; Chapter I), :pp. 1-11 (Apr. 13, 2023).

"International Search Report—PCT/US2021/053005" (w/Written Opinion), :pp. 1-18 (Mar. 15, 2022).

* cited by examiner

*Primary Examiner* — Craig D Ricci

(74) *Attorney, Agent, or Firm* — Robert C. Hall; Genentech, Inc.

(57) ABSTRACT

Processes for preparing biheteroaryl compounds are provided, including the biheteroaryl compound 3-(difluoromethoxy)-5-[2-(3,3-difluoropyrrolidin-1-yl)-6-[(1S,4S)-2-oxa-5-azabicyclo[2.2.1]heptan-5-yl]pyrimidin-4-yl]pyridin-2-amine. Among other advantages, the processes provide for: the use of solvents that are relatively non-toxic and inexpensive; reduced usage of expensive precious metal catalysts; reaction temperature reduction in certain steps; the use of relatively non-toxic oxidation agents; the use of inexpensive transition metal catalysts; a reduction of molar ratios of certain reactants thereby improving process efficiency while reducing cost and waste; significantly higher reactant concentrations in certain steps; elimination of the need for multiple chromatographic purification steps; elimination of the need for certain extraction steps using organic solvent; and provide for higher yield and improved purity.

4 Claims, 2 Drawing Sheets

XRPD Pattern of Crystalline Compound Formula | Form A

PROCESS FOR THE PREPARATION OF BIHETEROARYL COMPOUNDS AND CRYSTAL FORMS THEREOF

CROSS-REFERENCE TO RELATED APPLICATION

This application claims priority to and benefit of U.S. Provisional Patent Application No. 63/087,109, filed Oct. 2, 2020, the content of which is hereby incorporated herein by reference in its entirety.

FIELD OF THE DISCLOSURE

The present disclosure relates to processes for preparing substituted biheteroaryl compounds.

BACKGROUND

Neuron or axon degeneration plays a central role in the proper development of the nervous system and is a hallmark of many neurodegenerative diseases including for example, amyotrophic lateral sclerosis (ALS), glaucoma, Alzheimer's disease, and Parkinson's disease, as well a traumatic injury to the brain and spinal cord. Published United States patent application US 2018/0133219, incorporated herein by reference, describes compound formula

I

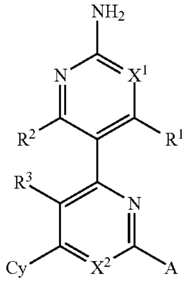

that has been demonstrated to be effective in the treatment of neurodegenerative diseases and nervous system injuries, including for example, through the inhibition of Dual Leucine Zipper Kinase (DLK) in neurons.

General problems associated with known processes for preparing biheteroaryl compounds, especially in large quantities, exist including: toxic and hazardous solvents may be used in some of the process steps; multiple solvent species may be used; high precious metal catalyst loading may be required; relatively high reaction temperatures may be used; toxic and hazardous oxidizing agents may be required; high molar ratios of reactants and reagents may be used in some of the reaction steps; low reactant concentrations may be used in some of the process steps with associated throughput penalties; multiple chromatographic purification steps may be used or required requiring specialized process equipment with associated cost and throughput penalties; solvent extraction steps may be required; solvent stripping steps for isolating intermediates and finished product as solids may be required; and yield may be low.

A need therefore exists for improved processes for preparing compounds of formula I.

BRIEF DESCRIPTION

A first aspect of the present disclosure is directed to a process for preparing a compound of Formula I

I

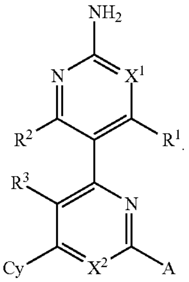

$R^1$, $R^2$ and $R^3$ are each independently selected from the group consisting of H, F, Cl, Br, I, $C_{1-6}$ alkyl and $C_{1-6}$ haloalkyl.

$X^1$ is C—$R^4$, wherein $R^4$ is selected from the group consisting of —F, —Cl, —Br, —I, -$(L^1)_{0-1}$-$C_{1-6}$ alkyl, -$(L^1)_{0-1}$-$C_{1-6}$ haloalkyl, -$(L^1)_{0-1}$-$C_{1-6}$ heteroalkyl, -$(L^2)_{0-1}$-$C_{3-8}$ cycloalkyl, -$(L^2)_{0-1}$-3-7-membered heterocycloalkyl, -$(L^2)_{0-1}$-6-10-membered aryl, and -$(L^2)_{0-1}$-5-10-membered heteroaryl. $L^1$ is selected from the group consisting of —O—, —N(H)—, —S—, —N($C_{1-6}$ alkyl)- and =O. $L^2$ is selected from the group consisting of —O—, —N(H)—, —N($C_{1-6}$ alkyl)-, —S—, =O, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene.

$R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5-membered cycloalkyl, 3-5-membered heterocycloalkyl, $C_{1-6}$ alkoxy, $C_{1-6}$ alkylamino, $C_{1-6}$ dialkylamino, $C_{1-6}$ alkylthio, =O, —$NH_2$, —CN, —$NO_2$ and —$SF_5$.

$R^5$ and $R^6$ are independently selected from straight or branched $C_{1-6}$ alkyl, or $R^5$ and $R^6$ together with the oxygen atoms to which they are attached and the boron atom form 5- to 7-membered heterocyclic ring, wherein the each ring carbon atom may be substituted with 1 or 2 $C_{1-4}$ straight chain alkyl groups.

$X^2$ is N.

A is a 3- to 12-membered N-containing heterocycloalkyl,

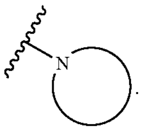 [SMILES: *N]

A is optionally substituted with 1-5 $R^A$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^A)_{0-1}$-3-8-membered cycloalkyl, -$(L^A)_{0-1}$-3-8-membered heterocycloalkyl, -$(L^A)_{0-1}$-5-6-membered heteroaryl, membered heteroaryl, -$(L^A)_{0-1}$-$C_6$ aryl, -$(L^A)_{0-1}$-$NR^{R1a}R^{R1b}$, -$(L^A)_{0-1}$-$OR^{R1a}$, -$(L^A)_{0-1}$-$SR^{R1a}$, -$(L^A)_{0-1}$-N($R^{R1a}$)C(=$Y^1$)$OR^{R1c}$, -$(L^A)_{0-1}$-OC(=O)N($R^{R1a}$)($R^{R1b}$), $(L^A)_{0-1}$-N($R^{R1a}$)C(=O)N($R^{R1a}$)($R^{R1b}$), $(L^A)_{0-1}$-C(=O)N($R^{R1a}$)($R^{R1b}$), $(L^A)_{0-1}$-N($R^{R1a}$)C(=O)$R^{R1b}$, -$(L^A)_{0-1}$-C(=O)$OR^{R1a}$, -$(L^A)_{0-1}$-OC(=O)$R^{R1a}$, -$(L^A)_{0-1}$-P(=O)($OR^{R1a}$)($OR^{R1b}$), -$(L^A)_{0-1}$-$S(O)_{1-2}R^{R1c}$, -$(L^A)_{0-1}$-$S(O)_{1-2}$N($R^{R1a}$)($R^{R1b}$), -$(L^A)_{0-1}$-N($R^{R1a}$)$S(O)_{1-2}$N($R^{R1a}$)($R^{R1b}$) and -$(L^A)_{0-1}$-N($R^{R1a}$)$S(O)_{1-2}$($R^{R1c}$).

$Y^1$ is O or S.

$L^A$ is selected from the group consisting of $C_{1-4}$alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene.

$R^{R1a}$ and $R^{R1b}$ are each independently selected from the group consisting of hydrogen, $C_{1-8}$ alkyl, $C_{1-8}$ haloalkyl, 3-8-membered cycloalkyl, phenyl, benzyl, 5-6-membered heteroaryl and 3-8-membered heterocycloalkyl.

$R^{R1c}$ is selected from the group consisting of $C_{1-8}$ alkyl, $C_{1-8}$ haloalkyl, 3-8-membered cycloalkyl, phenyl, benzyl, 5-6-membered heteroaryl and 3-7-membered heterocycloalkyl, and wherein $R^A$ is optionally substituted on carbon atoms and heteroatoms with $R^{RA}$ substituents selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—S(O)$_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino.

Cy is a 3- to 12-membered N-containing heterocycloalkyl,

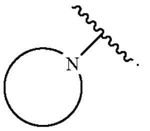 [SMILES: *N]

wherein Cy optionally comprises one or two additional heteroatoms selected from the group consisting of O, S, and N.

Cy is optionally substituted on carbon or heteroatoms with $R^{Cy}$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^{Cy})_{0-1}$-3-8-membered cycloalkyl, -$(L^{Cy})_{0-1}$-3-8-membered heterocycloalkyl, -$(L^{Cy})_{0-1}$-5-6-membered heteroaryl, -$(L^{Cy})_{0-1}$-phenyl, -$(L^{Cy})_{0-1}$-$NR^{RCa}R^{RCb}$, -$(L^{Cy})_{0-1}$-$OR^{RCa}$, -$(L^{Cy})_{0-1}$-$SR^{RCa}$, -$(L^{Cy})_{0-1}$-N($R^{RCa}$)C(=$Y^1$)$OR^{RCc}$, -$(L^{Cy})_{0-1}$-OC(=O)N($R^{RCa}$)($R^{RCb}$), $(L^{Cy})_{0-1}$-N($R^{RCa}$)C(=O)N($R^{RCa}$)($R^{RCb}$), -$(L^{Cy})_{0-1}$-C(=O)N($R^{RCa}$)($R^{RCb}$), -$(L^{Cy})_{0-1}$-N($R^{RCa}$)C(=O)$R^{RCb}$, -$(L^{Cy})_{0-1}$-C(=O)$OR^{RCa}$, -$(L^{Cy})_{0-1}$-OC(=O)$R^{RCa}$, -$(L^{Cy})_{0-1}$-P(=O)($OR^{RCa}$)($OR^{RCb}$), -$(L^{Cy})_{0-1}$-S(O)$_{1-2}R^{RCc}$, -$(L^{Cy})_{0-1}$-S(O)$_{1-2}$N($R^{RCa}$)($R^{RCb}$), -$(L^{Cy})_{0-1}$-N($R^{RCa}$)S(O)$_{1-2}$N($R^{RCa}$)($R^{RCb}$) and -$(L^{Cy})_{0-1}$-N($R^{RCa}$)S(O)$_{1-2}$($R^{RCc}$).

$L^{Cy}$ is selected from the group consisting of $C_{1-4}$alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene.

$R^{RCa}$ and $R^{RCb}$ are each independently selected from the group consisting of hydrogen, $C_{1-8}$ alkyl, $C_{1-8}$ haloalkyl, 3-8-membered cycloalkyl, phenyl, benzyl, 5-6-membered heteroaryl and 3-8-membered heterocycloalkyl.

$R^{RCc}$ is selected from the group consisting of $C_{1-8}$ alkyl, $C_{1-8}$ haloalkyl, 3-8-membered cycloalkyl, phenyl, benzyl, 5-6-membered heteroaryl and 3-7-membered heterocycloalkyl.

$R^{Cy}$ is optionally substituted on carbon atoms and heteroatoms with from 1 to 5 $R^{RCy}$ substituents selected from the group consisting of F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-S(O)$_{0-2}$—, $C_{1-4}$ (halo)alkyl-N(H)S(O)$_{0-2}$—, $C_{1-4}$ (halo)alkyl-S(O)$_{0-2}$N(H)—, (halo)alkyl-N(H)—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$alkylamino and $C_{1-4}$ dialkylamino.

The process comprises displacing the methoxysulfonyl group of compound (v) under basic conditions in a solvent with a 3 to -12-membered amine-containing heterocycloalkyl compound (vi) to provide the compound of Formula (I)

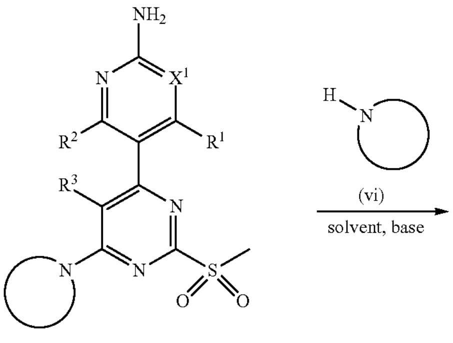

(v)

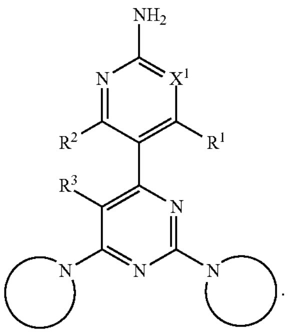

(I)

Said process further comprises preparing compound (v) according to one of schemes (A) to (C).

In scheme (A), sulfone compound (v) is prepared according to the following reaction scheme

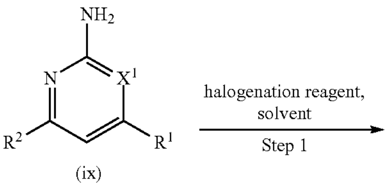

(ix)

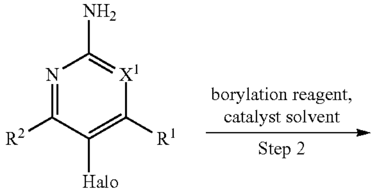

(x)

-continued

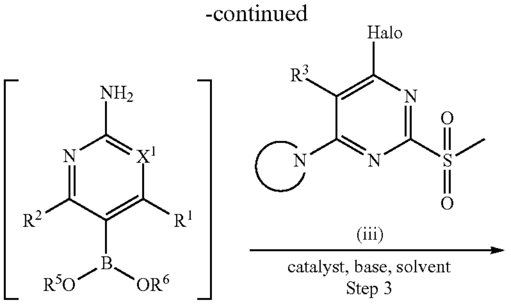

(iii)

(iv)

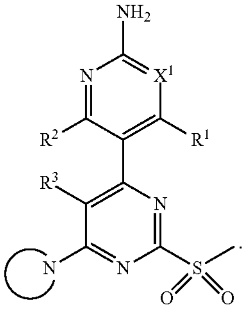

(v)

Scheme (A) comprises: step 1 wherein compound (ix) is combined with a halogenation reagent in a solvent and reacted to form compound (x); step 2 wherein compound (x) is borylated with a borylation reagent to form a solution of compound (iv); and step 3 wherein a solution of compound (iv), compound (iii), a catalyst, a base and a solvent is formed and reacted to form compound (v).

In scheme (B), sulfone compound (v) is prepared according to the following reaction scheme

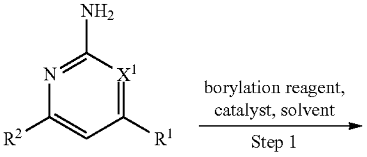

(ix)

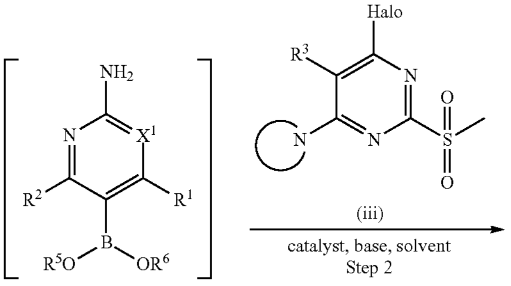

(iii)

(iv)

-continued

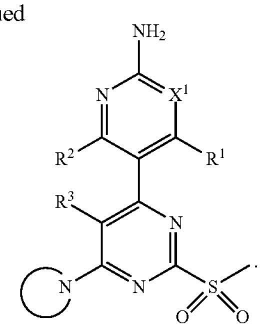

(v)

Scheme (B) comprises: step 1 wherein compound (ix) is directly borylated with a borylation reagent to form a reaction product mixture comprising compound (iv) predominantly in solution; and step 2 wherein the reaction product mixture from step 1 is combined with compound (iii), a catalyst, a base and a solvent, and reacted to form compound (v).

In scheme (C), sulfone compound (v) is prepared according to the following reaction scheme by performing a coupling reaction between a sulfone compound (iii) and a boronate reagent (iv) with a catalyst in the presence of a base and a solvent to provide compound (v)

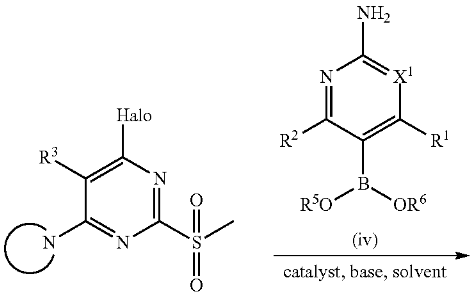

(iii)

(iv)

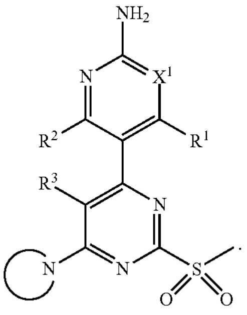

(v)

Scheme (C) further comprises scheme (1), scheme (2), or a combination of scheme (1) and scheme (2).

Scheme (1) comprises preparing sulfone compound (iii) according to the following reaction scheme comprising treating an alkylthio compound (i) with at least one oxidizing agent in a solvent to provide a mixture of oxidized sulfone compound (viii)

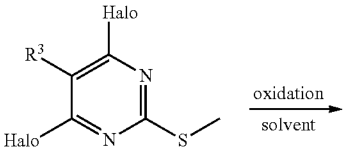

(i)

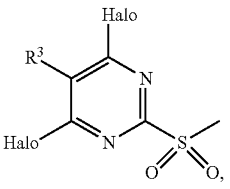
(viii)

displacing a halogen atom from sulfone compound (viii) with an optionally substituted 3- to 12-membered amine-containing heterocycloalkyl compound (vii) under basic conditions in a solvent to form a reaction product mixture comprising sulfone compound (iii)

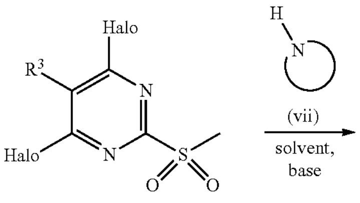

(viii)

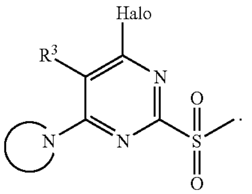
(iii)

Scheme (2) comprises the sulfone compound (iv) species compound (iva) wherein $X^1$ is C—O—$CHF_2$, $R^1$ and $R^2$ are each H, and the moiety —B($OR^5$)($OR^6$) is

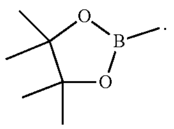

Compound (iva) is prepared according to the following reaction scheme,

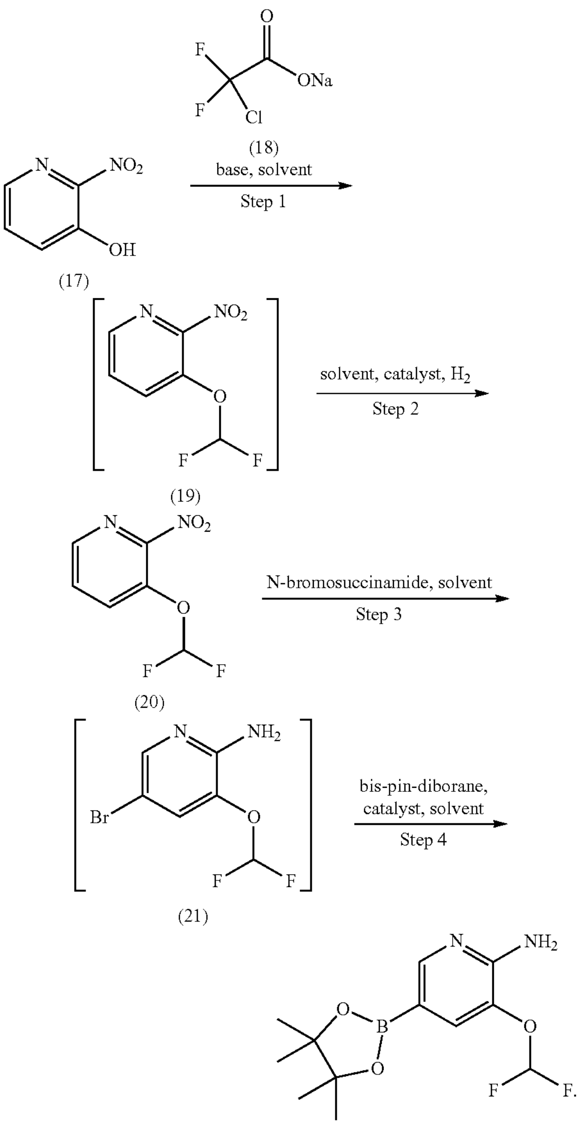

(17) (18) (19) (20) (21)

(iva)

In step 1, a reaction mixture comprising compound (17), compound (18), a solvent and base is formed and reacted to form a reaction product mixture comprising compound (19) predominantly in solution.

In step 2, a reaction mixture comprising the solution of compound (19) is hydrogenated in the presence of catalyst to form a reaction product mixture comprising compound (20).

In step 3, a reaction mixture comprising compound (20), N-bromosuccinimide and a polar aprotic solvent is reacted to form a reaction product mixture comprising compound (21) predominantly in solution.

In step 4, a reaction mixture comprising compound (21) in solution, bis-pin-diborane, and a precious metal catalyst is formed and reacted to form a reaction product mixture comprising compound (iva).

Another aspect of the present disclosure is directed to a process for preparing compound 1. The process comprises the following steps one to four.

In the first step, compound (vii) is reacted with compound (i) in the presence of a solvent and an organic base to form a reaction mixture comprising compound (ii) according to the following scheme

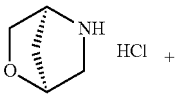

(vii)

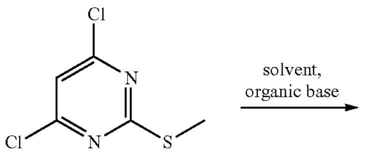

(i)

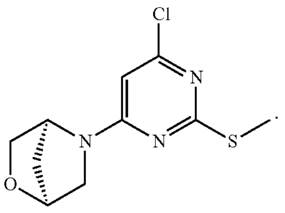

(ii)

The solvent is selected from the group consisting of dimethylsulfoxide, acetonitrile, and ethanol. The equivalents of the organic base to compound (vii) is from about 2.2:1 to about 2.6:1.

In the second step, compound (ii) is oxidized with hydrogen peroxide in the presence of sodium tungstate dihydrate ($Na_2WO_4 \cdot 2H_2O$) to form a reaction product mixture comprising compound (iii) according to the following reaction scheme

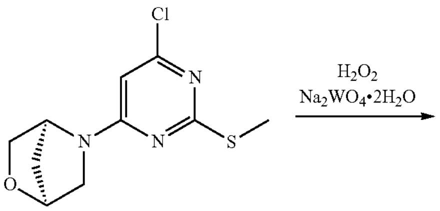

(ii)

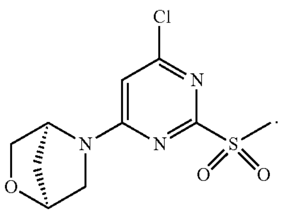

(iii)

The hydrogen peroxide is added to the reaction product mixture from step (1) and the equivalent ratio of hydrogen peroxide to compound (ii) is from about 2:1 to about 3.5:1.

In the third step, a Suzuki coupling of compound (iii) with compound (iva) is performed in the presence of an alkali metal carbonate base, a palladium catalyst, and a solvent to form a reaction product mixture compound (v), then N-acetyl cysteine to the reaction product mixture to scavenge palladium, according to the following scheme

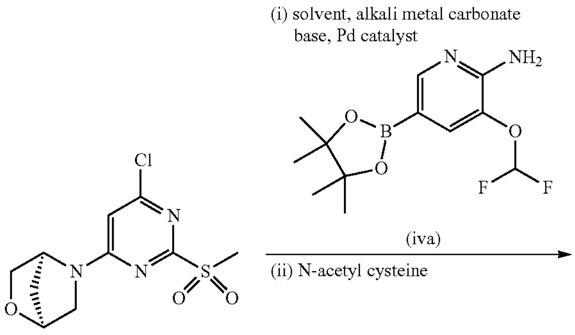

(iva)

(iii)

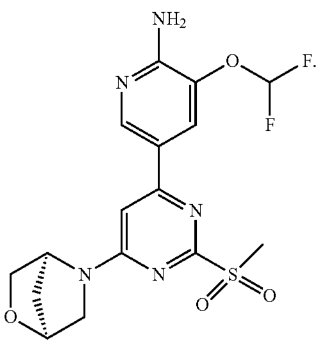

(v)

The solvent is tetrahydrofuran and water, and the palladium catalyst is $PdCl_2$(dppf).

In the fourth step, compound (v) is reacted with compound (vi) in the presence of at least one organic base, and a solvent to form a reaction product mixture comprising compound 1 according to the following reaction scheme

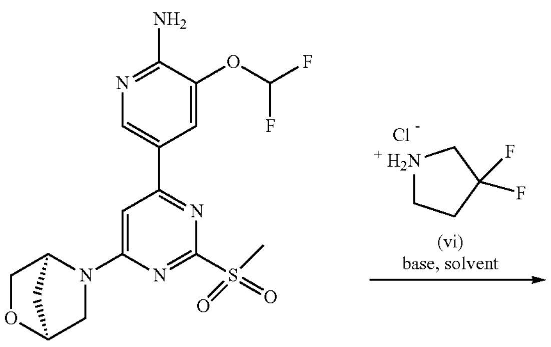

(vi)

(v)

-continued

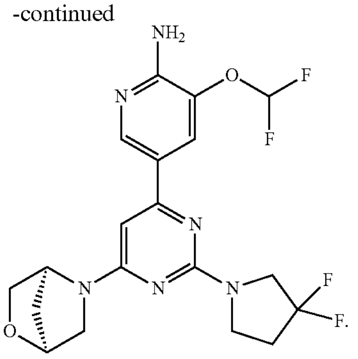

1

The at least one organic base is selected from the group consisting of 1,1,3,3-tetramethylguanidine and 1,8-diazabicyclo[5.4.0]undec-7-ene. The solvent is selected from the group consisting of toluene, anisole, mesitylene, diethylamine, di-n-propylamine, di-isopropylamine, di-n-butylamine, and combinations thereof.

Another aspect of the present disclosure is directed to a process for preparing compound 1. The process comprises the following steps one to six.

In the first step, compound (vii) is reacted with compound (i) in the presence of ethanol and triethylamine to form compound (ii) according to the following reaction scheme

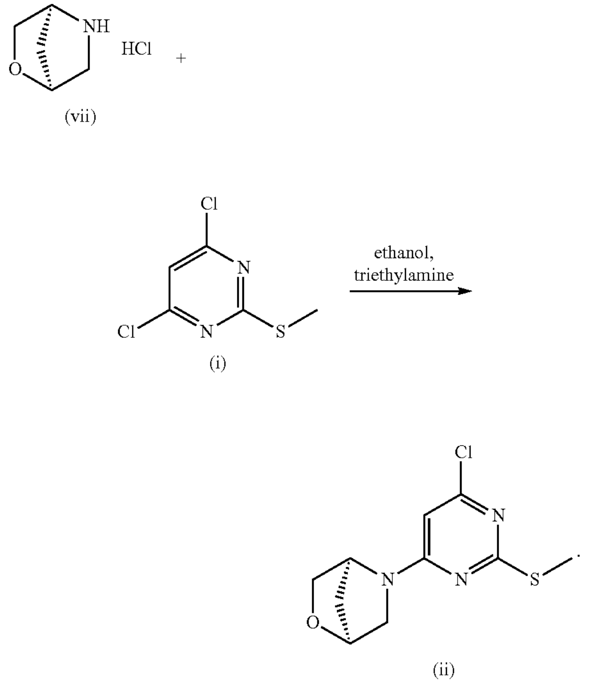

(vii) (i) (ii)

The equivalents of trimethylamine to compound (vii) is about 2.4:1.

In the second step, compound (ii) is oxidized with hydrogen peroxide in the presence of sodium tungstate dihydrate ($Na_2WO_4 \cdot 2H_2O$) to form a reaction product mixture comprising compound (iii) according to the following reaction scheme

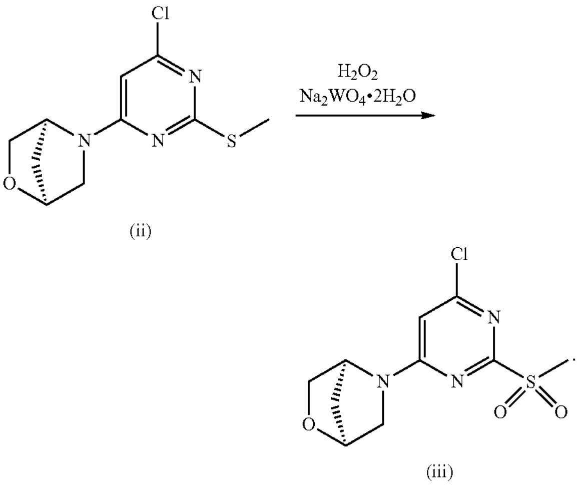

(ii) (iii)

The hydrogen peroxide is added to the reaction product mixture from step (1) and the equivalent ratio of hydrogen peroxide to compound (ii) is about 3:1.

In the third step, (i) a Suzuki coupling of compound (iii) with compound (iva) is done in the presence of $K_2CO_3$ or $Na_2CO_3$, $PdCl_2$(dppf) catalyst, and a tetrahydrofuran and water solvent to form a reaction product mixture compound (v), followed (ii) by adding a N-acetyl cysteine to the reaction product mixture to scavenge palladium, according to the following scheme

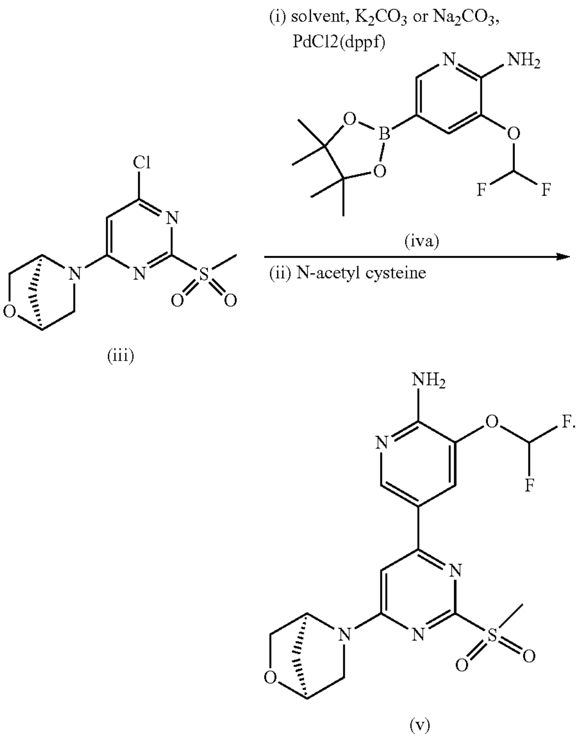

(iii) (iva) (v)

The equivalent ratio of K2CO3 or Na2CO3 to compound (iii) is about 3:1, and the $PdCl_2$(dppf) content is about 0.5 mol % based on compound (iii).

In the fourth step, compound (v) is reacted with compound (vi) in the presence of at least one base, and a solvent to form a reaction product mixture comprising compound 1 according to the following reaction scheme

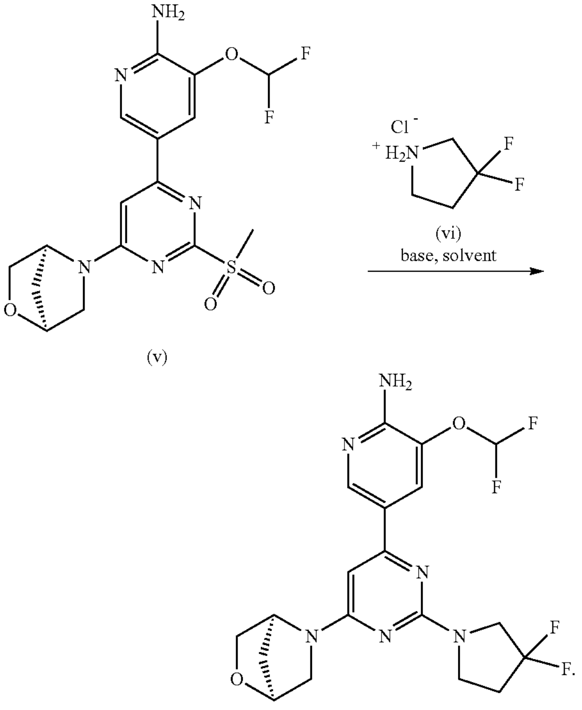

(v)

1

The at least one base is selected from the group consisting of 1,1,3,3-tetramethylguanidine and 1,8-diazabicyclo[5.4.0]undec-7-ene. The solvent is selected from the group consisting of toluene, anisole, mesitylene, diethylamine, di-n-propylamine, di-isopropylamine, di-n-butylamine, and combinations thereof.

In the fifth step, compound 1 is isolated from the step (4) reaction product mixture by the following order of steps: adding an anti-solvent selected from isopropanol and n-propanol to the reaction product mixture; cooling the reaction product mixture to form a slurry comprising solid compound 1; and isolating solid compound 1 from the reaction product mixture.

In the sixth step, a supersaturated solution of compound 1 and methyl isobutyl ketone is formed; the supersaturated solution is seeded with crystalline compound 1 Form A; the solution is cooled to form a slurry comprising crystalline compound 1 Form A; and crystalline compound 1 Form A is isolated from the slurry.

Another aspect of the present disclosure is directed to a compound of formula (iii):

(iii)

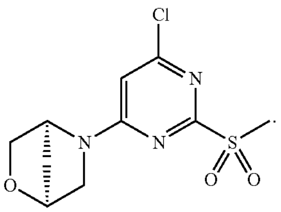

Another aspect of the present disclosure is directed to a crystalline form of compound I

I

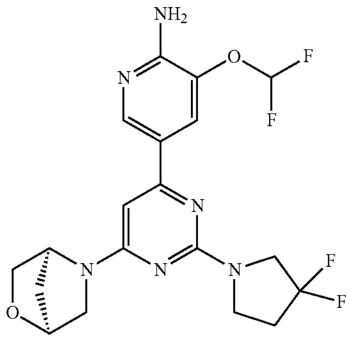

wherein the crystalline form has an X-ray powder diffraction pattern having at least two peaks at positions selected from the group consisting of 7.7±0.3 (°2θ), 12.1±0.3 (°2θ), 16.2±0.3 (°2θ), 16.4±0.3 (°20), 16.6±0.3 (°2θ), 17.1±0.3 (°2θ), 18.8±0.3 (°2θ), 19.4±0.3 (°2θ), 19.8±0.3 (°2θ), 20.3±0.3 (°2θ), 20.5±0.3 (°2θ), 23.3±0.3 (°2θ), 24.7±0.3 (°2θ), 25.3±0.3 (°2θ), and 26.5±0.3 (°2θ).

A further aspect of the present disclosure is directed to a pharmaceutical composition comprising the crystalline form of compound I and at least one excipient.

A further aspect of the present disclosure is directed to a process of preparing the crystalline form of compound I, the process comprising dissolving compound I in a solvent to form a solution, forming a slurry of crystals of compound I therefrom, and isolating crystallized compound I.

A further aspect of the present disclosure is directed to a method of treating a neurodegenerative condition comprising administering an effective amount of the crystalline form of compound I.

DETAILED DESCRIPTION

Figure 1:
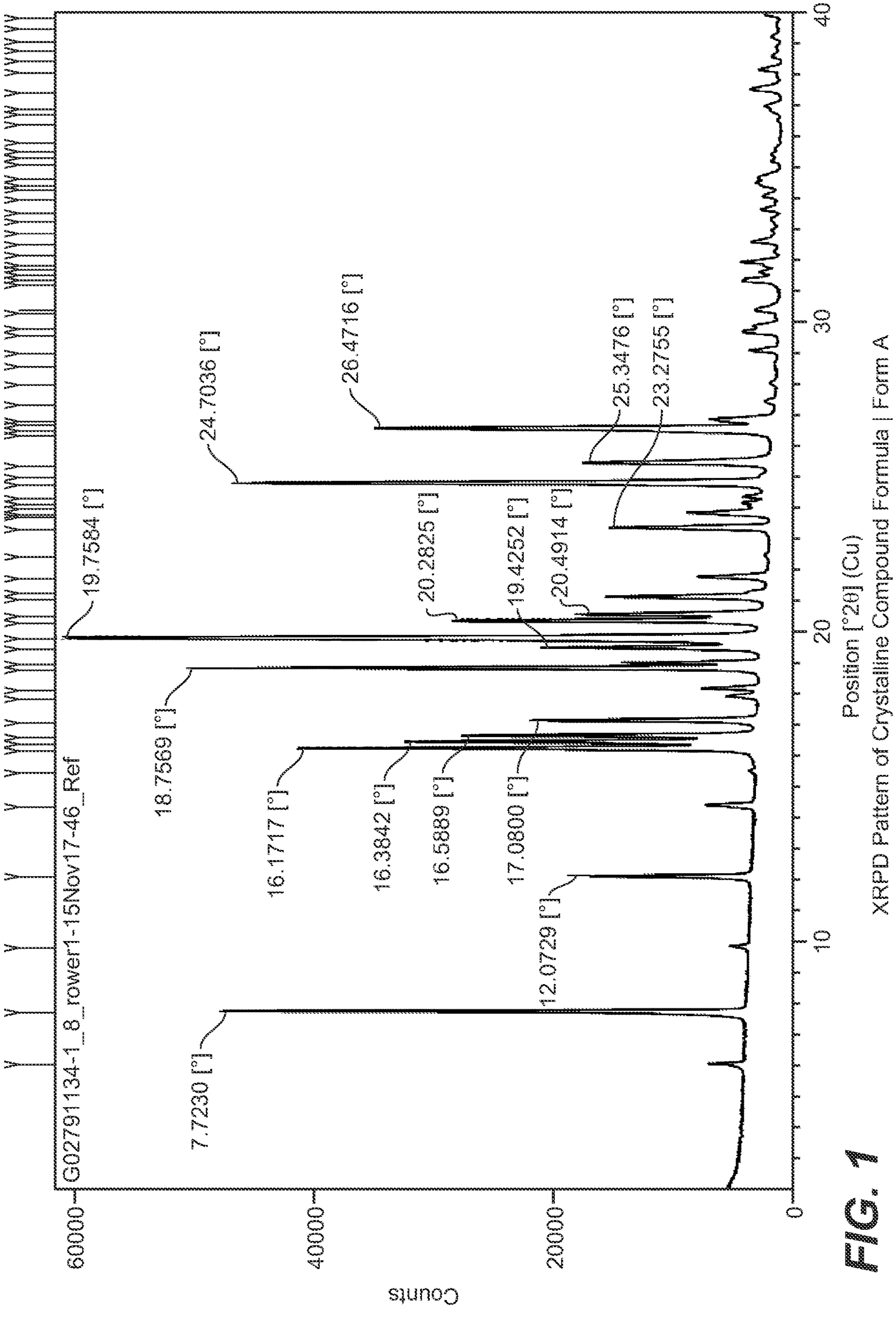
FIG. 1 shows an XRPD pattern of a representative crystalline form of compound 1 identified herein as Form A.

The present disclosure is directed to improved processes for preparing compounds of formula I and associated intermediates.

As compared to prior art processes, the disclosed processes utilize solvents that are relatively non-toxic, are relatively inexpensive, and are relatively benign from the standpoints of industrial hygiene, process safety, and environmental burden. In some aspects, sustainable alcoholic solvents such as methanol and ethanol are used. These aspects therefore provide improved safety and significant cost savings.

The disclosed processes further provide for reduced usage of expensive precious metal catalysts by significant amounts in certain process steps, as compared to prior art processes, thereby providing a significant cost saving.

The disclosed processes still further use relatively non-toxic oxidation agents in combination with inexpensive transition metal catalysts to reduce safety risks and costs.

The disclosed processes yet further allow for a reduction of molar ratios of certain reactants thereby improving process efficiency while reducing cost and waste.

Still yet further, the disclosed processes allow for significantly higher reactant concentrations in certain steps, as compared to prior art processes, thereby resulting in significant improvements in process equipment efficiency and process throughput, and associated cost savings.

Yet further, the disclosed processes eliminate the need for multiple chromatographic purification steps as compared to prior art processes. Chromatographic purification steps require specialized and expensive process equipment, increase the number of required chemical operators, reduce throughput, and increase cost.

The disclosed processes further eliminate the need for certain extraction steps using organic solvent, and eliminate the need for multiple solvent stripping steps. This improvement significantly reduces cost by reducing energy consumption, eliminating solvent handling and distillation steps, consequently obviating the associated needed process equipment and operation thereof, material handling needs, and industrial hygiene and environmental burden risks.

Among the above improvements, the disclosed processes also provide for higher yield and purity as compared to prior art processes.

The discovery of the disclosed processes, as described in detail herein, therefore represents a significant advance in the art.

Additional aspects are within the scope of the present disclosure.

A first such additional aspect is directed to a process of preparing compound I:

I

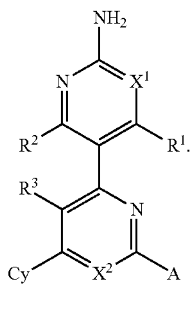

$R^1$, $R^2$ and $R^3$ are each independently selected from the group consisting of H, F, Cl, Br, I, $C_{1-6}$ alkyl and $C_{1-6}$ haloalkyl.

$X^1$ is C—$R^4$, wherein $R^4$ is selected from the group consisting of —F, —Cl, —Br, —I, $-(L^1)_{0-1}-C_{1-6}$ alkyl, $-(L^1)_{0-1}-C_{1-6}$ haloalkyl, $-(L^1)_{0-1}-C_{1-4}$ heteroalkyl, $-(L^2)_{0-1}-C_{3-8}$ cycloalkyl, $-(L^2)_{0-1}$-3-7-membered heterocycloalkyl, $-(L^2)_{0-1}$-6-10-membered aryl, $-(L^2)_{0-1}$-5-10-membered heteroaryl. $L^1$ is selected from the group consisting of —O—, —N(H)—, —S—, —N($C_{1-6}$ alkyl)- and =O. $L^2$ is selected from the group consisting of —O—, —N(H)—, —N($C_{1-6}$ alkyl)-, —S—, =O, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene.

$R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5-membered cycloalkyl, 3-5-membered heterocycloalkyl, $C_{1-6}$ alkoxy, $C_{1-6}$ alkylamino, $C_{1-6}$ dialkylamino, $C_{1-4}$ alkylthio, =O, —$NH_2$, —CN, —$NO_2$ and —$SF_5$.

$X^2$ is N.

A is a 3- to 12-membered N-containing heterocycloalkyl,

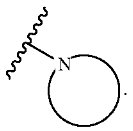 [SMILES: *N]

A is optionally substituted with 1-5 $R^A$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, $-(L^A)_{0-1}$-3-8-membered cycloalkyl, $-(L^A)_{0-1}$-3-8-membered heterocycloalkyl, $-(L^A)_{0-1}$-5-6-membered heteroaryl, $-(L^A)_{0-1}-C_6$ aryl, $-(L^A)_{0-1}-NR^{R1a}R^{R1b}$, $-(L^A)_{0-1}-OR^{R1a}$, $-(L^A)_{0-1}-SR^{R1a}$, $-(L^A)_{0-1}-N(R^{R1a})C(=Y^1)OR^{R1c}$, $-(L^A)_{0-1}-OC(=O)N(R^{R1a})(R^{R1b})$, $-(L^A)_{0-1}-N(R^{R1a})C(=O)N(R^{R1a})(R^{R1b})$, $-(L^A)_{0-1}-C(=O)N(R^{R1a})(R^{R1b})$, $-(L^A)_{0-1}-N(R^{R1a})C(=O)R^{R1b}$, $-(L^A)_{0-1}-C(=O)OR^{R1a}$, $-(L^A)_{0-1}-OC(=O))R^{R1a}$, $-(L^A)_{0-1}-P(=O)(OR^{R1a})(OR^{R1b})$, $-(L^A)_{0-1}-S(O)_{1-2}R^{R1c}$, $-(L^A)_{0-1}-S(O)_{1-2}N(R^{R1a})(R^{R1b})$, $(L^A)_{0-1}-N(R^{R1a})S(O)_{1-2}N(R^{R1a})(R^{R1b})$ and $-(L^A)_{0-1}-N(R^{R1a})S(O)_{1-2}(R^{R1c}$.

$Y^1$ is O or S.

$L^A$ is selected from the group consisting of $C_{1-4}$ alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene.

$R^{R1a}$ and $R^{R1b}$ are each independently selected from the group consisting of hydrogen, $C_{1-8}$ alkyl, $C_{1-8}$ haloalkyl, 3-8-membered cycloalkyl, phenyl, benzyl, 5-6-membered heteroaryl and 3-8-membered heterocycloalkyl.

$R^{R1c}$ is selected from the group consisting of $C_{1-8}$ alkyl, $C_{1-4}$ haloalkyl, 3-8-membered cycloalkyl, phenyl, benzyl, 5-6-membered heteroaryl and 3-7-membered heterocycloalkyl, and wherein $R^A$ is optionally substituted on carbon atoms and heteroatoms with $R^{RA}$ substituents selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-$S(O)_{0-2}$—, $C_{1-4}$ (halo)alkyl-N(H)$S(O)_{0-2}$—, $C_{1-4}$ (halo)alkyl-$S(O)_{0-2}$N(H)—, (halo)alkyl-N(H)—$S(O)_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino.

Cy is a 3- to 12-membered N-containing heterocycloalkyl

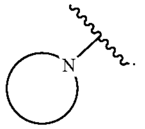 [SMILES: *N]

Cy optionally comprises one or two additional heteroatoms selected from the group consisting of O, S, and N. Cy is optionally substituted on carbon or heteroatoms with $R^{Cy}$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, $-(L^{Cy})_{0-1}$-3-8-membered cycloalkyl, $-(L^{Cy})_{0-1}$-3-8-membered heterocycloalkyl, $-(L^{Cy})_{0-1}$-5-6-membered heteroaryl, $-(L^{Cy})_{0-1}$-phenyl, $-(L^{Cy})_{0-1}-NR^{RCa}R^{RCb}$, $-(L^{Cy})_{0-1}-OR^{RCa}$, $-(L^{Cy})_{0-1}-SR^{RCa}$, $(L^{Cy})_{0-1}-N(R^{RCa})C(=Y^1)OR^{RCc}$, $-(L^{Cy})_{0-1}-OC(=O)N(R^{RCa})(R^{RCb})$, $-L^{Cy})_{0-1}-N(R^{RCa})C(=O)N(R^{RCa})(R^{RCb})$, $-(L^{Cy})_{0-1}-C(=O)N(R^{RCa})(R^{RCb})$, $-(L^{Cy})_{0-1}-N(R^{RCa})C(=O)R^{RCb}$, $-(L^{Cy})_{0-1}-C(=O)OR^{RCa}$, $-(L^{Cy})_{0-1}-OC(=O)R^{RCa}$, $-(L^{Cy})_{0-1}-P(=O)(OR^{RCa})(OR^{RCb})$, $-(L^{Cy})_{0-1}-S(O)_{1-2}R^{RCc}$, $-(L^{Cy})_{0-1}-S(O)_{1-2}N(R^{RCa})(R^{RCb})$, $-(L^{Cy})_{0-1}-N(R^{RCa})S(O)_{1-2}N(R^{RCa})(R^{RCb})$ and $-(L^{Cy})_{0-1}-N(R^{RCa})S(O)_{1-2}(R^{RCc})$.

$L^{Cy}$ is selected from the group consisting of $C_{1-4}$ alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene.

$R^{Ra}$ and $R^{Rb}$ are each independently selected from the group consisting of hydrogen, $C_{1-8}$ alkyl, $C_{1-8}$ haloalkyl, 3-8-membered cycloalkyl, phenyl, benzyl, 5-6-membered heteroaryl and 3-8-membered heterocycloalkyl.

$R^{RCc}$ is selected from the group consisting of $C_{1-8}$ alkyl, $C_{1-8}$ haloalkyl, 3-8-membered cycloalkyl, phenyl, benzyl, 5-6-membered heteroaryl and 3-7-membered heterocycloalkyl.

$R^{Cy}$ is optionally substituted on carbon atoms and heteroatoms with from 1 to 5 $R^{RCy}$ substituents selected from the group consisting of F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-$S(O)_{0-2}$—, $C_{1-4}$ (halo)alkyl-N(H)$S(O)_{0-2}$—, $C_{1-4}$ (halo)alkyl-$S(O)_{0-2}$N(H)—, (halo)alkyl-N(H)—$S(O)_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino.

Said process comprises performing a coupling reaction between a sulfone compound (iii) and a boronate reagent (iv) with a catalyst in the presence of a base and a solvent to provide compound (v) as follows:

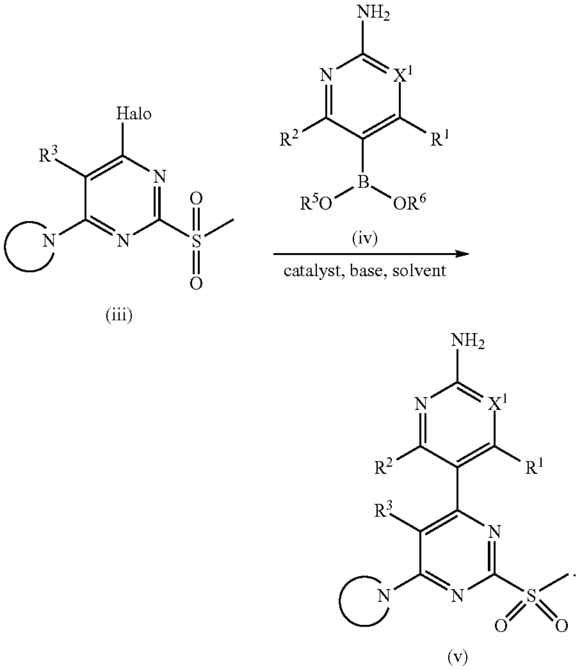

(iii) (iv) (v)

$R^5$ and $R^6$ are independently selected from straight or branched $C_{1-6}$ alkyl, or $R^5$ and $R^6$ together with the oxygen atoms to which they are attached and the boron atom form 5- to 7-membered heterocyclic ring, wherein the each ring carbon atom may be substituted with 1 or 2 $C_{1-4}$ straight chain alkyl groups.

The yield of compound (v), based on compound (iii), is at least 60%.

Said process further comprises displacing the methoxysulfonyl group of compound (v) under basic conditions in a solvent with a 3 to -12-membered amine-containing heterocycloalkyl compound (vi) to provide the compound of Formula (I) as follows:

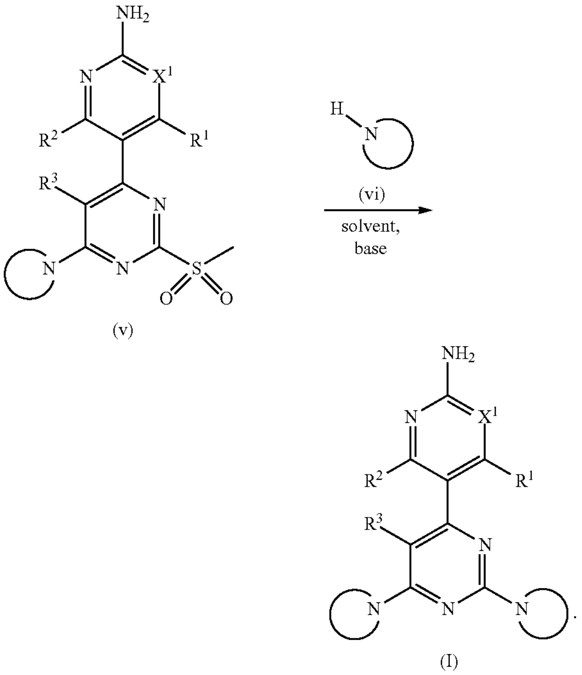

(v) (vi) (I)

The compound of Formula (I) is isolated as a solid. The yield of the compound Formula (I), based on compound (v), is at least 60%.

A second such additional aspect of the present disclosure is directed to compound formula (I) obtained by the process of the first aspect of the disclosure.

A third such additional aspect of the present disclosure is directed to a process for preparing sulfone compound (iii). Said third optional aspect comprises treating an alkylthio compound (i) with at least one oxidizing agent in a solvent to provide an oxidized sulfone compound (viii) as follows:

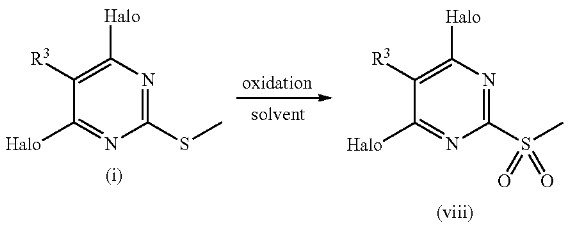

(i) (viii)

and displacing a halogen atom from sulfone compound (viii) with an optionally substituted 3- to 12-membered amine-containing heterocycloalkyl compound (vii) under basic conditions in a solvent to form sulfone compound (iii) as follows:

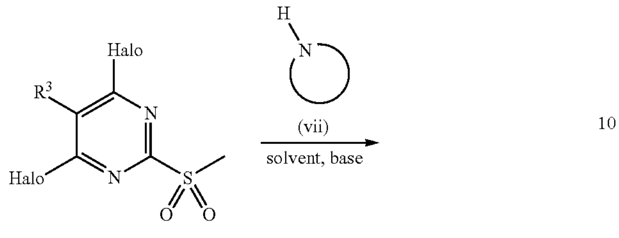

(viii)

(iii)

$R^3$ is selected from the group consisting of H, F, Cl, Br, I, $C_{1-6}$ alkyl and $C_{1-6}$haloalkyl.

A fourth such additional aspect of the present disclosure is directed to the use of the process according to the third aspect of the present disclosure for preparing a compound of formula (Ia):

(Ia)

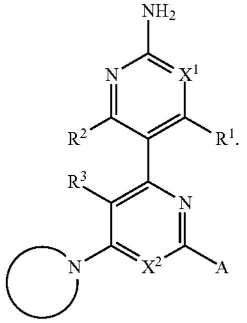

In said fourth aspect, $R^1$, $R^2$ and $R^3$ are each independently selected from the group consisting of H, F, Cl, Br, I, $C_{1-6}$ alkyl and $C_{1-6}$ haloalkyl.

$X^1$ is C—$R^4$, wherein $R^4$ is selected from the group consisting of —F, —Cl, —Br, —I, -$(L^1)_{0-1}$-$C_{1-6}$ alkyl, -$(L^1)_{0-1}$-$C_{1-6}$ haloalkyl, -$(L^1)_{0-1}$-$C_{1-6}$ heteroalkyl, -$(L^2)_{0-1}$-$C_{3-8}$ cycloalkyl, -$(L^2)_{0-1}$-3-7-membered heterocycloalkyl, -$(L^2)_{0-1}$-6-10-membered aryl, -$(L^2)_{0-1}$-5-10-membered heteroaryl.

$X^2$ is N.

$L^1$ is selected from the group consisting of —O—, —N(H)—, —S—, —N($C_{1-6}$ alkyl)- and =O.

$L^2$ is selected from the group consisting of —O—, —N(H)—, —N($C_{1-6}$ alkyl)-, —S—, =O, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene.

$R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5-membered cycloalkyl, 3-5-membered heterocycloalkyl, $C_{1-6}$ alkoxy, $C_{1-6}$ alkylamino, $C_{1-6}$ dialkylamino, $C_{1-6}$alkylthio, =O, —$NH_2$, —CN, —$NO_2$ and —$SF_5$.

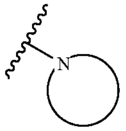

is an optionally substituted 3- to 12-membered N-containing heterocycloalkyl.

A is an optionally substituted 3- to 12-membered N-containing heterocycloalkyl,

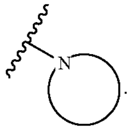

A fifth such additional aspect of the present disclosure is directed to a process for preparing boronate compound (iva) according to the following reaction scheme:

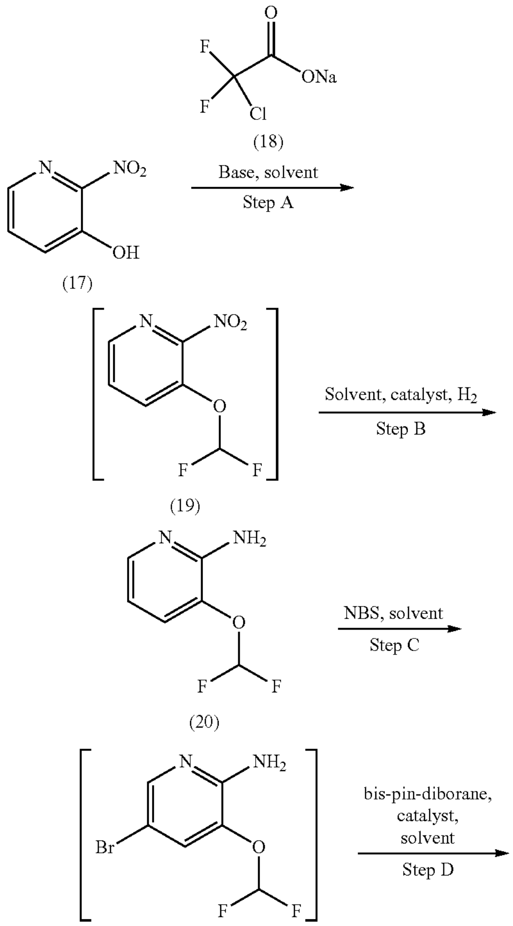

(18)

(17)

(19)

(20)

(21)

-continued

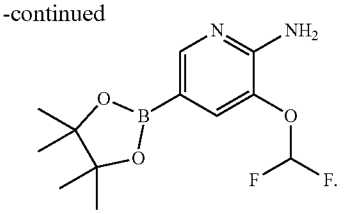

(iva)

The process of said fifth aspect comprises steps A to D.

Step A wherein a reaction mixture comprising compound (17), compound (18), a solvent and base is formed and reacted to form a reaction product mixture comprising compound (19) predominantly in solution.

Step B wherein a reaction mixture comprising the solution of compound (19) is hydrogenated in the presence of catalyst to form a reaction product mixture comprising compound (20).

Step C wherein a reaction mixture comprising compound (20), N-bromosuccinimide and a polar aprotic solvent is reacted to form a reaction product mixture comprising compound (21) predominantly in solution.

Step D wherein a reaction mixture comprising compound (21) in solution, bis-pin-diborane, a precious metal catalyst is formed and reacted to form a reaction product mixture comprising compound (iva).

A sixth such additional aspect of the present disclosure is directed to the use of the process according to the fifth aspect of the present disclosure for preparing a compound of formula (Ib)

(Ib)

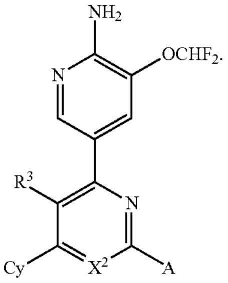

In said sixth aspect, $R^3$ is selected from the group consisting of H, F, Cl, Br, I, $C_{1-6}$ alkyl and $C_{1-6}$ haloalkyl.

$X^2$ is N.

Cy and A are each independently an optionally substituted 3- to 12-membered N-containing heterocycl,

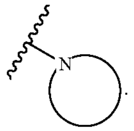

A seventh such additional aspect of the present disclosure is directed to a process for preparing sulfone compound (v) according to the following reaction scheme:

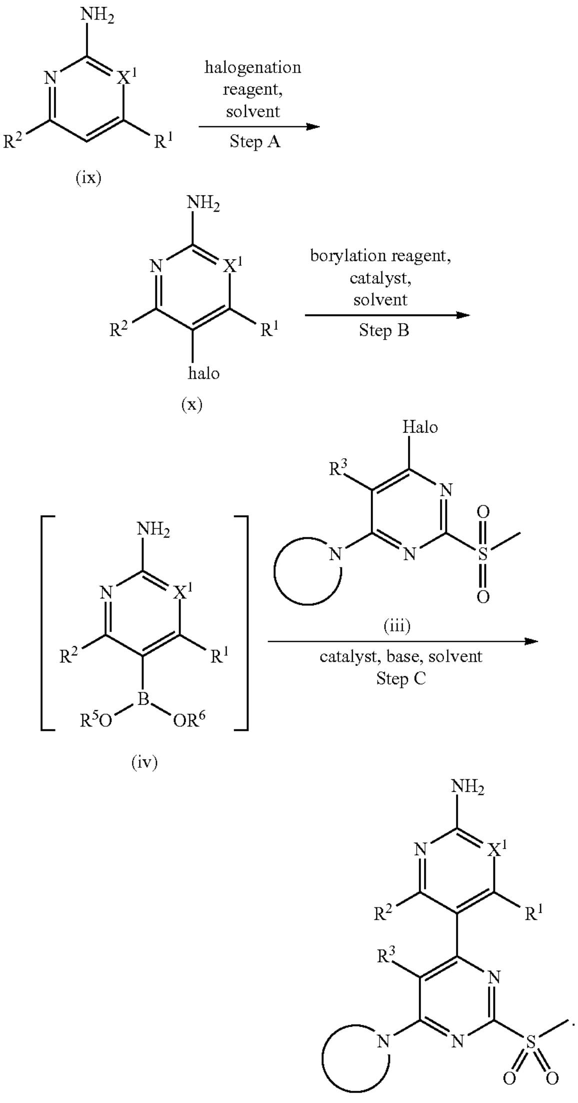

(ix) (x) (iii) (iv) (v)

In said seventh aspect, $R^1$, $R^2$ and $R^3$ are each independently selected from the group consisting of H, F, Cl, Br, I, $C_{1-6}$ alkyl and $C_{1-6}$ haloalkyl.

$X^1$ is C—$R^4$, wherein $R^4$ is selected from the group consisting of —F, —Cl, —Br, —I, -$(L^1)_{0-1}$-$C_{1-6}$ alkyl, -$(L^1)_{0-1}$-$C_{1-4}$ haloalkyl, -$(L^1)_{0-1}$-$C_{1-4}$ heteroalkyl, -$(L^2)_{0-1}$-$C_{3-8}$ cycloalkyl, -$(L^2)_{0-1}$-3-7-membered heterocycloalkyl, -$(L^2)_{0-1}$-6-10-membered aryl, -$(L^2)_{0-1}$-5-10-membered heteroaryl.

$L^1$ is selected from the group consisting of —O—, —N(H)—, —S—, —N($C_1$, alkyl)- and =O.

$L^2$ is selected from the group consisting of —O—, —N(H)—, —N($C_1$, alkyl)-, —S—, =O, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene.

$R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5-membered cycloalkyl, 3-5-membered heterocycloalkyl, $C_{1-6}$ alkoxy, $C_{1-6}$ alkylamino, $C_{1-6}$ dialkylamino, $C_{1-6}$ alkylthio, =O, —$NH_2$, —CN, —$NO_2$ and —$SF_5$.

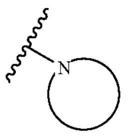

is an optionally substituted 3- to 12-membered N-containing heterocycloalkyl.

$R^5$ and $R^6$ are independently selected from straight or branched $C_{1-6}$ alkyl, or $R^3$ and $R^6$ together with the oxygen atoms to which they are attached and the boron atom form 5- to 7-membered heterocyclic ring, wherein the each ring carbon atom may be substituted with 1 or 2 $C_{1-4}$ straight chain alkyl groups.

The process of the seventh aspect comprises steps A to C.

In step A, compound (ix) is combined with a halogenation reagent in a solvent and reacted to form compound (x).

In step B, compound (x) is borylated with a borylation reagent to form a solution of compound (iv).

In step C, a solution of compound (iv), compound (iii), a catalyst, a base and a solvent is formed and reacted to form compound (v).

A eighth additional aspect of the present disclosure is directed to a process for preparing sulfone compound (v) according to the following reaction scheme:

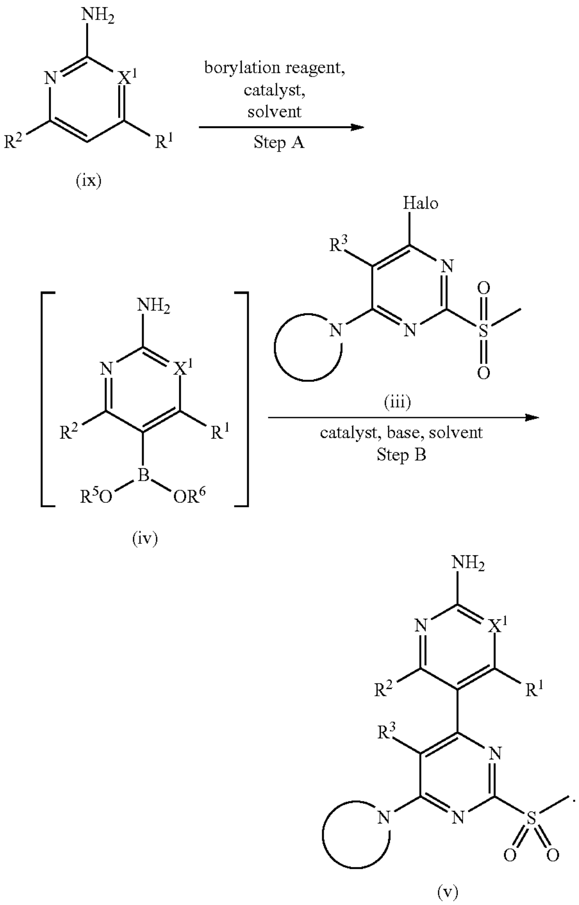

In said eighth aspect, $R^1$, $R^2$ and $R^3$ are each independently selected from the group consisting of H, F, Cl, Br, I, $C_{1-6}$ alkyl and $C_{1-6}$ haloalkyl.

$X^1$ is C—$R^4$, wherein $R^4$ is selected from the group consisting of —F, —Cl, —Br, —I, $-(L^1)_{0-1}-C_{1-6}$ alkyl, $-(L^1)_{0-1}-C_{1-6}$ haloalkyl, $-(L^1)_{0-1}-C_{1-6}$ heteroalkyl, $-(L^2)_{0-1}-C_{3-8}$ cycloalkyl, $-(L^2)_{0-1}$-3-7-membered heterocycloalkyl, $-(L^2)_{0-1}$-6-10-membered aryl, $-(L^2)_{0-1}$-5-10-membered heteroaryl.

$L^1$ is selected from the group consisting of —O—, —N(H)—, —S—, —N($C_{1-6}$ alkyl)- and =O.

$L^2$ is selected from the group consisting of —O—, —N(H)—, —N($C_{1-6}$ alkyl)-, —S—, =O, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene.

$R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5-membered cycloalkyl, 3-5-membered heterocycloalkyl, $C_{1-6}$ alkoxy, $C_{1-6}$ alkylamino, $C_{1-6}$ dialkylamino, $C_{1-6}$ alkylthio, =O, $—NH_2$, —CN, $—NO_2$ and $—SF_5$.

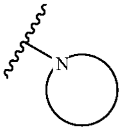

is an optionally substituted 3- to 12-membered N-containing heterocycloalkyl.

$R^5$ and $R^6$ are independently selected from straight or branched $C_{1-6}$ alkyl, or $R^5$ and $R^6$ together with the oxygen atoms to which they are attached and the boron atom form 5- to 7-membered heterocyclic ring, wherein the each ring carbon atom may be substituted with 1 or 2 $C_{1-4}$ straight chain alkyl groups.

The process of the eight aspect comprises steps A and B.

In step A, compound (ix) is directly borylated with a borylation reagent to form a reaction product mixture comprising compound (iv) predominantly in solution.

In step B, the reaction product mixture from step A is combined with compound (iii), a catalyst, a base and a solvent, and reacted to form compound (v).

An additional ninth aspect of the present disclosure is directed to the use of the process of the eighth aspect for preparing a compound of formula (I):

I

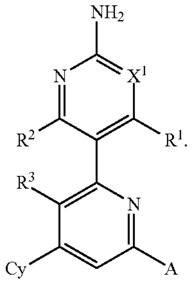

In said ninth aspect, $R^1$, $R^2$ and $R^3$ are each independently selected from the group consisting of H, F, Cl, Br, I, $C_{1-6}$ alkyl and $C_{1-6}$ haloalkyl.

$X^1$ is C—$R^4$, wherein $R^4$ is selected from the group consisting of —F, —Cl, —Br, —I, $-(L^1)_{0-1}-C_{1-6}$ alkyl, $-(L^1)_{0-1}-C_{1-6}$ haloalkyl, $-(L^1)_{0-1}-C_{1-6}$ heteroalkyl, $-(L^2)_{0-1}-C_{3-8}$ cycloalkyl, $-(L^2)_{0-1}$-3-7-membered heterocycloalkyl, $-(L^2)_{0-1}$-6-10-membered aryl, $-(L^2)_{0-1}$-5-10-membered heteroaryl.

$L^1$ is selected from the group consisting of —O—, —N(H)—, —S—, —N($C_{1-6}$ alkyl)- and =O.

$L^2$ is selected from the group consisting of —O—, —N(H)—, —N($C_{1-6}$ alkyl)-, —S—, =O, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene.

$R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5-membered cycloalkyl, 3-5-membered heterocycloalkyl, $C_{1-6}$ alkoxy, $C_{1-6}$ alkylamino, $C_{1-6}$ dialkylamino, $C_{1-6}$ alkylthio, =O, —$NH_2$, —CN, —$NO_2$ and —$SF_5$.

Cy and A are independently an optionally substituted 3- to 12-membered N-containing heterocycloalkyl

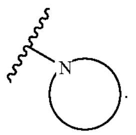

$R^5$ and $R^6$ are independently selected from straight or branched $C_{1-6}$ alkyl, or $R^5$ and $R^6$ together with the oxygen atoms to which they are attached and the boron atom form 5- to 7-membered heterocyclic ring, wherein the each ring carbon atom may be substituted with 1 or 2 $C_{1-4}$ straight chain alkyl groups.

An additional tenth aspect of the present disclosure is directed to compound (24), a species of formula (v):

(24)

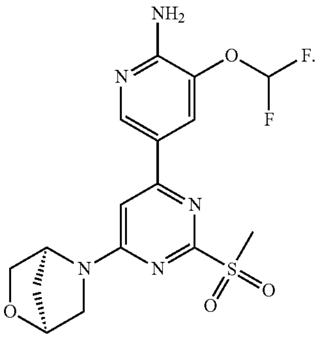

An additional eleventh aspect of the present disclosure is directed to a compound of formula (va)

(va)

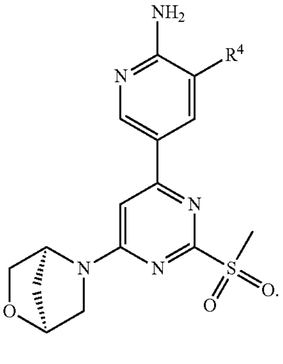

$R^4$ is selected from the group consisting of —F, —Cl, —Br, —I, -$(L^1)_{0-1}$-Cia alkyl, -$(L^1)_{0-1}$-$C_{1-6}$ haloalkyl, -$(L^1)_{0-1}$-$C_{1-6}$ heteroalkyl, -$(L^2)_{0-1}$-$C_{3-8}$ cycloalkyl, -$(L^2)_{0-1}$-3-7-membered heterocycloalkyl, and -$(L^2)_{0-1}$-6-10-membered aryl.

$L^1$ is selected from the group consisting of —O—, —N(H)—, —S—, —N($C_{1-4}$ alkyl)- and =O.

$L^2$ is selected from the group consisting of —O—, —N(H)—, —N($C_{1-6}$ alkyl)-, —S—, =O, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene.

$R^4$ is optionally substituted on carbon atoms and heteroatoms with $R^{R4}$ substituents selected from the group consisting of F, Cl, Br, I, $C_{1-6}$ alkyl, $C_{1-6}$ haloalkyl, 3-5-membered cycloalkyl, 3-5-membered heterocycloalkyl, $C_{1-6}$ alkoxy, $C_{1-6}$ alkylamino, $C_{1-6}$ dialkylamino, Cia alkylthio, =O, —$NH_2$, —CN, —$NO_2$ and —$SF_5$.

Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include linear and branched groups including vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl," "carbocyclic," or "carbocycle" refers to hydrocarbon ring system having specified overall number of ring atoms (e.g., 3 to 12 ring atoms in a 3 to 12 membered cycloalkyl or C3-12 cycloalkyl) and being fully saturated or having no more than one double bond between ring vertices for a 3-5 membered cycloalkyl and being saturated or having no more than two double bonds between ring vertices for 6 or larger membered cycloalkyl. The monocyclic or polycyclic ring may be optionally substituted with one or more oxo groups. As used herein, "cycloalkyl," "carbocyclic," or "carbocycle" is also meant to refer to polycyclic (including fused and bridged bicyclic, fused and bridged polyclic and spirocyclic) hydrocarbon ring system such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —$CH_2$—$CH_2$—O—$CH_3$, —$CH_2$—$CH_2$—O—$CF_3$, —$CH_2$—$CH_2$—NH—

$CH_3$, —$CH_2$—$CH_2$—$N(CH_3)$—$CH_3$, —$CH_2$—S—$CH_2$—$CH_3$, —S(O)—$CH_3$, —$CH_2$—$CH_2$—$S(O)_2$—$CH_3$, —CH=CHO—$CH_3$, —$Si(CH_3)_3$, —$CH_2$—CH=N—$OCH_3$, and —CH=C=$N(CH_3)$—$CH_3$. Up to two heteroatoms can be consecutive, such as, for example, —$CH_2$—NH—$OCH_3$ and —$CH_2$—O—$Si(CH_3)_3$.

The term "heterocycloalkyl," "heterocyclic," or "heterocycle" refers to a saturated or partially unsaturated ring system radical having from the indicated number of overall number of stated ring atoms and containing from one to five heteroatoms selected from N, O, and S, wherein the nitrogen and sulfur atoms are optionally oxidized, nitrogen atom(s) are optionally quaternized, as ring atoms (e.g., a 3 to 12 membered heterocycloalkyl that would have 3 to 12 ring atoms and include at least one heteroatom, which also could be referred to as a $C_{2-11}$ heterocycloalkyl). Unless otherwise stated, a "heterocycloalkyl," "heterocyclic," or "heterocycle" ring system can be a monocyclic or a fused, bridged, or spirocyclic polycyclic (including a fused bicyclic, bridged bicyclic or spirocyclic) ring system. The monocyclic or polycyclic ring may be optionally substituted with one or more oxo groups. A "heterocycloalkyl," "heterocyclic," or "heterocycle" group can be attached to the remainder of the molecule through one or more ring carbons or heteroatoms. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and the like. A "heterocycloalkyl," "heterocyclic," or "heterocycle" can include mono- and poly-halogenated variants thereof. A "cyclic ether" refers to a heterocycle containing one or more oxygen ring atoms with examples including tetrahydrofuran, methyl-tetrahydrofuran, 1,4-dioxane, and dioxolane.

The term "alkylene" by itself or as part of another substituent means a divalent radical derived from an alkane, as exemplified by —$CH_2CH_2CH_2CH_2$—, and can be branched. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$—, —$CH_2$—S—$CH_2$—$CH_2$—NH—$CH_2$—, —$CH_2$—CH=C(H)$CH_2$—O—$CH_2$— and —S—$CH_2$—C≡C—. The term "heteroalkylene" is also meant to include mono and poly-halogenated variants.

The term "alkoxylene" and "aminoalkylene" and "thioalkylene" by itself or as part of another substituent means a divalent radical, saturated or unsaturated or polyunsaturated, derived from alkoxy, alkylamino and alkylthio, respectively, as exemplified by —$OCH_2CH_2$—, —O—$CH_2$—CH=CH—, —N(H)$CH_2$C(H)($CH_3$)$CH_2$— and —S—$CH_2$—C≡C—. The term "alkoxylene" and "aminoalkylene" and "thioalkylene" are meant to include mono and poly halogenated variants.

The terms "alkoxy," "alkylamino" and "alkylthio", are used in their conventional sense, and refer to those alkyl groups attached to the remainder of the molecule via an oxygen atom ("oxy"), an amino group ("amino") or thio group, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, difluoromethyl, and the like. The term "(halo)alkyl" as used herein includes optionally halogenated alkyl. Thus the term "(halo)alkyl" includes both alkyl and haloalkyl (e.g., monohaloalkyl and polyhaloalkyl).

The term "aryl" means, unless otherwise stated, a polyunsaturated, typically aromatic, hydrocarbon ring, which can be a single ring or multiple rings (up to three rings) which are fused together. The term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

The above terms (e.g., "alkyl," "aryl" and "heteroaryl"), in some embodiments, will include both substituted and unsubstituted forms of the indicated radical. Preferred substituents for each type of radical are provided below.

As used herein, "alkylaromatic" refers to an aryl group substituted with one or more alkyl groups. Examples include toluene, ethylbenzene, p-xylene, m-xylene, and mesitylene.

As used herein, "haloaromatic" refers to an aryl group substituted with one or more halo groups. Examples include toluene, ethylbenzene, p-xylene, m-xylene, and mesitylene.

Substituents for the alkyl radicals (including those groups often referred to as alkylene, alkenyl, alkynyl, heteroalkyl and cycloalkyl) can be a variety of groups including, but not limited to, -halogen, =O, —OR', —NR'R", —SR', —SiR'R"R"', —OC(O)R', —C(O)R', —$CO_2$R', —CONR'R", —OC(O)NR'R", —NR"C(O)R', —NR"'C(O)NR'R", —NR"C(O)$_2$R', —NHC($NH_2$)=NH, —NRC($NH_2$)=NH, —NHC($NH_2$)=NR', —NR"'C(NR'R")=N—CN, —NR"'C(NR'R")=NOR', —NHC($NH_2$)=NR', —S(O)R', —S(O)$_2$R', —S(O)$_2$NR'R", —NR'S(O)$_2$R", —NR"'S(O)$_2$NR'R", —CN, —$NO_2$, —$(CH_2)_{1-4}$—OR', —$(CH_2)_{1-4}$—NR'R", —$(CH_2)_{1-4}$—SR', —$(CH_2)_{1-4}$—SiR'R"R"', —$(CH_2)_{1-4}$—OC(O)R', —$(CH_2)_{1-4}$—C(O)R', —$(CH_2)_{1-4}$—$CO_2$R', —$(CH_2)_{1-4}$CONR'R", in a number ranging from zero to (2m'+1), where m' is the total number of carbon atoms in such radical. R', R" and R'" each independently refer groups including, for example, hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-6}$ alkoxy or $C_{1-6}$ thioalkoxy groups, or unsubstituted aryl-$C_{1-4}$ alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substituents for alkyl radicals, including heteroalkyl, alkylene, include for example, =O, =NR',N—OR', =N—CN, and =NH, wherein R' include substituents as described above. When a substituent for the alkyl radicals (including those groups often referred to as alkylene, alkenyl, alkynyl, heteroalkyl and cycloalkyl) contains an alkylene, alkenylene, alkynylene linker (e.g., $—(CH_2)_{1-4}—$NR'R" for alkylene), the alkylene linker includes halo variants as well. For example, the linker "$—(CH_2)_{1-4}—$" when used as part of a substituent is meant to include difluoromethylene, 1,2-difluoroethylene, etc.

Similarly, substituents for the aryl and heteroaryl groups are varied and are generally selected from the group including, but not limited to, -halogen, —OR', —OC(O)R', —NR'R", —SR', —R', —CN, $—NO_2$, $—CO_2R'$, —CONR'R", —C(O)R', —OC(O)NR'R", —NR"C(O)R', $—NR"C(O)_2R'$, —NR'C(O)NR"R'", $—NHC(NH_2)=NH$, $—NR'C(NH_2)=NH$, $—NHC(NH_2)=NR'$, —S(O)R', $—S(O)_2R'$, $—S(O)_2NR'R"$, $—NR'S(O)_2R"$, $—N_3$, perfluoro-$C—_4$ alkoxy, and perfluoro-$C_{1-4}$ alkyl, $—(CH_2)_{1-4}—$OR', $—(CH_2)_{1-4}—$NR'R", $—(CH_2)_{1-4}—$SR', $—(CH_2)_{1-4}—$SiR'R"R'", $—(CH_2)_{1-4}—$OC(O)R', $—(CH_2)_{1-4}—$C(O)R', $—(CH_2)_{1-4}—CO_2R'$, $—(CH_2)_{1-4}$CONR'R", in a number ranging from zero to the total number of open valences on the aromatic ring system; and where R', R" and R'" are independently selected from hydrogen, $C_{1-6}$ alkyl, $C_{3-6}$ cycloalkyl, $C_{2-6}$ alkenyl, $C_{2-6}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms. When a substituent for the aryl or heteroaryl group contains an alkylene, alkenylene, alkynylene linker (e.g., $—(CH_2)_{1-4}—$NR'R" for alkylene), the alkylene linker includes halo variants as well. For example, the linker "$—(CH_2)_{1-4}—$" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "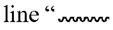" that intersects a bond in a chemical structure fragment indicates the point of attachment of the bond to which the wavy bond intersects in the chemical structure fragment to the remainder of a molecule or structural formula.

As used herein, the term "reaction mixture" refers to a mixture of reactants. As used herein, the term "reaction product mixture" refers to a mixture of reaction products formed from the reaction mixture.

As used herein, the representation of a group (e.g., $X^d$) in parenthesis followed by a subscript integer range (e.g., $(X^d)_{0-2}$) means that the group can have the number of occurrences as designated by the integer range. For example, $(X^d)_{0-1}$ means the group $X^d$ can be absent or can occur one time.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

As used herein, "regioisomer" refers to a positional isomer where molecules with the same molecular formula have different bonding patterns where the position of a functional group or other substituent changes with respect to the parent structure. Examples include: p-xylene and m-xylene; and pentan-1-ol, pentan-2-ol, and pentan-3-ol.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., *Stereochemistry of Organic Compounds*, John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process.

The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

As used herein, a "polymorph" or "polymorphism" refers to the ability of a substance to exist in more than one crystal form, where the different crystal forms of a particular substance are referred to as "polymorphs." In general, it is believed that polymorphism may be affected by the ability of a molecule of a substance to change its conformation or to form different intermolecular or intra-molecular interactions, particularly hydrogen bonds, which is reflected in different atom arrangements in the crystal lattices of different polymorphs. The different polymorphs of a substance may possess different energies of the crystal lattice and, thus, in solid state they may show different physical properties such as form, density, melting point, color, stability, solubility, dissolution rate, etc., which may, in turn, affect properties such as, and without limitation, the stability, dissolution rate and/or bioavailability of a given polymorph and its suitability for use as a pharmaceutical and in pharmaceutical compositions.

As used herein, "morphology" refers to the external shape of the crystal and the planes present, without reference to the internal structure. Crystals can display different morphology based on different conditions, such as, for example, growth rate, stirring, and the presence of impurities.

As used herein, "solvate" refers to any form of a compound that is bound by a non-covalent bond to another molecule (such as a polar solvent). Such solvates are typically crystalline solids having a substantially fixed molar ratio of solute and solvent. Representative solvents include water, methanol, ethyl acetate, acetic acid, ethanolamine, n-heptane, N,N-dimethylacetamide, anisole, ethanol (EtOH), toluene, 2-propanol, 1-butanol, 2-methyltetrahydrofuran (2-Me-THF), tetrahydrofuran (THF), isobutyl alcohol, and dimethyl sulfoxide (DMSO). The term "hydrate" refers to the complex where the solvent molecule is water.

As used herein, the term "seed" can be used as a noun to describe one or more crystals of a crystalline compound formula I (e.g., compound formula I polymorph Form A). The term "seed" can also be used as a verb to describe the act of introducing said one or more crystals of a crystalline compound formula I into an environment (including, but not limited to e.g., a solution, a mixture, a suspension, or a dispersion) thereby resulting in the formation of more crystals of the crystalline compound formula I.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, *Greene's Protective Groups in Organic Synthesis* 4*th edition*, Wiley-Interscience, New York, 2006.

As used herein, the term "salts" is meant to include salts of the active compounds which are prepared with relatively nontoxic acids or bases (e.g., those salts that are pharmaceutically acceptable), depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., *Pharmaceutical Salts*, Journal of Pharmaceutical Science, 1977, 66, 1-19). Certain specific compounds of the present invention contain both basic and acidic functionalities that allow the compounds to be converted into either base or acid addition salts.

As used herein, the terms, "predominantly" and "substantially" refer to greater than 50%, at least 75%, at least 90% at least 95%, or at least 99% on a population %, w/w %, w/v %, v/v %, or mole % basis.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

As used herein, the term "organic base" refers to an organic compound containing one or more nitrogen atoms, and which acts as a base. One example of an organic base is a tertiary amine such as a trialkyl amine, wherein the alkyl groups are the same or different and may be linear or branched, such as diethylamine, diisopropylethylamine (DIPEA), triethylamine (TEA), di-n-butylamine and tri-n-butylamine. Another example of an organic base is a cyclic amine, such as Quinuclidine, 2,2,6,6-Tetramethylpiperidine (TMP), Pempidine (PMP), 1,4-Diazabicyclo[2.2.2]octane (DABCO), and N-methyl-morpholine (NMM). Cyclic amine may also be classified as secondary or tertiary amines. Other examples of organic bases include amidine and guanidine bases, such as 1,1,3,3-Tetramethylguanidine (TMG), 7-Methyl-1,5,7-triazabicyclo(4.4.0)dec-5-ene (MTBD), 1,8-Diazabicyclo[5.4.0]undec-7-ene (DBU), 1,5-Diazabicyclo[4.3.0]non-5-ene (DBN), 1,5,7-Triazabicyclo(4.4.0)dec-5-ene (TBD), and 1,5-Diazabicyclo[4.3.0]non-5-ene (DBN).

As used herein, the term "inorganic base" refers to a base comprising an inorganic component. Examples of inorganic bases include, but are not limited to, alkali metal hydroxide, ammonium hydroxide, potassium carbonate, potassium bicarbonate, sodium carbonate, and sodium bicarbonate.

As used herein, the term "strong base" refers to abase that completely or almost completely dissociates in water.

As used herein, the term "polar aprotic solvent" refers to any polar solvent not having a proton-donating ability. Examples include, without any limitation, 2-methyltetrahydrofuran, tetrahydrofuran, ethyl acetate, propyl acetate (e.g., isopropyl acetate, iPrOAc), acetone, dimethylsulfoxide, N,N-dimethylformamide, acetonitrile ($CH_3CN$), N,N-dimethylacetamide, N-methylpyrrolidone (NMP), hexamethylphosphoramide, and propylene carbonate.

As used herein, the term "polar protic solvent" refers to any polar solvent having a proton-donating ability. Examples include, without limitation, water, methanol, ethanol, 1-propanol, 2-propanol, 1-butanol, formic acid, nitromethane and acetic acid.

As used herein, the term "polar organic solvent" refers to both polar aprotic solvents and polar protic solvents excluding water.

As used herein, the term "non-polar solvent" refers to solvents that contain bonds between atoms with similar electronegativities, such as carbon and hydrogen, such that the electric charge on the molecule is evenly distributed. Non-polar solvents are characterized as having a low dielectric constant. Examples include, without limitation, pentane (e.g., n-pentane), hexane (e.g., n-hexane), heptane (e.g., n-heptane), cyclopentane, methyl tert-butyl ether, diethyl ether, toluene, benzene, 1,4-dioxane, carbon tetrachloride, chloroform and dichloromethane (DCM). In some aspects, the non-polar solvent has a dielectric constant of less than 2, examples of which include, without limitation, n-pentane, n-hexane and n-heptane. As compared to other non-polar solvents, DCM exhibits some degree of polarity at the bond level (i.e., between carbon and chlorine), but only a small degree of polarity at the molecular level due to symmetry-based cancellation of polarity.

As used herein, the term "solvent" refers to any of polar aprotic solvents, polar protic solvents, and non-polar solvents.

As used herein, the term "anti-solvent" refers to a solvent in which the referenced compound is poorly soluble and which induces precipitation or crystallization of said compound from solution.

As used herein, unless otherwise indicated, the term "percent yield" refers to yield on a molar basis for the indicated reaction, calculated from actual yield to a theoretical yield based on the reactant that is not in stoichiometric excess. For instance, if 1.0 moles of compound A are reacted with 1.1 molar equivalents of compound B to form 0.9 moles of compound C, the percent yield (based on compound A) would be (0.9)/(1.0)*100=90%.

As used herein, the term "purity", unless otherwise indicated, refers to the amount of a compound in a sample as compared to the total amount of compounds in the sample. In some aspects, purity may be measured by high pressure liquid chromatography (HPLC) analysis where the area % a product represents purity.

As used herein, the terms "area percent" or "area %" in reference to purity refers to the area percent of a peak of a compound in a chromatogram (such as an HPLC chromatogram) as a percentage of the total area of all peaks.

Where the applicant has defined an embodiment or a portion thereof with an open-ended term such as "comprising," it should be readily understood that (unless otherwise stated) the description should be interpreted to also describe such an embodiment using the terms "consisting essentially of" or "consisting of."

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claims.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

As used herein, the indefinite articles "a" and "an" preceding an element or component of the disclosure are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

Synthetic Processes

The processes of the present disclosure are directed to the preparation of a compound of Formula I:

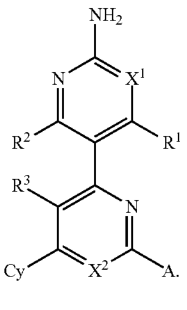

I $R^1$, $R^2$ and $R^3$ are each independently selected from the group consisting of H, F, Cl, Br, I, $C_{1-4}$ alkyl and $C_{1-6}$ haloalkyl.

$X^1$ is C—$R^4$, wherein $R^4$ is selected from the group consisting of —F, —Cl, —Br, —I, -$(L^1)_{0-1}$-$C_{1-6}$ alkyl, -$(L^1)_{0-1}$-$C_{1-6}$ haloalkyl, -$(L^1)_{0-1}$-$C_{1-6}$ heteroalkyl, -$(L^2)_{0-1}$-$C_{3-8}$ cycloalkyl, -$(L^2)_{0-1}$-3-7-membered heterocycloalkyl, -$(L^2)_{0-1}$-6-10-membered aryl, and -$(L^2)_{0-1}$-5-10-membered heteroaryl.

$L^1$ is selected from the group consisting of —O—, —N(H)—, —S—, —N($C_{1-4}$ alkyl)- and =O.

$L^2$ is selected from the group consisting of —O—, —N(H)—, —N($C_{1-4}$ alkyl)-, —S—, =O, $C_{1-4}$ alkylene, $C_{1-4}$ alkenylene, $C_{1-4}$ alkynylene, $C_{1-4}$ alkoxylene, $C_{1-4}$ aminoalkylene, $C_{1-4}$ thioalkylene and $C_{1-4}$ heteroalkylene.

$R^4$ is optionally substituted on carbon atoms and heteroatoms with $R^{R4}$ substituents selected from the group consisting of F, Cl, Br, I, $C_{1-4}$ alkyl, $C_{1-4}$ haloalkyl, 3-5-membered cycloalkyl, 3-5-membered heterocycloalkyl, $C_{1-4}$ alkoxy, $C_{1-4}$ alkylamino, $C_{1-4}$ dialkylamino, $C_{1-6}$ alkylthio, =O, —$NH_2$, —CN, —$NO_2$ and —$SF_5$.

$X^2$ is N.

A is a 3- to 12-membered, 5- to 9-membered, 6- to 8-membered, or 7-membered N-containing heterocycloalkyl of the following structure:

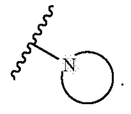 [SMILES: *N]

A is optionally substituted with 1-5 $R^A$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^A)_{0-1}$-3-8-membered cycloalkyl, -$(L^A)_{0-1}$-3-8-membered heterocycloalkyl, -$(L^A)_{0-1}$-5-6-membered heteroaryl, -$(L^A)_{0-1}$-$C_6$ aryl, -$(L^A)_{0-1}$-$NR^{R1a}R^{R1b}$, -$(L^A)_{0-1}$-$OR^{R1a}$, -$(L^A)_{0-1}$-$SR^{R1a}$, -$(L^A)_{0-1}$—N($R^{R1a}$)C(=$Y^1$)$OR^{R1c}$, -$(L^A)_{0-1}$-OC(=O)N($R^{R1a}$)($R^{R1b}$), -$(L^A)_{0-1}$-N($R^{R1a}$)C(=O)N($R^{R1a}$)($R^{R1b}$), -$(L^A)_{0-1}$-C(=O)N($R^{R1a}$)($R^{R1b}$), $(L^A)_{0-1}$-N($R^{R1a}$)C(=O)$R^{R1b}$, -$(L^A)_{0-1}$-C(=O)$OR^{R1a}$, -$(L^A)_{0-1}$-OC(=O)$R^{R1a}$, -$(L^A)_{0-1}$-P(=O)($OR^{R1a}$)($OR^{R1b}$), -$(L^A)_{0-1}$-$S(O)_{1-2}R^{R1c}$, -$(L^A)_{0-1}$-$S(O)_{1-2}$N($R^{R1a}$)($R^{R1b}$), -$(L^A)_{0-1}$-N($R^{R1a}$)$S(O)_{1-2}$N($R^{R1a}$)($R^{R1b}$) and -$(L^A)_{0-1}$-N($R^{R1a}$)$S(O)_{1-2}$($R^{R1c}$).

$Y^1$ is O or S.

$L^A$ is selected from the group consisting of $C_{1-4}$alkylene, $C_{1-4}$ heteroalkylene, $C_{1-4}$ alkoxylene, $C_{1-4}$ aminoalkylene, $C_{1-4}$ thioalkylene, $C_{2-4}$ alkenylene, and $C_{2-4}$ alkynylene.

$R^{R1a}$ and $R^{R1b}$ are each independently selected from the group consisting of hydrogen, $C_{1-8}$ alkyl, $C_{1-8}$ haloalkyl, 3-8-membered cycloalkyl, phenyl, benzyl, 5-6-membered heteroaryl and 3-8-membered heterocycloalkyl.

$R^{R1c}$ is selected from the group consisting of $C_{1-8}$ alkyl, $C_{1-8}$ haloalkyl, 3-8-membered cycloalkyl, phenyl, benzyl, 5-6-membered heteroaryl and 3-7-membered heterocycloalkyl, and wherein $R^A$ is optionally substituted on carbon atoms and heteroatoms with $R^{RA}$ substituents selected from, F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-$S(O)_{0-2}$—, $C_{1-4}$ (halo)alkyl-N(H)$S(O)_{0-2}$—, $C_{1-4}$ (halo)alkyl-$S(O)_{0-2}$N(H)—, (halo)alkyl-N(H)—$S(O)_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C(=O)O—, ((halo)alkyl)$_2$N—C(=O)O—, $C_{1-4}$ alkylthio, $C_{1-4}$ alkylamino and $C_{1-4}$ dialkylamino.

Cy is a 3- to 12-membered, 4- to 7-membered, 5-membered, or 6-membered N-containing heterocycloalkyl of the structure:

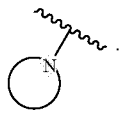

Cy optionally comprises one or two additional heteroatoms selected from the group consisting of O, S, and N.

Cy is optionally substituted on carbon or heteroatoms with $R^{Cy}$ substituents selected from the group consisting of F, Cl, Br, I, —OH, —CN, —$NO_2$, —$SF_5$, $C_{1-8}$ alkyl, $C_{1-8}$ haloalkyl, $C_{1-8}$ heteroalkyl, -$(L^{Cy})_{0-1}$-3-8-membered cycloalkyl, -$(L^{Cy})_{0-1}$-3-8-membered heterocycloalkyl, -$(L^{Cy})_{0-1}$-5-6-membered heteroaryl, -$(L^{Cy})_{0-1}$-phenyl, -$(L^{Cy})_{0-1}$-$NR^{RCa}R^{RCb}$, -$(L^{Cy})_{0-1}$—$OR^{RCa}$, -$(L^{Cy})_{0-1}$-$SR^{RCa}$, -$(L^{Cy})_{0-1}$-N($R^{RCa}$)C(=$Y^1$)$OR^{RCc}$, -$(L^{Cy})_{0-1}$-OC(=O)N($R^{RCa}$)($R^{RCb}$), $(L^{Cy})_{0-1}$-N($R^{RCa}$)C(=O)N($R^{RCa}$)($R^{RCb}$), -$(L^{Cy})_{0-1}$-C(=O)N($R^{RCa}$)($R^{RCb}$), -$(L^{Cy})_{0-1}$-N($R^{RCa}$)C(=O)$R^{RCb}$, -$(L^{Cy})_{0-1}$-C(=O)$OR^{RCa}$, -$(L^{Cy})_{0-1}$-OC(=O)$R^{RCa}$, -$(L^{Cy})_{0-1}$-P(=O)($OR^{RCa}$)($OR^{RCb}$), -$(L^{Cy})_{0-1}$-$S(O)_{1-2}R^{RCc}$, -$(L^{Cy})_{0-1}$-$S(O)_{1-2}$N($R^{RCa}$)($R^{RCb}$), -$(L^{Cy})_{0-1}$-N($R^{RCa}$)$S(O)_{1-2}$N($R^{RCa}$)($R^{RCb}$) and -$(L^{Cy})_{0-1}$-N($R^{RCa}$)$S(O)_{1-2}$($R^{RCc}$.

$L^{Cy}$ is selected from the group consisting of $C_{1-4}$alkylene, $C_{1-4}$ heteroalkylene, $C_{1-4}$alkoxylene, $C_{1-4}$ aminoalkylene, $C_{1-4}$ thioalkylene, $C_{2-4}$ alkenylene, and $C_{2-4}$ alkynylene.

$R^{Ra}$ and $R^{Rb}$ are each independently selected from the group consisting of hydrogen, $C_{1-8}$ alkyl, $C_{1-8}$ haloalkyl, 3-8-membered cycloalkyl, phenyl, benzyl, 5-6-membered heteroaryl and 3-8-membered heterocycloalkyl.

$R^{RCc}$ is selected from the group consisting of $C_{1-8}$ alkyl, $C_{1-8}$ haloalkyl, 3-8-membered cycloalkyl, phenyl, benzyl, 5-6-membered heteroaryl and 3-7-membered heterocycloalkyl.

$R^{Cy}$ is optionally substituted on carbon atoms and heteroatoms with from 1 to 5 $R^{RCy}$ substituents selected from the group consisting of F, Cl, Br, I, —$NH_2$, —OH, —CN, —$NO_2$, =O, —$SF_5$, $C_{1-4}$ alkyl, $C_{1-4}$ haloalkyl, $C_{1-4}$ alkoxy, $C_{1-4}$ (halo)alkyl-C(=O)—, $C_{1-4}$ (halo)alkyl-$S(O)_{0-2}$—, $C_{1-4}$ (halo)alkyl-N(H)$S(O)_{0-2}$—, $C_{1-4}$ (halo)alkyl-$S(O)_{0-2}$N(H)—, (halo)alkyl-N(H)—$S(O)_{0-2}$N(H)—, $C_{1-4}$ (halo)alkyl-C(=O)N(H)—, $C_{1-4}$ (halo)alkyl-N(H)—C(=O)—, ((halo)alkyl)$_2$N—C(=O)—, $C_{1-4}$ (halo)alkyl-OC(=O)N(H)—, $C_{1-4}$ (halo)alkyl-OC(=O)N(H)—, (halo)alkyl-N(H)—C (═O)O—, ((halo)alkyl)$_2$N—C(═O)O—, $C_{1-4}$ alkylthio, $C_{1-4}$ alkylamino and $C_{1-4}$ dialkylamino.

In some aspects, $L^1$ is —O—.

In some aspects, $R^4$ is -$(L^1)_{0-1}$-$C_{1-6}$ haloalkyl. In some aspects, $R^4$ is selected from methoxy, monofluoromethoxy, difluoromethoxy, trifluoromethoxy, ethoxy, propoxy, isopropoxy, butoxy, isobutoxy, tert-butoxy, methyl, monofluoromethyl difluoromethyl, and trifluoromethyl. In some such aspects, $R^4$ is monofluoromethoxy, difluoromethoxy, or trifluoromethoxy. In one aspect, $R^4$ is difluoromethoxy.

In some aspects, $R^1$, $R^2$ and $R^3$ are each hydrogen.

In some aspects, A is optionally substituted with from 1 to 5 $R^A$ substituents selected from the group consisting of F, Cl, Br, I, CN, $CH_3O$—, $CH_3$, cyclopropylmethyl, $CF_3$, and butyl. In some aspects, A is substituted with F. In some particular aspects, A is selected from

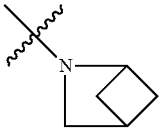
,
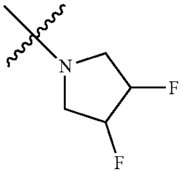
,
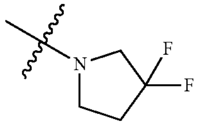
, and
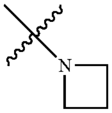
,

In one aspect, A is

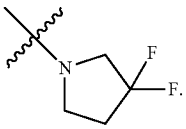 [SMILES: *N1CCC(F)(F)C1]

In some aspects, Cy is selected from

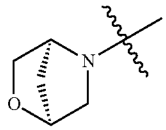
,
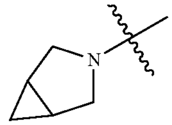
,
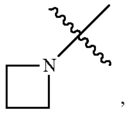
, and
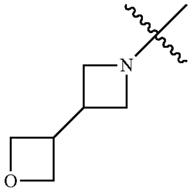
.

In one aspect, $C_y$ is

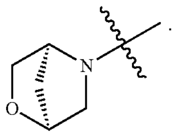 [SMILES: *N1C[C@@H]2C[C@H]1CO2]

In embodiments, $R^1$, $R^2$ and $R^3$ are each H; $X^1$ is C—$R^4$, wherein $R^4$ is -$(L^1)_{0-1}$-$C_{1-4}$ haloalkyl, wherein $L^1$ is —O—; $X^2$ is N; A is 3 to 12 membered N-containing heterocycloalkyl optionally substituted with 1 to 5 $R^A$ substituents wherein each $R^A$ is F; and Cy is 3 to 12 membered N-containing heterocycloalkyl.

In embodiments, $R^1$, $R^2$ and $R^3$ are each H; $X^1$ is C—$R^4$; $R^4$ is selected from monofluoromethoxy, difluoromethoxy, and trifluoromethoxy; A is a 4- to 7-membered N-containing heterocycloalkyl substituted with from 1 to 3 F atoms; and Cy is a 5- to 9-membered N-containing heterocycloalkyl further comprising an oxygen heteroatom.

In embodiments, $R^1$, $R^2$ and $R^3$ are each H; $X^1$ is C—$R^4$, wherein $R^4$ is -$(L^1)_{0-1}$-$C_{1-4}$ haloalkyl, wherein $L^1$ is —O—; $X^2$ is N; A is 3 to 12 membered heterocycloalkyl substituted with 0 to 5 $R^A$ substituents wherein each $R^A$ is F; and Cy is 3 to 12 membered heterocycloalkyl.

In embodiments, $R^4$ is difluoromethoxy.

In embodiments, A is pyrrolidine.

In embodiments, the compound of Formula I has a structure of

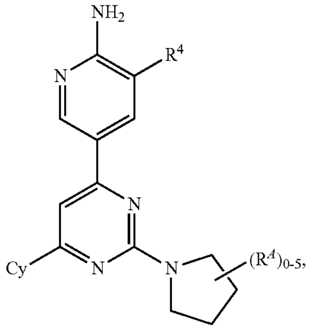

wherein $R^4$ is -$(L^1)_{0-1}$-$C_{1-6}$ haloalkyl, wherein L is —O—; $R^A$ is F; and Cy is 3 to 12 membered heterocycloalkyl.

In embodiments, A is substituted with one or two $R^A$.

In embodiments, A is substituted with two $R^A$.

In embodiments, A is difluoropyrrolidine.

In embodiments, Cy is 2-oxa-5-azabicyclo[2.2.1]heptane.

In embodiments, Cy is (1S,4S)-2-oxa-5-azabicyclo[2.2.1]heptane.

In embodiments, Cy is

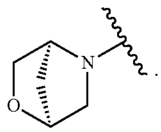 [SMILES: *N1C[C@@H]2C[C@H]1CO2]

In embodiments, the compound of Formula I has a structure of

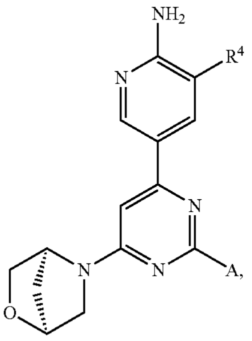

wherein $R^4$ is $-(L^1)_{0-1}-C_{1-6}$ haloalkyl, wherein $L^1$ is —O—; $X^2$ is N; A is 3 to 12 membered heterocycloalkyl substituted with 0 to 5 $R^{A}$ substituents wherein each $R^{A}$ is F;

In embodiments, A is pyrrolidine, and Cy is 2-oxa-5-azabicyclo[2.2.1]heptane.

In embodiments, $R^4$ is difluoromethoxy, A is pyrrolidine, and Cy is 2-oxa-5-azabicyclo[2.2.1]heptane.

In embodiments, the processes of the present disclosure are directed to the preparation of 3-(difluoromethoxy)-5-[2-(3,3-difluoropyrrolidin-1-yl)-6-[(1S,4S)-2-oxa-5-azabicyclo[2.2.1]heptan-5-yl]pyrimidin-4-yl]pyridin-2-amine, or a pharmaceutically acceptable salt thereof.

In embodiments, the processes of the present disclosure are directed to the preparation of

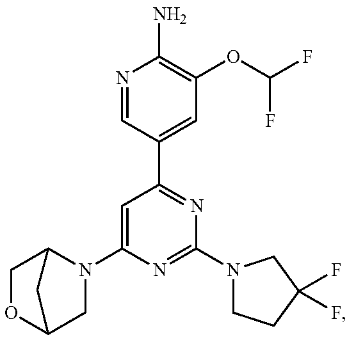 [SMILES: Nc1ncc(-c2cc(N3CC4CC3CO4)nc(N3CCC(F)(F)C3)n2)cc1OC(F)F]

or a pharmaceutically acceptable salt thereof.

In embodiments, the processes of the present disclosure are directed to the preparation of

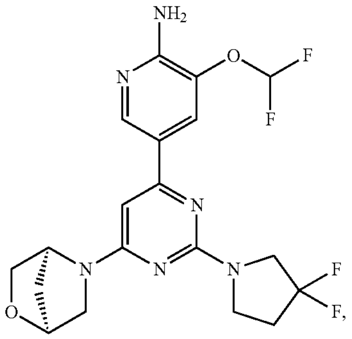 [SMILES: Nc1ncc(-c2cc(N3C[C@@H]4C[C@H]3CO4)nc(N3CCC(F)(F)C3)n2)cc1OC(F)F]

or a pharmaceutically acceptable salt thereof.

In one aspect, the compound of formula I is compound 1 below where compound 1 is a species of compound I

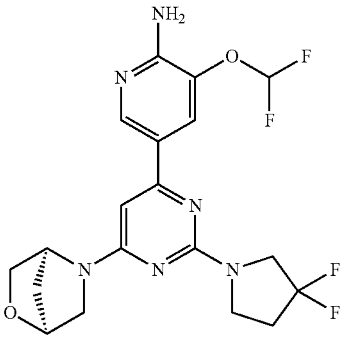

or 5-(6-((1S,4S)-2-oxa-5-azabicyclo[2.2.1]heptan-5-yl)-2-(3,3-difluoropyrrolidin-1-yl)pyrimidin-4-yl)-3-(difluoromethoxy)pyridin-2-amine, or 3-(difluoromethoxy)-5-[2-(3,3-difluoropyrrolidin-1-yl)-6-[(1S,4S)-2-oxa-5-azabicyclo[2.2.1]heptan-5-yl]pyrimidin-4-yl]pyridin-2-amine (compound 1).

The processes of the present disclosure comprise performing a coupling reaction between a sulfone compound (iii) and a boronate reagent (iv) with a catalyst in the presence of a base and a solvent to provide compound (v) according to the following scheme:

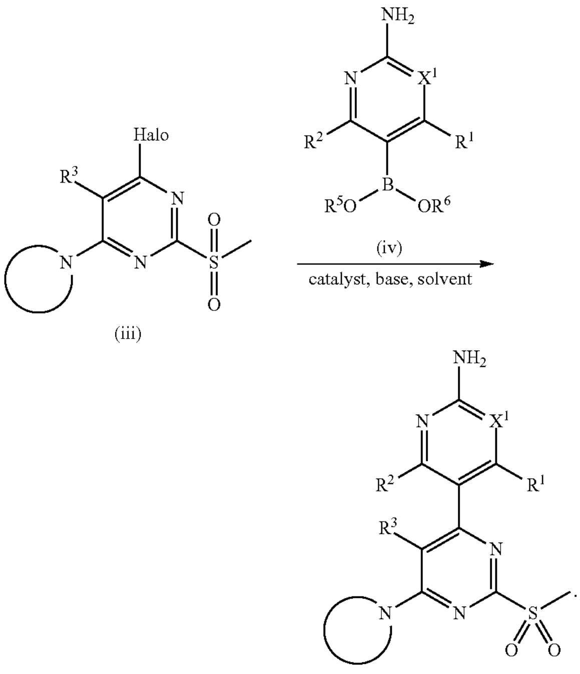

(iii)
(iv)
(v)

$R^5$ and $R^6$ are each independently selected from straight or branched $C_{1-6}$ alkyl, or $R^5$ and $R^6$ together with the oxygen atoms to which they are attached and the boron atom form a 5- to 7-membered heterocyclic ring, wherein each ring carbon atom may be substituted with 1 or 2 $C_{1-4}$ straight-chain alkyl groups.

The processes of the present disclosure further comprise displacing the methoxysulfonyl group of compound (v) under basic conditions in a solvent with a 3 to 12-membered amine-containing heterocycloalkyl compound (vi) to provide compound formula I, according the following scheme:

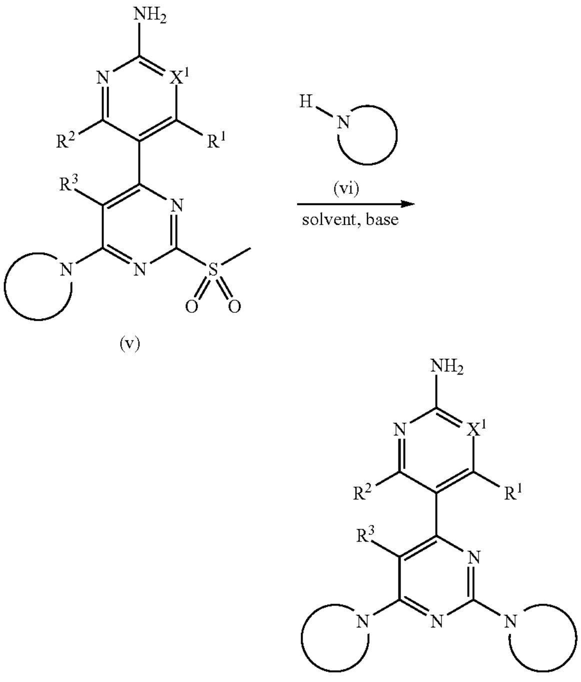

(v) (vi) I

Preparation of Compound (v) from Compounds (iii) and (iv)

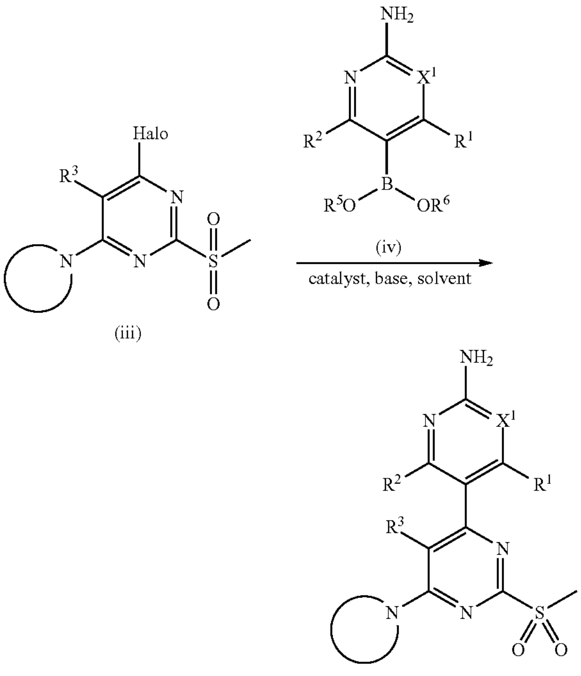

(iii) (iv) (v)

A reaction mixture is formed from the solvent, compound (iii), a stoichiometric excess of compound (iv), the base and the catalyst. In some aspects, the reaction mixture is a suspension. The reaction mixture is heated to a reaction temperature with mixing and held at the reaction temperature with mixing for a time sufficient to reach a desired conversion, thereby forming a reaction product mixture comprising compound (v) in solution. In-process testing for the percentage of unreacted compound (iii) may be done to evaluate the degree of conversion.

In some aspects, the concentration of compound (iii) in the reaction mixture may suitably be about 10 g/L, about 25 g/L, about 50 g/L, about 75 g/L, about 100 g/L, about 125 g/L, about 150 g/L, about 175 g/L, or about 200 g/L, and any range constructed therefrom, such as from about 10 g/L to about 200 g/L, from about 25 g/L to about 150 g/L, or from about 50 g/L to about 100 g/L. On a mole per liter basis, the concentration may suitably be about 0.05 mol/L, about 0.1 mol/L, about 0.15 mol/L, about 0.2 mol/L, about 0.25 mol/L, about 0.3 mol/L, about 0.35 mol/L, about 0.4 mol/L, about 0.45 mol/L, or about 0.5 mol/L, and any range constructed therefrom, such as from about 0.05 mol/L to about 0.5 mol/L, from about 0.1 mol/L to about 0.4 mol/L, or from about 0.15 mol/L to about 0.3 mol/L.

In some aspects, the equivalent ratio of compound (iii) to compound (iv) is 1:1.01, about 1:1.05, about 1:1.1, about 1:1.15, about 1:1.2, about 1:1.25, about 1:1.3, about 1:1.35, about 1:1.4, about 1:1.45, or 1:1.49, and any range constructed therefrom, such as from about 1:1.01 to 1:1.49, from about 1:1.05 to about 1:1.4, from about 1:1.1 to about 1:1.3, or about 1:1.15.

In some aspects, the equivalent ratio of compound (iii) to base may be about 1:1.5, about 1:2, about 1:2.5, about 1:3, about 1:3.5, about 1:4, about 1:4.5, about 1:5, or greater, and any range constructed therefrom, such as from about 1:1.5 to about 1:5, from about 1:2 to about 1:4, or from about 1:2.5 to about 1:3.5.

In some aspects, the equivalent ratio of compound (iii) to catalyst may be about 50:1, about 100:1, about 150:1, about 200:1, about 250:1 or about 300:1, and any range constructed therefrom, such as from about 50:1 to about 300:1, or from about 150:1 to about 250:1. Alternatively stated, the palladium catalyst content based on compound (iii) is about 2 mol %, about 1 mol %, about 0.75 mol %, about 0.5 mol %, about 0.25 mol %, and any range constructed therefrom, such as from about 2 mol % to about 0.25 mol %, from about 1 mol % to about 0.25 mol %, or from about 0.75 mol % to about 0.25 mol %.

In some aspects, the reaction temperature may vary with the identity of the solvent and of the reactants and reagents, and the concentrations thereof. In some aspects, the reaction temperature may be the reflux temperature of the reaction mixture. In some other aspects, the reaction temperature may be below the reflux temperature, such as about 50° C., about 55° C., about 60° C., about 65° C., about 70° C., about 75° C., or about 80° C., and any range constructed therefrom, such as from about 50° C. to about 80° C., from about 55° C. to about 75° C., or from about 55° C. to 65° C.

The reaction time may vary with the solvent, the concentration of compounds (iii) and (iv), the base, and the catalyst, and the reaction temperature. Non-limiting examples of typical reaction times are 1 hour, 2 hours, 3 hours, 4 hours, 5 hours or 6 hours.

The reaction may be monitored for completion by suitable in-process testing methods known in the art, such as by high pressure liquid chromatography ("HPLC") or infrared spectroscopy.

Catalysts within the scope of the present disclosure include transition metal catalysts such as palladium, platinum, gold, ruthenium, rhodium, and iridium catalysts. In some aspects, the coupling reaction catalyst is a palladium catalyst. In some such aspects, the palladium catalyst is a zero valent, Pd(0), catalyst.

In some aspects, the palladium catalyst is selected from the group consisting of: $[PdCl(X)]_2$ where X is allyl, cinnamyl or crotyl; $[Pd(X)PR^7]$ where $R^7$ is alkyl or aryl; [Pd(X)(Y)] where X is allyl, cinnamyl or crotyl, Y is cyclopentandienyl or p-cymyl; $Pd(dba)_2$; $Pd_2(dba)_3$; $Pd(OAc)_2$; $PdZ_2$ where Z is Cl, Br or I; $Pd_2Z_2(PR^8)_2$ where Z is Cl, Br or I, and $R^8$ is alkyl or aryl; and PdPd(TFA)2, each catalyst in combination with a phosphine ligand, a base, or a combination thereof.

In some aspects, the catalyst is selected from the group consisting of: $Pd(dppf)C_{12}$, $Pd(dppe)Cl_2$, $Pd(PCy_3)_2Cl_2$, $Pd(PPh_3)_2Cl_2$, $Pd(OAc)_2(PPh_3)_2$, $Pd(PPh_3)_4$, $Pd(PPh_3)_4Cl_2$, $Pd(PCy_3)_2$, $Pd(PCy_3)_2Cl_2$, and $Pd(t\text{-}Bu_3P)_2$. In some such aspects, the catalyst is $Pd(dppf)Cl_2$.

The catalyst may optionally be a complex with a solvent. Non-limiting examples of such complexing solvents include dichloromethane, chloroform, and acetonitrile.

The coupling reaction solvent may suitably be a non-polar solvent (e.g., methyl tert-butyl ether, diethyl ether, toluene, benzene, 1,4-dioxane, carbon tetrachloride, chloroform or dichloromethane), a polar aprotic solvent (e.g., tetrahydrofuran, methyl-tetrahydrofuran, ethyl acetate, propyl acetate, acetone, dimethylsulfoxide, N,N-dimethylformamide, acetonitrile, N,N-dimethylacetamide, N-methylpyrrolidone, hexamethylphosphoramide, or propylene carbonate), or a polar protic solvent (e.g., methanol, ethanol, 1-propanol, 2-propanol, 1-butanol, formic acid, nitromethane and acetic acid). In some aspects, the solvent may be a combination of a polar organic solvent and water. In some aspects, the solvent is a cyclic ether, a dioxane, toluene, acetonitrile, ethyl acetate, isopropyl acetate, n-propyl acetate, dimethylformamide, dimethyl sulfoxide, or combinations thereof. In some aspects, the solvent is a cyclic ether. In some aspects, the solvent is tetrahydrofuran or methyl-tetrahydrofuran. In some aspects, the solvent is tetrahydrofuran and water.

The base for the coupling reaction may suitably be a carbonate, a phosphate, a tertiary amine, a cyclic amidine, or a guanidine. In some such aspects, the base is a carbonate, or an alkali metal carbonate such as sodium carbonate or potassium carbonate. The mole ratio of base to compound (iii) is about 1.5:1, about 2:1, about 2.5:1, about 3:1, about 3.5:1, about 4:1, about 4.5:1, or about 5:1, and any range constructed therefrom, such as from about 1.5:1 to about 5:1, from about 2:1 to about 4:1, or from about 2.5:1 to about 3.5:1.

The coupling reaction may optionally comprise a step for scavenging the catalyst from the reaction product mixture comprising compound (v) by the addition of at least one added metal catalyst scavenger. Non-limiting examples of scavengers include a thiol, a thiourea, a thiocarbamate, and a xanthate, or a salt thereof. In some such aspects, the catalyst scavenger is a thiol. In one aspect, the catalyst scavenger is N-acetylcysteine. The equivalents of scavenger may vary with the catalyst per se and the equivalents thereof. Typically, about 5, 10, 15, 20, 25, 30, 35, 40, 45 or 50 equivalents of scavenger per equivalent of catalyst may be used.

In some aspects, where compound (v) is in solution in the reaction product mixture, the process further comprises precipitation of compound (v) therefrom to form a slurry or suspension of compound (v) by addition of at least one anti-solvent thereto. In some such aspects, the anti-solvent is a non-polar solvent. In some such aspects, the anti-solvent is n-heptane. Anti-solvent may be added with mixing at the reaction temperature or at a reduced temperature. In some aspects, anti-solvent addition may be done after separation of the reaction product mixture phases. In some aspects, anti-solvent addition may be to the reaction product mixture in the absence of prior phase separation. In some aspects, seed crystals of compound (v) may be added prior to anti-solvent addition. After anti-solvent addition, the reaction product mixture may be cooled with mixing and aged at temperature to generate a slurry of compound (v). Cooling may be to about room temperature or lower, such as about 20° C., about 15° C., about 10° C., about 5° C., or less. In such aspects, solid compound (v) may be isolated by methods known in the art, such as filtration and/or centrifugation. Solid compound (v) may be optionally washed after isolation. Washing may be done with the reaction solvent, the anti-solvent, or with a solvent in which compound (v) is poorly soluble. Solid compound (v) may be dried by methods known in the art, such as under reduced pressure.

Compound (v) supplemental purification steps are within the scope of the present disclosure. For instance, and without limitation: reaction product mixture solvent exchange; compound (v) solution washing; extraction; precipitation, isolation and washing; chromatographic purification such as HPLC, ion exchange, or exclusion; and combinations thereof.

In some aspects, the step for preparing compound (v) is done in the absence of a supplemental purification step as described elsewhere herein. In some such aspects, the step for preparing compound (v) is done in the absence of a chromatographic purification step, solvent exchange step, or a combination thereof.

The yield of compound (v) is at least 65%, at least 70%, at least 75%, at least 80%, at least 85%, or at least 90%. The purity of compound (v) by HPLC is at least 98 area %, at least 98.5 area %, at least 99 area %, or at least 99.5 area %, such as 99 area %, 99.1 area %, 99.2 area %, 99.3 area %, 99.4 area %, 99.5 area %, 99.6 area %, or 99.7 area %.

Among other advantages, as compared to prior art processes, the step for preparing compound (v) allows for replacement of acetonitrile with tetrahydrofuran that is less toxic and less expensive, allows for the reduction of catalyst loading, allows for reduced reaction temperature, allows for the elimination of chromatographic purification steps, and (v) while maintaining or improving yield and providing for high purity. In embodiments, the disclosed process for preparing compound (v) allows for at least a ten-fold reduction of catalyst loading. In embodiments, the disclosed process for preparing compound (v) allows for reduction of reaction temperature by at least 50° C.

In some aspects, compounds (iii), (iv) and (v) are the following structures:

(iii)

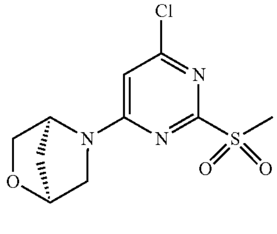

;

-continued (iv)

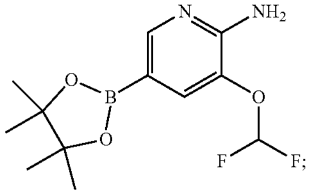

and (v)

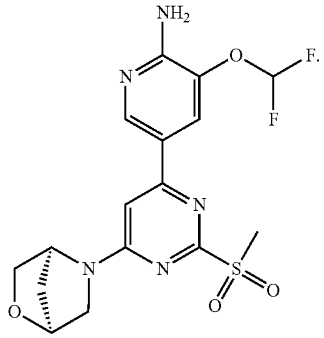 [SMILES: CS(=O)(=O)c1nc(-c2cnc(N)c(OC(F)F)c2)cc(N2C[C@@H]3C[C@H]2CO3)n1]

Preparation of Compound Formula I from Compounds (v) and (vi)

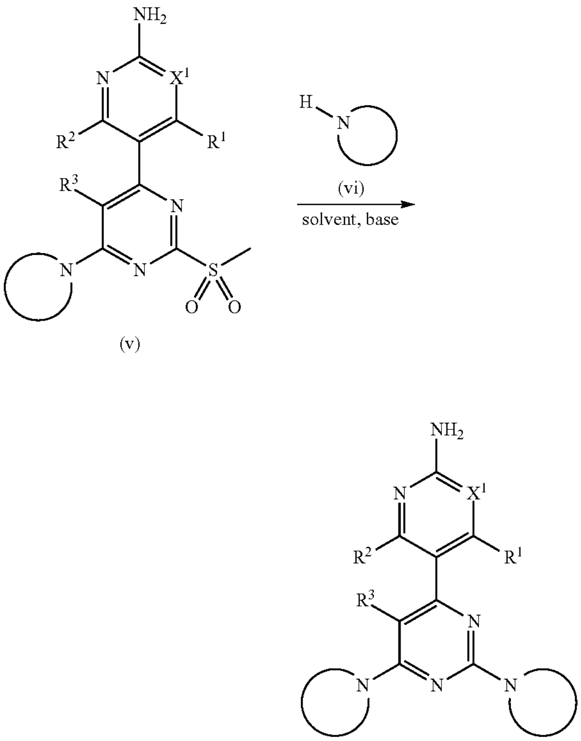

(v)

I

The disclosed processes include forming a reaction mixture from the solvent, compound (v), a stoichiometric excess of compound (vi), and the base. In some aspects, the reaction mixture is a suspension. In some aspects, the reaction mixture is an emulsion. The reaction mixture is heated to a reaction temperature with mixing and is held at the reaction temperature with mixing for a time sufficient to reach a desired conversion thereby forming a reaction product mixture comprising a compound of formula I. In some aspects, compound I is in solution in the reaction product mixture. In-process testing for the percentage of unreacted compound (v) may be done to evaluate the degree of conversion.

In some aspects, the concentration of compound (v) in the reaction mixture may suitably be about 50 g/L, about 100 g/L, about 150 g/L, about 200 g/L, about 250 g/L, about 300 g/L, about 350 g/L, or about 400 g/L, and any range constructed therefrom, such as from about 50 g/L to about 400 g/L, from about 100 g/L to about 350 g/L, or from about 200 g/L to about 300 g/L. On a mole per liter basis, the concentration may suitably be from about 0.1 mol/L, about 0.25 mol/L, about 0.5 mol/L, about 0.75 mol/L, or about 1 mol/L, and any range constructed therefrom, such as from about 0.1 mol/L to about 1 mol/L, from about 0.25 mol/L to about 0.75 mol/L, or from about 0.5 mol/L to about 0.75 mol/L.

In some aspects, the equivalent ratio of compound (v) to compound (vi) is 1:1.01, about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, or 1:2.4, and any range constructed therefrom, such as from 1:1.01 to 1:2.4, from about 1:1.1 to about 1:2, from about 1:1.2 to about 1:1.8, or from about 1:1.4 to about 1:1.6.

In some aspects, the equivalent ratio of compound (v) to base may be about 1:1.01, about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, or 1:2.4, and any range constructed therefrom, such as from 1:1.01 to 1:2.4, from about 1:1.1 to about 1:2, from about 1:1.2 to about 1:1.8, or from about 1:1.4 to about 1:1.6.

In some aspects, the reaction temperature may vary with the identity of the solvent and of the reactants and reagents, and the concentrations thereof. In some aspects, the reaction temperature may be the reflux temperature of the reaction mixture. In some other aspects, the reaction temperature may be below the reflux temperature. In any of the various aspects, the temperature is suitably about 90° C., about 95° C., about 100° C., about 105° C., about 110° C., about 115° C., about 120° C., about 125° C., about 130° C., about 135° C., about 140° C., about 145° C., about 150° C., and greater, and any range constructed therefrom, such as from about 90° C. to about 150° C., from about 100° C. to about 140° C., from about 110° C. to about 135° C., from about 115° C. to about 125° C., or from about 120° C. to about 130° C.

The reaction time may vary with the solvent, the concentration of compounds (v) and (vi), and the base. Non-limiting examples of typical reaction times are 2 hours, 5 hours, 10 hours, 15 hours, 20 hours, 24 hours, 30 hours, or 36 hours.

In some aspects, compound (vi) is of the structure:

(vi)

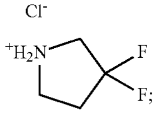

compound (v) is of the structure

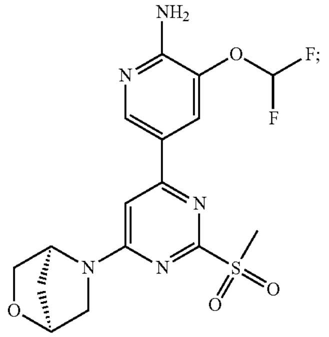

and compound 1 is of the structure:

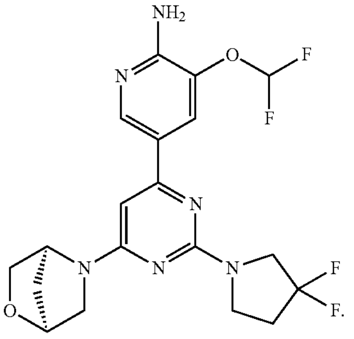

The reaction rate may be monitored for completion by suitable in-process testing methods as described elsewhere herein.

The base for the preparation of compound formula I may include any suitable base. In some aspects, the base is selected from a carbonate, a phosphate, a tertiary amine, a cyclic amidine, and a guanidine. In some such aspects, the base is a cyclic amidine. In one aspect, the base is 1,8-diazabicyclo[5.4.0]undec-7-ene (DBU), 1,1,3,3-tetramethylguanidine (TMG), or 1,5-Diazabicyclo[4.3.0]non-5-ene (DBN). In some aspects, the base is DBU or TMG. In some aspects, the base is the combination of DBU, TMG or DBN and at least one of N,N-Diisopropylethylamine ($iPr_2EtN$), trimethylamine ($Et_3N$), 1,4-diazabicyclo[2.2.2]octane (DABCO), or 2,6-lutidine.

The solvent for the preparation of compound I may suitably comprise at least one polar aprotic solvent, at least one apolar solvent, at least a solvent base or a combination thereof. In some aspects, the solvent is selected from apolar solvents such as alkylaromatic or haloaromatic solvents, secondary amine, tertiary amine, and combinations thereof. In some aspects, the solvent is selected from dimethylsulfoxide, dimethylformamide, dimethylacetamide, N-methyl-2-pyrrolidone, acetonitrile, and combinations thereof. In one aspect, the base can also function as a solvent. In such aspects, the base/solvent is a dialkylamine such as diethylamine, di-n-propylamine, di-isopropylamine, di-n-butylamine or tri-n-butylamine. In one such aspect, the base/solvent is di-n-butylamine.

In some aspects, the solvent is selected from toluene, anisole and mesitylene. In some such aspects, the solvent is mesitylene. In some aspects, the solvent is selected from the group consisting of toluene, anisole, mesitylene, diethylamine, di-n-propylamine, di-isopropylamine, di-n-butylamine, and combinations thereof. In some aspects, the solvent comprises the combination of (i) toluene, anisole, or mesitylene and (ii) a dialkylamine such as dialkylamine such as diethylamine, di-n-propylamine, di-isopropylamine, di-n-butylamine, or tri-n-butylamine. The base is DBU or DBN, or DBU or DBN in combination with an organic base such as iPr2EtN, or Et3N, and the equivalent ratio of the base to (v) is from about 1.9:1 to about 2.8:1, or from about 2.2:1 to about 2.6:1, such as about 1.9:1, about 2:1, about 2.1:1, about 2.2:1, about 2.3:1, about 2.4:1, about 2.5:1, about 2.6:1, about 2.7:1, or about 2.8:1.

In some aspects, the base is also the solvent, and is di-n-butylamine or tri-n-butylamine. In some such aspects, the base/solvent is di-n-butylamine. In such aspects, an additional base may be used. In such aspects, the additional base may be DBU or DBN, or DBU or DBN in combination with an organic base such as iPr2EtN or Et3N, and the equivalent ratio of the base to (v) is from about 1.3:1 to about 2.1:1, or from about 1.5:1 to about 1.9:1, such as about 1.3:1, about 1.4:1, about 1.5:1, about 1.6:1, about 1.7:1, about 1.8:1, about 1.9:1, about 2:1, about 2.1:1.

In some aspects, where compound I is in solution in the reaction product mixture, the process may further comprise precipitation of compound I therefrom to form a slurry or suspension of compound I by addition of at least one anti-solvent thereto. In some aspects, the anti-solvent is selected from water, alcohols, and combinations thereof. In some aspects, the anti-solvent is an alcohol. In one such aspect, the anti-solvent is n-propanol or i-propanol. Anti-solvent may be added with mixing at the reaction temperature or at a reduced temperature. After anti-solvent addition, the reaction product mixture may be cooled with mixing and aged at a suitable temperature to generate a slurry of compound formula I. For example, cooling may be to about 50° C., about 45° C., about 40° C., about 35° C., about 30° C., room temperature or lower, such as about 20° C., about 15° C., about 10° C., or about 5° C. In such aspects, solid compound I may be isolated by methods known in the art, such as filtration and/or centrifugation. Solid compound I may be optionally washed after isolation. Washing may be done with the reaction solvent, the anti-solvent, or with a solvent in which compound (v) is poorly soluble. Solid compound (v) may be dried by methods known in the art, such as under reduced pressure.

In some aspects, compound I produced by this step is an amorphous free base. In some aspects, compound I produced by this step is a crystalline free base. The crystalline form of compound I free base is identified herein as polymorph Form A. A representative XRPD pattern for polymorph Form A is shown in FIG. 1. In embodiments, a crystalline polymorph of compound I can be a crystalline polymorph Form A of compound I. The crystalline polymorph Form A can have an X-ray powder diffraction pattern comprising two or more, three or more, four or more, five or more, six or more, seven or more, eight or more, nine or more, ten or more, or all of the peaks at degrees two-theta positions of about 7.7±0.3, 12.1±0.3, 16.2±0.3, 16.4±0.3, 16.6±0.3, 17.1±0.3, 18.8±0.3, 19.4±0.3, 19.8±0.3, 20.3±0.3, 20.5±0.3, 23.3±0.3, 24.7±0.3, 25.3±0.3, and 26.5±0.3. In embodiments, the X-ray powder diffraction pattern can comprise two, three, four, or five peaks at degrees two-theta positions of about 7.7±0.3, 18.8±0.3, 19.8±0.3, 24.7±0.3, and 26.5±0.3. In embodiments, the X-ray powder diffraction pattern comprises peaks at two or more, three or more, four or more, five or more, six or more, seven or more, eight or more, nine or more, ten or more, or all of the peaks with degrees two-theta positions of about 7.7±0.3, 12.1±0.3, 16.2±0.3, 16.4±0.3, 16.6±0.3, 17.1±0.3, 18.8±0.3, 19.4±0.3, 19.8±0.3, 20.3±0.3, 20.5±0.3, 23.3±0.3, 24.7±0.3, 25.3±0.3, and 26.5±0.3. In embodiments, the X-ray powder diffraction pattern of Form A is substantially similar to the XRPD pattern illustrated in FIG. 1. In embodiments, the X-ray powder diffraction pattern of Form A is substantially similar to at least one of the XRPD patterns illustrated in FIG. 2.

Purification of compound I is within the scope of the present disclosure. For instance, and without limitation, purification by: reaction product mixture solvent exchange; solution washing; extraction; precipitation, isolation and washing; crystallization; chromatographic purification such as HPLC, ion exchange, or exclusion; and combinations thereof are contemplated in the present disclosure.

In some aspects, the step for preparing compound I is done in the absence of a supplemental chromatographic purification step, solvent exchange step, or both. In some aspects, compound I may be purified by a crystallization step as described herein.

In embodiments, the yield of compound I by the disclosed processes, based on compound (v), is at least 65%, at least 70%, or at least 75%. In embodiments, the purity of compound I by the disclosed reaction step, determined by HPLC, is at least 98 area %, at least 98.5 area %, at least 99 area %, or at least 99.5 area %.

Among other advantages, as compared to prior art processes, the step for preparing compound I allows for the reduction of the mole ratio of compound (v) to compound (vi) while maintaining or improving yield and providing for high purity. In embodiments, the reduction of the mole ratio of compound (v) to compound (vi) is less than 1:2 (e.g., about 1:1.5).

Among other advantages, as compared to prior art processes, the step for preparing compound I further allows for an increase in reactant concentration while maintaining or improving yield and providing for high purity. In some embodiments, reactant concentration increases on the order of about 3×. Among other advantages, as compared to prior art processes, purification steps may be eliminated while maintaining or improving yield and providing for high purity. Further, the present process allows for the replacement of prior art NMP solvent which is a substance of very high concern (SVHC) such that use within the European Union is subject to authorization under the REACH Regulation.

Compound I Crystallization

Compound I prepared by the processes of the present disclosure is characterized by high purity. However, further purification can be obtained by crystallization of compound I.

In any of the various aspects of the disclosure, compound I may be optionally further purified by crystallization according to the following scheme:

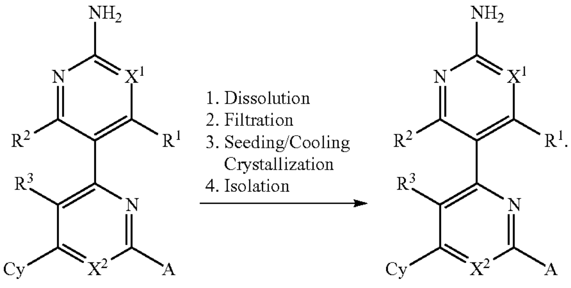

(I) (I)

The disclosed scheme includes dissolution of the compound I in a solvent, filtration of the resulting solution, seeding and cooling the solution to form crystals and isolation of the crystalized product.

In a first step, compound I, as prepared from compounds (v) and (vi), is termed crude compound I. Crude compound I is dissolved in a solvent at a temperature below the solvent boiling point to form a solution. The solvent may be a polar aprotic solvent such as a ketone. In embodiments, the solvent is acetone, methyl ethyl ketone (MEK) or methyl isobutyl ketone (MIBK). In embodiments, the solvent is MIBK. The solution has a saturation temperature that is from about 5° C. to about 10° C. less than the dissolution temperature. In embodiments, the dissolution temperature is suitably below the solvent boiling point, such as about 5° C., about 10° C., about 15° C., about 20° C., or about 25° C. below the solvent boiling point.

The solution of compound I may then be filtered through a polish filter at a temperature above the saturation temperature. Polish filters are known in the art and generally have pore size ratings of about 5 μm or less, such as about 4 μm, about 3 μm, about 2 μm, about 1 μm, about 0.5 μm or about 0.2 μm. Non-limiting examples of such filters include polytetrafluoroethylene (PTFE) membrane, sintered metal, polypropylene, nylon, and glass microfiber filters.

In some aspects, active carbon filtration may be performed prior to polish filtration. Active carbon filtration is known in the art and involves contacting a liquid mixture with activated carbon particles (e.g., powder) characterized by a porous microstructure and a large internal surface area. Certain dissolved substances, such as impurities, are primarily removed from the liquid primarily by adsorption. The active carbon may be added to a liquid mixture followed by filtration, the liquid mixture may be filtered through an active carbon bed, or a combination of those techniques can be employed. Non-limiting examples of active carbon are Norit® SX Plus, DARCO® KB, and DARCO® G-60.

Following filtration, the solution of compound I may be seeded with crystalline compound I free base, polymorph Form A. In some aspects, dry seed crystals may be used. In some aspects, seed crystals may be slurried in a solvent, such as the same solvent used for dissolving compound formula I, at a suitable temperature, such as about room temperature. The solution of compound I is cooled to below the saturation point whereupon the seed crystal slurry is added. The suspension may be optionally aged at the seed crystal addition temperature.

Seed crystals may be milled or unmilled. In some aspects, the seed crystals may be characterized by a particle size distribution. For instance, in some aspects, the diameter of a particle sphere at which 10% of the particles in the sample are smaller on a volume basis ("D(v,0.1)") is suitably about 0.5 μm, about 1 μm, about 2 μm, about 3 μm, about 4 μm, about 5 μm, about 6 μm, about 7 μm, about 8 μm, about 9 μm, about 10 μm, or greater, and any range constructed therefrom, such as from about 0.5 μm to about 10 μm, from about 1 μm to about 8 μm, or from about 1 μm to about 5 μm. In some aspects, the diameter of a particle sphere at which 50% of the particles in the sample are smaller on a volume basis ("D(v,0.5)") is suitably about 2 μm, about 4 μm, about 10 μm, about 15 μm, about 20 μm, about 25 μm, or greater, and any range constructed therefrom, such as from about 2 μm to about 25 μm, from about 4 μm to about 20 μm, from about 4 μm to about 15 μm, or from about 4 μm to about 10 μm. In some aspects, the diameter of a particle sphere at which 90% of the particles in the sample are smaller on a volume basis ("D(v,0.9)") is suitably about 5 μm, about 10

μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, or greater, and any range constructed therefrom, such as from about 5 μm to about 100 μm, from about 10 μm to about 80 μm, from about 10 μm to about 30 μm, or from about 60 μm to about 80 μm. In some aspects, seed loading may suitably be about 0.1 wt. %, about 0.25 wt. %, about 0.5 wt. %, about 0.75 wt. %, about 1 wt. %, about 1.5 wt. %, about 2 wt. %, about 2.5 wt. %, about 3 wt. %, about 3.5 wt. %, or about 4 wt. % or greater, and any range constructed therefrom, such as from about 0.1 wt. % to about 4 wt. %, about 1 wt. % to about 3 wt. %, or about 1.5 wt. % to about 2.5 wt. %. In some aspects, seed crystal particle size, particle size range, and loading outside of the above-exemplified values and ranges are possible in order to provide for crystallized compound I in a desired particle size range.

The suspension may then be cooled with agitation to a final crystallization temperature. The final temperature is generally less than 20° C., such as about 15° C., about 10° C., about 5° C., about 0° C., about −5° C., about −10° C., about −15° C., or even lower. The cooling rate may suitably be about 5° K/hour, about 7.5° K/hour, about 10° K/hour, about 12.5° K/hour, about 15° K/hour, about 17.5° K/hour, about 20° K/hour, or greater. Aging time at final temperature may suitably be about 1 hour, about 2 hours, about 3 hours, about 4 hours, about 5 hours, about 6 hours, about 7 hours, about 8 hours, about 9 hours, about 10 hours, or more.

Crystallized solid compound I may be isolated by methods known in the art, such as filtration and/or centrifugation. Solid compound I may be optionally washed after isolation. Washing may be done with chilled dissolution solvent or a solvent that is considered to be non-reactive with compound formula I. In some aspects, the non-reactive solvent is an alcohol, such as, for instance, i-propanol, ethanol or methanol. Sequential washing may be done with the dissolution solvent and with an alcohol. Solid compound I may be dried by methods known in the art, such as under reduced pressure.

In some aspects, crystallized compound I may be milled using any suitable milling process such as an impact mill, a hammer mill, an air mill, or a jet mill to achieve a suitable particle size. In some aspects, crystallized compound I undergoes impact milling to achieve a D(v,0.1) particle size of about 2 μm, about 4 μm, about 6 μm, about 8 μm, about 10 μm, about 12 μm, about 14 μm, about 16 μm, about 18 μm, about 20 μm, about 25 μm, about 30 μm, or greater, and any range constructed therefrom, such as from about 2 μm to about 30 μm, from about 2 μm to about 20 μm, or from about 4 μm to about 14 μm. In such aspects, crystallized compound I undergoes impact milling to achieve a D(v,0.5) particle size of about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, or greater, and any range constructed therefrom, such as from about 5 μm to about 70 μm, from about 10 μm to about 60 μm, from about 10 μm to about 30 μm, from about 10 μm to about 20 μm, from about 30 μm to about 70 μm, or from about 40 μm to about 60 μm. In such aspects, crystallized compound I undergoes impact milling to achieve a D(v,0.9) particle size of about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, or greater, and any range constructed therefrom, such as from about 30 μm to about 200 μm, from about 40 μm to about 150 μm, from about 40 μm to about 100 μm, from about 40 μm to about 80 μm, or from about 100 μm to about 160 μm. In some aspects, compound I particle size ranges outside of the above-exemplified values and ranges are possible.

Crystallized compound I may be characterized analytically. For instance, in some aspects: water content by Karl Fischer may be less than 0.1 wt. %; heavy metal content, such as for instance by inductively coupled plasma mass spectrometry ("ICP-MS"), may be less than 20 ppm; the total of all organic impurities by HPLC may be less than 0.1 area % or less than 0.05 area %; purity by HPLC may be at least 98 area %, at least 98.5 area %, at least 99 area %, at least 99.5 area %, at least 99.8 area %, 99.9 area %, or 100 area %. The yield of compound I in the crystallization step is at least 80%, at least 85%, or at least 90%.

Crystalline compound I is a free base. In some aspects, the crystals may be characterized as having a needle/rod morphology. In some aspects, the crystals may be characterized as having a prismatic morphology. In some aspects, the crystals are polymorph Form A.

In some such aspects, compound I is the species 5-(6-((1S,4S)-2-oxa-5-azabicyclo[2.2.1]heptan-5-yl)-2-(3,3-difluoropyrrolidin-1-yl)pyrimidin-4-yl)-3-(difluoromethoxy)pyridin-2-amine of the structure and designated as compound 1:

1

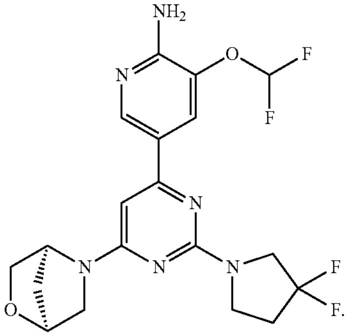 [SMILES: Nc1ncc(-c2cc(N3C[C@@H]4C[C@H]3CO4)nc(N3CCC(F)(F)C3)n2)cc1OC(F)F]

In one aspect, the dissolution solvent is MIBK. The solubility of compound I free base in MIBK is about 8.2 wt. % at 90° C., about 5.2 wt. % at 80° C., about 4 wt. % at 70° C., about 3 wt. % at 60° C., about 2 wt. % at 50° C., about 1.4 wt. % at 40° C., about 1 wt. % at 30° C., about 0.9 wt. % at 20° C., about 0.6 wt. % at 10° C., about 0.4 wt. % at 0° C., and about 0.2 wt. % at −10° C. In some aspects, a 6.5 wt. % to 7.5 wt. % solution of compound I free base in MIBK is formed at 90° C. Following filtration at about 90° C., the solution may be cooled to about 75° C. following by addition of seed crystals to form a slurry, and optionally held (aged) at that temperature for a period of time, such as from about 0.5 to about 2 hours. The slurry may then be cooled, such as for instance to about −10° C., and aged at that temperature for a period of time, such as from about 2 to about 10 hours. Solid crystallized compound I may be isolated, and washed with chilled MIBK (e.g., at about 0° C. to about 10° C.) and then with chilled alcohol, such as ethanol (e.g., at about 0° C. to about 10° C.). Crystalline compound I may be dried at a temperature of from about 40° C. to about 70° C. (e.g., 60° C.) under vacuum (e.g., about 20 mbar or less) until a constant weight is achieved.

Preparation of Sulfone Compound (iii)

In some aspects, the process of the present disclosure further comprises preparation of sulfone compound (iii).

In one such aspect, sulfone compound (iii) may be prepared according to a first process scheme.

In a first step of the first process scheme, a halogen atom is displaced from dihalothiopyrimidine compound (i) with a 3- to 12-membered amine-containing heterocycloalkyl compound (vii) under basic conditions in a solvent to provide an alkylthio compound (ii) according to the following scheme:

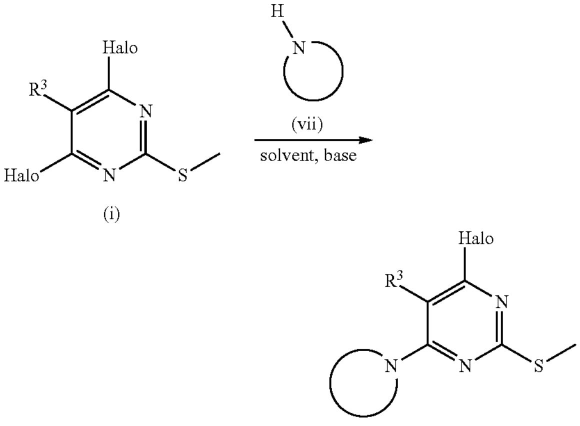

(vii) (i) (ii)

In a second step of the first process scheme, alkylthio compound (ii) is treated with at least one oxidizing agent in a solvent to provide oxidized sulfone compound (iii) according to the following scheme:

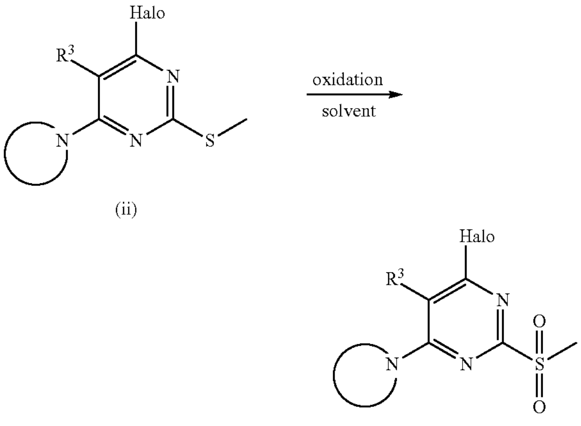

(ii) (iii)

In some aspects, the solvent for the step for preparing alkylthio compound (ii) is suitably a polar organic solvent. In some aspects, the solvent for the reaction is selected from dimethylsulfoxide, dimethylformamide, N,N-dimethylacetylamide, N-methyl-2-pyrrolidone, acetonitrile, methanol, ethanol, n-propanol, i-propanol, n-butanol, cyclohexanol, tetrahydrofuran, 2-Me-tetrahydrofuran, ethyl acetate, n-propyl acetate, i-propyl acetate, and mixtures thereof. In some such aspects, the solvent is an alcohol. In some such aspects, the solvent is selected from dimethylsulfoxide, acetonitrile, methanol, and ethanol. In some aspects, the solvent is methanol or ethanol. In some aspects, the solvent is ethanol.

In some aspects, the base is selected from a carbonate, a hydrogencarbonate, a phosphate, an tertiary amine, and a cyclic amidine. In some such aspects, the base is a tertiary amine. In some such aspects, the base is $iPr_2EtN$ or $Et_3N$. In some such aspects, the base is $Et_3N$. In some aspects, the equivalents of base to compound (vii) is about 1.5:1, about 2:1, about 2.1:1, about 2.2:1, about 2.3:1, about 2.4:1, about 2.5:1, about 2.6:1, about 2.7:1, about 2.8:1, about 2.9:1, about 3:1, about 3.5:1, or about 4:1, and any range constructed therefrom, such as from about 1.5:1 to about 4:1, from about 1.5:1 to about 3:1, from about 2:1 to about 3:1, or from about 2.2:1 to about 2.6:1.

In some aspects, the concentration of compound (i) in the reaction mixture may suitably be about 25 g/L, about 50 g/L, about 75 g/L, about 100 g/L, about 125 g/L, about 150 g/L, about 175 g/L or about 200 g/L, and any range constructed therefrom, such as from about 25 g/L to about 200 g/L, from about 50 g/L to about 175 g/L, or from about 75 g/L to about 125 g/L. On a mole per liter basis, the concentration may suitably be about 0.1 mol/L, about 0.15 mol/L, about 0.2 mol/L, about 0.25 mol/L, about 0.3 mol/L, about 0.35 mol/L, about 0.4 mol/L, about 0.45 mol/L, about 0.5 mol/L, about 0.55 mol/L, about 0.6 mol/L, about 0.65 mol/L, about 0.7 mol/L, about 0.75 mol/L, about 0.8 mol/L, about 0.85 mol/L, about 0.9 mol/L, about 0.95 mol/L, or about 1 mol/L, and any range constructed therefrom, such as from about 0.1 mol/L to about 1 mol/L, from about 0.2 mol/L to about 0.75 mol/L, or from about 0.4 mol/L to about 0.75 mol/L.

The mole ratio of compound (i) to compound (vii) is suitably about 1:1.01, about 1:1.05, about 1:1.1, about 1:1.11, about 1:1.12, about 1:1.13, about 1:1.14, about 1:1.15, about 1:1.2, about 1:1.25, about 1:1.3, about 1:1.35, about 1:1.4, about 1:1.45, or about 1:1.5, and any range constructed therefrom, such as from 1:1.01 to 1:1.5, from 1:05 to 1:1.3, or from 1:10 to 1:1.14. The mole ratio of the compound (i) to the base is suitably about 1:1.5, about 1:2, about 1:2.1, about 1:2.2, about 1:2.3, about 1:2.4, about 1:2.5, about 1:2.6. about 1:2.7, about 1:2.8, about 1:2.9, or about 1:3, and any range constructed therefrom, such as from about 1:1.5 to about 1:3, from about 1:2 to about 1:2.8, or from about 1:2.2 to about 1:2.6.

The reaction temperature is suitably about 10° C., about 15° C., about 20° C., about 25° C., about 30° C., about 35° C., about 40° C., about 45° C., about 50° C., about 60° C., about 65° C., about 70° C., or about 75° C., and any range constructed therefrom, such as from about 10° C. to about 75° C., from about 20° C. to about 70° C., from about 25° C. to about 60° C., from about 25° C. to about 50° C., or from about 30° C. to about 40° C. The base may be added over a time period, such as from about 0.5 to about 4 hours. The reaction mixture may suitably be aged for a period of time at reaction temperature to complete the reaction and form the reaction product mixture containing compound (ii).

In some aspects, compound (ii) precipitates from solution in the reaction product mixture upon formation thereof. In some such aspects, water may be added to cooled reaction product mixture to dissolve water soluble salts. Precipitated compound (ii) may be isolated by drying or centrifugation, and optionally washed. In some aspects, compound (ii) may be washed with chilled alcohol (e.g., methanol or ethanol), chilled water, or a combination thereof. Isolated compound (ii) may be dried.

In some aspects, the step for preparing compound (ii) is done in the absence of a supplemental purification step as described elsewhere herein. In some such aspects, the step for preparing compound (ii) is done in the absence of a chromatographic purification step, solvent exchange step, or a combination thereof. Advantageously, the present process for preparing compound (ii) may suitably be done in an alcoholic solvent such as ethanol thereby allowing for the elimination of certain solvents identified as SVHC, such as DMF, used in prior art processes.

The yield of compound (ii), based on compound (i), is at least 80%, at least 85%, at least 90%, or at least 94%. The purity of compound (ii) by HPLC is at least 98 area %, at least 98.5 area %, at least 99 area %, at least 99.5 area %, or at least 99.9 area %.

Among other advantages, as compared to prior art processes, the first step of the first process scheme for preparing compound (ii) allows for replacement of toxic solvents (e.g., dimethylformamide) with a less toxic solvent, and allows for the elimination of a chromatography step, while maintaining or improving yield and providing for high purity.

In the second step for preparing compound (iii) according to the first process scheme, in some aspects, the solvent is suitably a polar organic solvent. In some aspects, the solvent may be a combination of a polar organic solvent and water. In some aspects, the solvent is selected from dimethylsulfoxide, dimethylformamide, N,N-dimethylacetylamide, N-methyl-2-pyrrolidone, acetonitrile, methanol, ethanol, n-propanol, i-propanol, n-butanol, cyclohexanol, hexane, toluene, tetrahydrofuran, 2-Me-tetrahydrofuran, ethyl acetate, n-propyl acetate, i-propyl acetate, and mixtures thereof. In some such aspects, the solvent is an alcohol. In some such aspects, the solvent is methanol or ethanol, optionally in further combination with water. When present in combination with water, the volume ratio of organic solvent to water is suitably about 10:1, 5:1, about 4:1, about 3:1, about 2:1, about 1:1, about 1:2, about 1:3, about 1:4, about 1:5, or about 1:10. In some particular aspects the ratio of water to methanol or ethanol is about 5:1, about 2:1, about 1:1 about 1:2 or about 1:5.

The concentration of compound (ii) in the reaction mixture is suitably about 10 g/L, about 25 g/L, about 50 g/L, about 75 g/L, about 100 g/L, or about 125 g/L, and any range constructed therefrom, such as from about 10 g/L to about 125 g/L, from about 25 g/L to about 100 g/L, or from about 50 g/L to about 75 g/L. On a mole per liter basis, the concentration may suitably be about 0.05 mol/L, about 0.1 mol/L, about 0.15 mol/L, about 0.2 mol/L, about 0.25 mol/L, about 0.3 mol/L, about 0.35 mol/L, about 0.4 mol/L, about 0.45 mol/L, or about 0.5 mol/L, and any range constructed therefrom, such as from about 0.05 mol/L to about 0.5 mol/L, from about 0.1 mol/L to about 0.4 mol/L, or from about 0.2 mol/L to about 0.3 mol/L.

The at least one oxidizing agent may be selected from peracid or its salt, peroxide, peroxysulfuric acid or its salt, a hypochloride, a tungstate, a molybdate, and combinations thereof. In some aspects, the oxidizing agent may be a tungstate, such as sodium tungstate dihydrate. In some aspects, the oxidizing agent is a peroxide, such as hydrogen peroxide. In some aspects, the oxidizing agent is the combination of a tungstate and a peroxide, such as sodium tungstate dihydrate and hydrogen peroxide. Metal-based oxidizing agents (catalyst) (e.g., a tungstate or a molybdate) may be considered to be oxidation catalysts. In the case of metal-based oxidizing agents, the content, based on compound (ii) content on a molar basis, may suitably be about 0.25 mol %, about 0.5 mol %, about 0.75 mol %, about 1 mol %, about 1.25 mol %, about 1.5 mol %, about 1.75 mol %, about 2 mol %, about 2.5 mol %, about 3 mol %, about 3.5 mol %, about 4 mol %, about 4.5 mol %, about 5 mol %, about 5.5 mol %, about 6 mol %, about 6.5 mol %, about 7 mol % or about 7.5 mol %, and any range constructed therefrom, such as from about 0.25 mol % to about 7.5 mol %, from about 0.25 mol % to about 5 mol %, from about 0.25 mol % to about 2 mol %, from about 0.5 mol % to about 1.5 mol %, or from about 0.75 mol % to about 1.25 mol %. In the case of other oxidizing agents (e.g., a peroxide), the equivalent ratio of compound (ii) to oxidizing agent is suitably about 1:1.5, about 1:2, about 1:2.1, about 1:2.2, about 1:2.3, about 1:2.4, about 1:2.5, about 1:2.6, about 1:2.7, about 1:2.8, about 1:2.9, or about 1:3, and any range constructed therefrom, such as from about 1:1.5 to about 1:3, from about 1:2 to about 1:2.8, or from about 1:2.2 to about 1:2.6.

The reaction temperature is suitably about 30° C., about 35° C., about 40° C., about 45° C., about 50° C., about 60° C., about 65° C., about 70° C., about 75° C., about 80° C., about 85° C., or about 90° C., and any range constructed therefrom, such as from about 30° C. to about 90° C., from about 40° C. to about 80° C., from about 50° C. to about 70° C., or from about 55° C. to about 65° C. In ethanol and water embodiments, the reaction temperature typically does not exceed 65° C.

In some aspects, compound (ii) is combined with solvent and a metal-based oxidizing agent (catalyst) with mixing to form a suspension. The suspension is heated to reaction temperature and the other oxidizing agent (e.g., a peroxide) is added at reaction temperature over a period of time, such as for instance, about 1 hour, about 2 hours, about 3 hours, about 4 hours, about 5 hours, about 6 hours, about 7 hours, or about 8 hours. The reaction mixture may suitably be aged for a period of time at reaction temperature to complete the reaction and form the reaction product mixture containing compound (iii).

In some aspects, the oxidizing agent in the reaction product mixture containing compound (iii) may be quenched. In some such aspects, the quencher is a sulfite, a hydrogensulfite, or a thiosulfate. In one aspect, the quencher is sodium bisulfite. In some aspects, the mole ratio of compound (iii) to quencher is suitably about 1.2:1, about 1.1:1, about 1:1.1, about 1:1.2.

In some aspects, compound (iii) precipitates from solution in the reaction product mixture upon formation thereof. Precipitated compound (iii) may be isolated by drying or centrifugation, and optionally washed. In some aspects, compound (iii) may be washed with chilled water. Isolated compound (iii) may be dried.

In some aspects, the step for preparing compound (iii) is done in the absence of a supplemental purification step. In some such aspects, the step for preparing compound (iii) is done in the absence of a chromatographic purification step, solvent exchange step, or a combination thereof.

The yield of sulfone compound (iii), based on compound (ii), is at least 80%, at least 85%, at least 90%, or at least 94%. The purity of sulfone compound (iii) by HPLC is at least 98 area %, at least 98.5 area %, at least 99 area %, at least 99.5 area %, or at least 99.9 area %.

Among other advantages, as compared to prior art processes, the second step of the first process scheme for preparing compound (iii): allows for replacement of toxic solvents (e.g., dichloromethane) with less toxic solvents that are ecologically more benign; allows for the replacement of toxic oxidizing agents (e.g., meta-chloroperoxybenzoic acid) with less toxic and safer oxidizing agents that can be used in solvent systems comprising water; avoids the generation of toxic byproducts such as chlorobenzoic acid; allows for reactant concentration increase; and allows for the elimination of a solvent stripping step, while maintaining or improving yield and providing for high purity.

In some aspects, compounds (i), (vii), (ii), and (iii) are as follows:

(i)

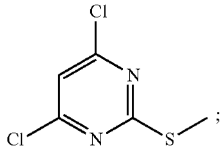
;

(vii)

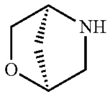
HCl;

(ii)

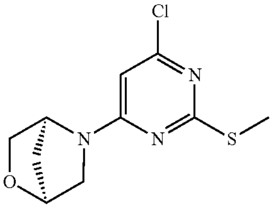
; and (iii)

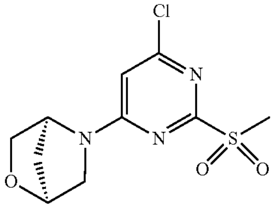

In another such aspect, sulfone compound (iii) may be prepared according to a second process scheme.

In a first step of the second process scheme, an alkylthio compound (i) is treated with at least one oxidizing agent in a solvent to provide a mixture of oxidized sulfone compound (viii) according to the following scheme:

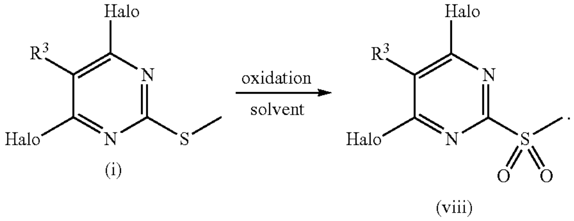

In a second step of the second process scheme, a halogen atom is displaced from sulfone compound (viii) with a 3- to 12-membered amine-containing heterocycloalkyl compound (vii) under basic conditions in a solvent to form a mixture of sulfone compound (iii) and regioisomer compound (iiia) according to the following scheme:

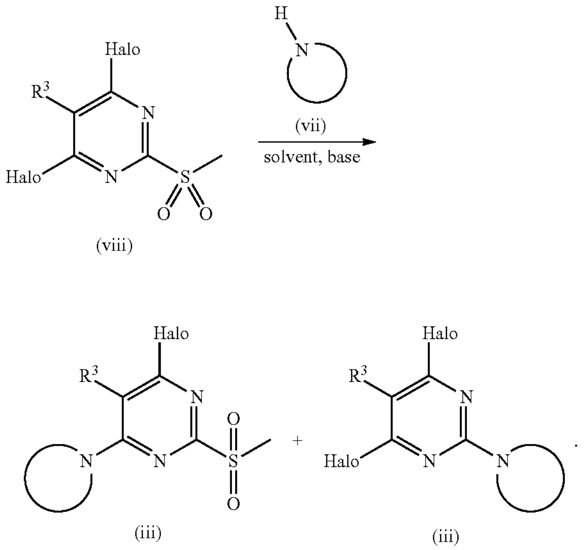

In some aspects, the solvent for forming compounds (viii), (iii) and (iiia) is a polar solvent. In some such aspects, the solvent is selected from dimethylsulfoxide, dimethylformamide, N,N-dimethylacetatamide, N-methyl-2-pyrrolidone, acetonitrile, methanol, ethanol, n-propanol, i-propanol, n-butanol, cyclohexanol, tetrahydrofuran, 2-Me-tetrahydrofuran, ethyl acetate, n-propyl acetate, i-propyl acetate, and mixtures thereof. In some aspects, the solvent is an alcohol. In some aspects, the solvent is methanol or ethanol.

The at least one oxidizing agent for forming compound (viii) is as described elsewhere herein for preparing compound (iii) from compound (ii). The content of metal-based oxidizing agents (catalysts) based on compound (i) is generally comparable with the content based on compound (ii) as described elsewhere herein. The equivalent ratio of other oxidizing agents (e.g., a peroxide) based on compound (i) is generally comparable with the equivalent ratio based on compound (ii) as described elsewhere herein.

The oxidation reaction concentration and conditions, such as temperature, reagent addition scheme, reaction time, and reaction quench for the preparation of compound (viii) are generally comparable with the reaction concentration and conditions for preparing compound (iii) from compound (ii) as described elsewhere herein.

Compound (viii) isolation and subsequent processing is generally comparable with isolation and processing steps for the preparation of compound (iii) from compound (ii).

In some aspects, the step for preparing compound (viii) is done in the absence of a supplemental purification step. In some such aspects, the step for preparing compound (viii) is done in the absence of a chromatographic purification step, solvent exchange step, or a combination thereof.

The yield of sulfone compound (viii) is at least 50%, at least 55%, at least 60%, at least 65%, or at least 70%. The purity of sulfone compound (viii) by HPLC is at least 98 area %, at least 98.5 area %, at least 99 area %, at least 99.5 area %, or at least 99.8 area %.

In another such aspect, sulfone compound (iii) may be prepared according to a third process scheme as follows:

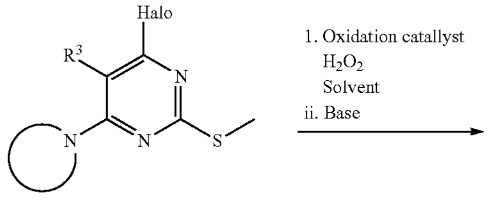

(ii)

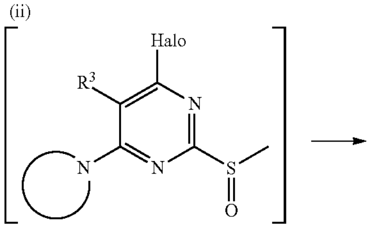

(xi)

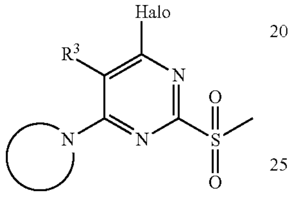

(iii)

In some aspects, the solvent for forming compounds (xi) and (iii) is a polar solvent. In some such aspects, the solvent is selected from dimethylsulfoxide, dimethylformamide, N,N-dimethylacetylamide, N-methyl-2-pyrrolidone, acetonitrile, methanol, ethanol, n-propanol, i-propanol, n-butanol, cyclohexanol, tetrahydrofuran, 2-Me-tetrahydrofuran, ethyl acetate, n-propyl acetate, i-propyl acetate, water, and mixtures thereof. In some aspects, the solvent is an alcohol and water. In some aspects, the solvent is methanol or ethanol and water, or is methanol water. The concentration of compound (ii) in the solvent is suitable about 5 wt. %, about 6 wt. %, about 7 wt. %, about 8 wt. %, about 9 wt. %, about 10 wt. %, about 11 wt. %, or about 12 wt. %, and any range constructed therefrom, such as from about 5 wt. % to about 12 wt. %, or from about 5 wt. % to about 10 wt. %.

Metal-based oxidizing agents (catalyst) (e.g., a tungstate or a molybdate) may be considered to be oxidation catalysts. In the case of metal-based oxidizing agents, the content, based on compound (ii) content on a molar basis, may suitably be about 0.25 mol %, about 0.5 mol %, about 0.75 mol %, about 1 mol %, about 1.25 mol %, about 1.5 mol %, about 1.75 mol %, about 2 mol %, about 2.5 mol %, about 3 mol %, about 3.5 mol %, about 4 mol %, about 4.5 mol %, about 5 mol %, about 5.5 mol %, about 6 mol %, about 6.5 mol %, about 7 mol % or about 7.5 mol %, and any range constructed therefrom, such as from about 0.25 mol % to about 7.5 mol %, from about 0.25 mol % to about 5 mol %, from about 0.25 mol % to about 2 mol %, from about 0.5 mol % to about 1.5 mol %, or from about 0.75 mol % to about 1.25 mol %. In some aspects, the oxidation catalyst is $Na_2WO_4 \cdot 2H_2O$. In some such aspects, $Na_2WO_4 \cdot 2H_2O$ is in methanol and water. In such aspects, the mole ratio of compound (ii) to catalyst may be about 0.005:1, about 0.01:1, about 0.02:1, about 0.03:1, about 0.04:1, or about 0.05:1, and any range constructed therefrom, such as from about 0.005:1 to about 0.05:1, from about 0.005:1 to about 0.02:1.

In some aspects, the mole ratio of $H_2O_2$ to compound (ii) is about 1.5:1, about 2:1, about 2.2:1, about 2.4:1, about 2.6:1, about 2.8:1, about 3:1, about 3.2:1, about 3.4:1, about 3.6:1, about 3.8:1, or about 4:1, and any range constructed therefrom, such as from about 2:1 to about 4:1, from about 2:1 to about 3:1, from about 2.4:1 to about 3.4:1, or from about 2.6:1 to about 3.2:1. In some aspects, the $H_2O_2$ may be added to the reaction over a period of from about 2 hours to about 10 hours, from about 3 hours to about 8 hours, or from about 4 hours to about 6 hours. In some aspects, the $H_2O_2$ can be added in two or more additions during the course of the reaction, or can be added continuously. In some aspects, about 1.5, about 2, or about 2.5 equivalents $H_2O_2$ are added within the first 3 hours of the reaction. In any of the various aspects, the $H_2O_2$ addition may be controlled to maintain $H_2O_2$ accumulation in the reactor to less than 10%, less than 5%, or less than 3%. In some such aspects, the reaction temperature is suitably about 50° C., about 55° C., about 60° C., about 65° C., or about 70° C., and any range constructed therefrom, such as from about 50° C. to about 70° C., or from about 55° C. to about 65° C. In any of the various aspects, the reaction may be aged for about 5 hours, about 10 hours, or about 15 hours. In any of the various aspects, the final residual sulfoxide intermediate is less than 1%, such as about 0.5%, about 0.4% or about 0.3%.

In some particular aspects, compound (ii) is compound 11 as disclosed elsewhere herein and compound (iii) is compound 16 as disclosed elsewhere herein and as reproduced below:

Compound 11

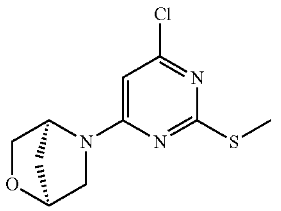

and

Compound 16

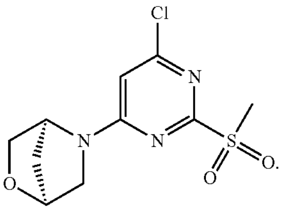

Among other advantages, as compared to prior art processes, the first step of the second process scheme for preparing compound (vii) allows for the use of relatively non-toxic and relatively environmentally benign and sustainable solvents, allows for the use of relatively non-toxic and relatively environmentally benign oxidizing agents, and allows for high reactant concentrations, while maintaining or improving yield and providing for high purity.

The second step for reacting compounds (vii) and (viii) to form compound (iii) and its regioisomer compound (iiia) generally corresponds to the reaction for reacting compounds (i) and (vii) to form compound (ii) as described elsewhere herein. More particularly, the base, mole ratio of compound (viii) to compound (vii), the mole ratio of compound (viii) to base, the concentration of compound (viii) in the reaction mixture, the reaction temperature, and the base addition scheme generally correspond to the reaction conditions for the preparation of compound (ii) as described elsewhere herein.

In some aspects, compound (iii) and regioisomer (iiia) precipitate from solution in the reaction product mixture upon formation thereof. The mole ratio of compound (iii) to compound (iiia) is from about 3:1 to about 20:1, from about 5:1 to about 15:1, or about 10:1. Based on experimental evidence to date, it is believed that the regioisomer (iiia) has significantly high solubility in the solvent mixture as compared to sulfone compound (iii). Therefore, compound (iiia) may be effectively separated from compound (iii) during the isolation and washing steps. In some such aspects therefore, water may be added to cooled reaction product mixture to dissolve water soluble salts and a disproportionate amount of regioisomer (iiia) as compared to compound (iii). The molar ratio of solid compound (iii) to solid compound (iiia) in the slurry is at least 50:1 at least 75:1, at least 90:1 or at least 95:1. Precipitated compound (iii) may be isolated by drying or centrifugation, and optionally washed. In some aspects, compound (iii) may be washed with chilled water. Isolated compound (iii) may be dried.

The reaction of compound (vii) and compound (viii) provides a yield of compound (iii), based on compound (viii), of at least 50%, at least 55%, at least 60%, at least 65%, at least 70%, or at least 75%. The purity of compound (iii) produced by such a reaction as determined by HPLC is at least 97 area %, at least 97.5 area %, at least 98 area %, at least 98.5 area %, at least 99 area %, or at least 99.5 area %.

In some aspects, the step for preparing compound (iii) from compounds (vii) and (viii) is done in the absence of a supplemental purification step. In some such aspects, the step for preparing compound (iii) is done in the absence of a chromatographic purification step, solvent exchange step, or a combination thereof.

Among other advantages, as compared to prior art processes, the first step of the process scheme for preparing compound (iii) from compounds (vii) and (viii) allows for allows for the use of relatively non-toxic and relatively environmentally benign and sustainable solvents, and avoids the need for purification step, while maintaining yield and purity.

The first and second reaction schemes for producing compound (iii) may be suitable for use for preparing a compound of formula (Ia):

(Ia)

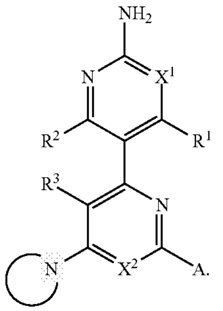

$R^1$, $R^2$, $R^3$, $X^1$, $X^2$, A and

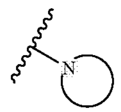

(corresponding to $C_y$) are as defined elsewhere herein.

In some aspects, compounds (i), (viii), (vii), (iii) and (iiia) are as follows:

(i)

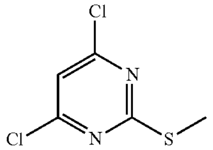

;

(viii)

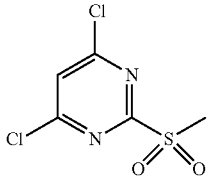

;

(vii)

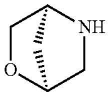

HCl;

(iii)

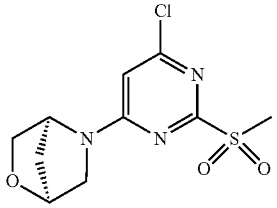

; and (iiia)

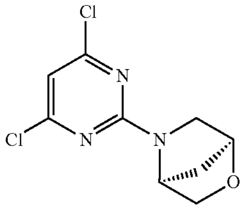

Preparation of Compound (iv) Species

In some aspects of the disclosure, a process for preparing compound (iva) is provided. The process generally proceeds according to steps A to D in the scheme detailed below.

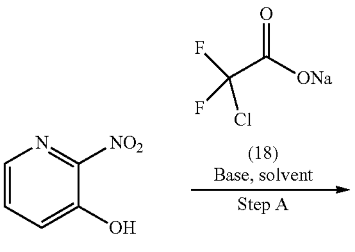

(17)

-continued

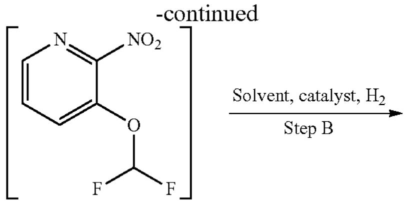

(19)

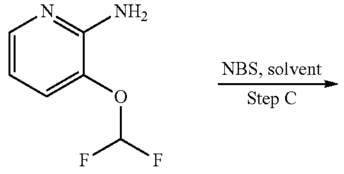

(20)

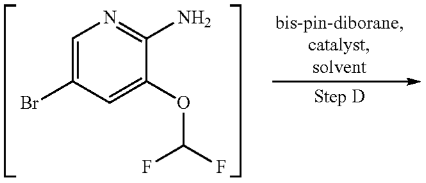

(21)

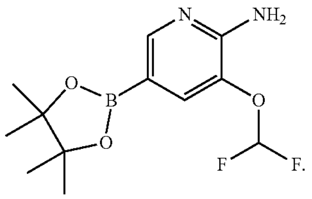

(iva)

In step A, a reaction mixture comprising 2-nitropyridin-3-ol (compound (17)), sodium 2-chloro-2,2-difluoroacetate (compound (18)), a solvent and base is formed and reacted to form a reaction product mixture comprising 3-(difluoromethoxy)-2-nitropyridine (compound (19)) in solution.

The step A solvent is suitably a polar organic solvent, or a polar aprotic solvent. One example of a suitable solvent is dimethylformamide (DMF). The base is suitably a strong base, or a strong inorganic base. One example of a suitable base is an aqueous carbonate, such as sodium carbonate or potassium carbonate. The reaction temperature may vary with the identity of the solvent. In the case of DMF, the reaction temperature may be greater than 50° C., such as about 75° C., about 90° C., about 100° C., or about 110° C.

The step A reaction product mixture may be washed with a polar organic solvent or a polar aprotic solvent. One example of a suitable solvent is ethyl acetate. The polar aprotic solvent may optionally comprise water. The reaction product mixture containing compound (19) in solution may optionally be washed with a brine solution. The reaction product mixture may optionally be concentrated prior to step B.

In step B, a reaction mixture comprising the solution of compound (19) is hydrogenated in the presence of catalyst to form a reaction product mixture comprising 3-(difluoromethoxy)pyridin-2-amine (compound (20)). Step B solvent may be a polar organic solvent or a polar aprotic solvent. One example of a suitable solvent is ethanol. The catalyst may suitably be a precious metal catalyst as described herein. One example of a catalyst is palladium on carbon. The reaction temperature may vary with the identity of the solvent. In the case of ethanol, the reaction temperature may be greater than 25° C., such as about 30° C., about 35° C., about 40° C., about 45° C., about 50° C., or greater.

The step B reaction product mixture may be optionally filtered through diatomaceous earth. A reaction product mixture solvent exchange to a polar organic solvent, such as a polar aprotic solvent may be done. One example of a suitable solvent is methyl tert-butyl ether (MTBE). Solid compound (20) may optionally be formed in the reaction product mixture by addition of an anti-solvent, such as non-polar solvent. One example of a suitable anti-solvent is n-heptane. In such aspects, solid compound (20) may be isolated by filtration or centrifugation and optionally washed.

In step C, a reaction mixture comprising compound (20), N-bromosuccinimide (NBS) and a polar aprotic solvent is reacted to form a reaction product mixture comprising 5-bromo-3-(difluoromethoxy)pyridin-2-amine (compound (21)). In some aspects, the solvent is acetonitrile (ACN). The reaction mixture is reacted at a temperature of less than 20° C., such as about 15° C., about 10° C., about 5° C., about 0° C., or less, to form a reaction product mixture comprising compound (21).

The step C reaction product mixture may be optionally washed with an aqueous acid and a solvent. The acid may suitably be a weak acid such as sodium bisulfite. The solvent may be polar organic solvent, a nonpolar solvent, or a combination thereof. In some aspects, the wash solvent is a mixture of n-heptane and ethyl acetate. The step C reaction mixture may be further optionally washed with a brine solution and filtered, such as through diatomaceous earth. The resulting reaction product mixture containing compound (21) in solution may be concentrated in an aromatic solvent, such as toluene.

In step D, a reaction mixture comprising compound (21) in solution, bis-pin-diborane, a precious metal catalyst is formed and reacted to form a reaction product mixture comprising 3-(difluoromethoxy)-5-(4,4,5,5-tetramethyl-1,3,2-dioxaborolan-2-yl)pyridin-2-amine (compound (iva)) in solution. The catalyst may suitably be a precious metal catalyst as described elsewhere herein. One example of a catalyst is PdCl2(dppf) with a triphenylphosphine ligand. The solvent may suitably be the same solvent used in step C, such as toluene. The reaction mixture may optionally comprise potassium acetate or sodium acetate. The reaction mixture is reacted at a temperature of about 50° C., about 60° C., about 70° C., about 80° C., about 90° C., about 100° C., about 110° C.

The step D reaction product mixture containing compound (iva) in solution may be filtered through diatomaceous earth, and a slurry of compound (iva) may be formed by the addition of an anti-solvent. A suitable anti-solvent is a non-polar solvent such as n-heptane. Solid compound (iva) may be isolated by filtration or centrifugation, washed and dried.

Alternatively, instead of isolation as a solid, the solution of compound (iva) may be used as a reagent in subsequent reaction steps.

In some options, step D may further comprise additional purification steps. For instance, following filtration, a solvent exchange of the reaction product mixture containing compound (iva) in solution to a polar organic solvent may be done. One example of a suitable solvent is TBME or MIBK. Aqueous maleic acid and a polar protic organic solvent may be then added and aged for a suitable period of time at a temperature of less than 20° C., such as 10° C., to form a slurry of the maleic acid salt of compound (iva). An example of a polar aprotic solvent is an alcohol, such as ethanol or methanol. The maleic acid salt of compound (iva) may be isolated by filtration or centrifugation, optionally washed with a non-polar solvent (e.g., n-heptane). Thereafter, the isolated maleic acid salt of compound (iva) may be dissolved in a solvent (e.g., toluene) and treated with a weak base (e.g., aqueous sodium bicarbonate) to form compound (iva) free base. A slurry of compound (iva) may be formed by addition of anti-solvent (e.g., n-heptane) and cooling to less than 10° C. (e.g., −10° C.). Compound (23) may be isolated by filtration or centrifugation, washed, and dried.

In some aspects, the reaction scheme for preparing compound (iva) may be used for preparing a compound of formula (Ib):

(Ib)

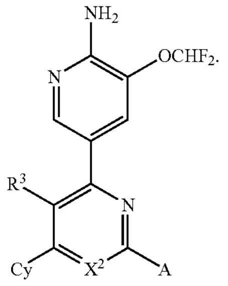

$R^3$, $X^2$, $C_y$ and A are as defined elsewhere herein.

In some aspects of the disclosure, compound (v) may be prepared according to the following first scheme:

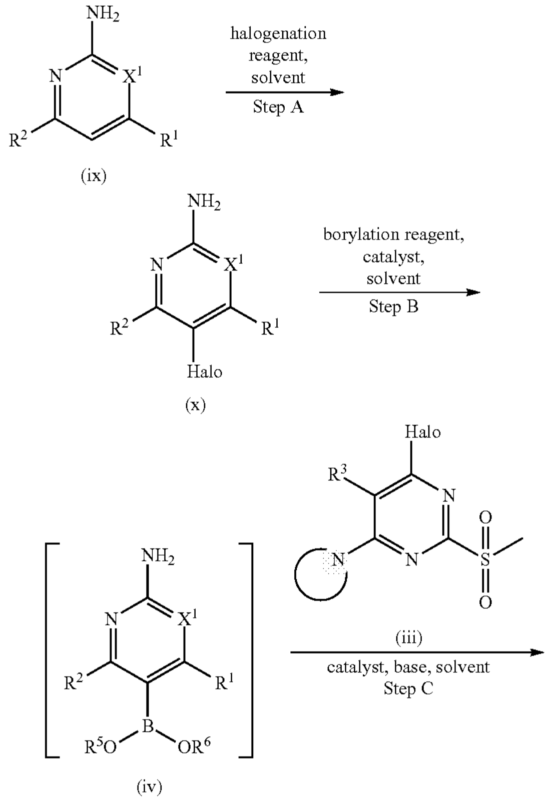

-continued

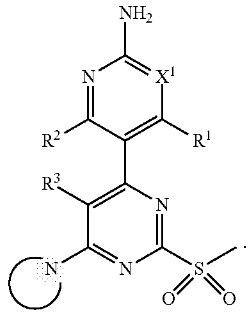

(v)

$R^1$, $R^2$, $R^3$, $R^5$, $R^6$, $X^1$, and halo are as defined elsewhere herein.

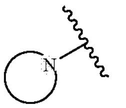 [SMILES: *N]

corresponds to Cy as defined elsewhere herein. In Step A, compound (ix) may be combined with a halogenation reagent in a solvent to form compound (x). Halogenation reagents are known in the art. Compound (x) may be isolated. In Step B, compound (x) is borylated with a borylation reagent as described herein to form a solution of compound (iv). Borylation reagents are known in the art. The borylation solvent and catalyst are as described herein. In Step C, a reaction mixture is formed comprising a solution of compound (iv), compound (iii), a catalyst, a base and a solvent. Compound (iii), the catalyst, the base, and the solvent are as described herein. Compounds (iii) and (iv) are reacted as described herein to form compound (v).

In some aspects, Steps B and C may be done in a one-pot scheme.

In some aspects, $R^1$, $R^2$ and $R^3$ are each H; $X^1$ is C—$R^4$ where $R^4$ is —O—$CHF_2$; halo is Br and the halogenation reagent is N-bromosuccinimide; the borylation reagent is bis-pin-diborane; and $R^3$ and $R^6$ together form —$C(CH_3)_2$—$C(CH_3)_2$—.

In some aspects, the first process scheme for preparing compound (v) may be used for preparing compound (Ia)

(Ia)

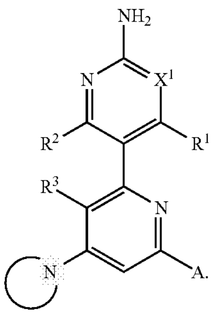

$R^1$, $R^2$, $R^3$, $X^1$, A and

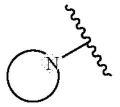 [SMILES: *N]

(corresponding to $C_y$) are as defined elsewhere herein.

In some particular aspects of the disclosure, compound (va) may be prepared according to the first scheme as follows:

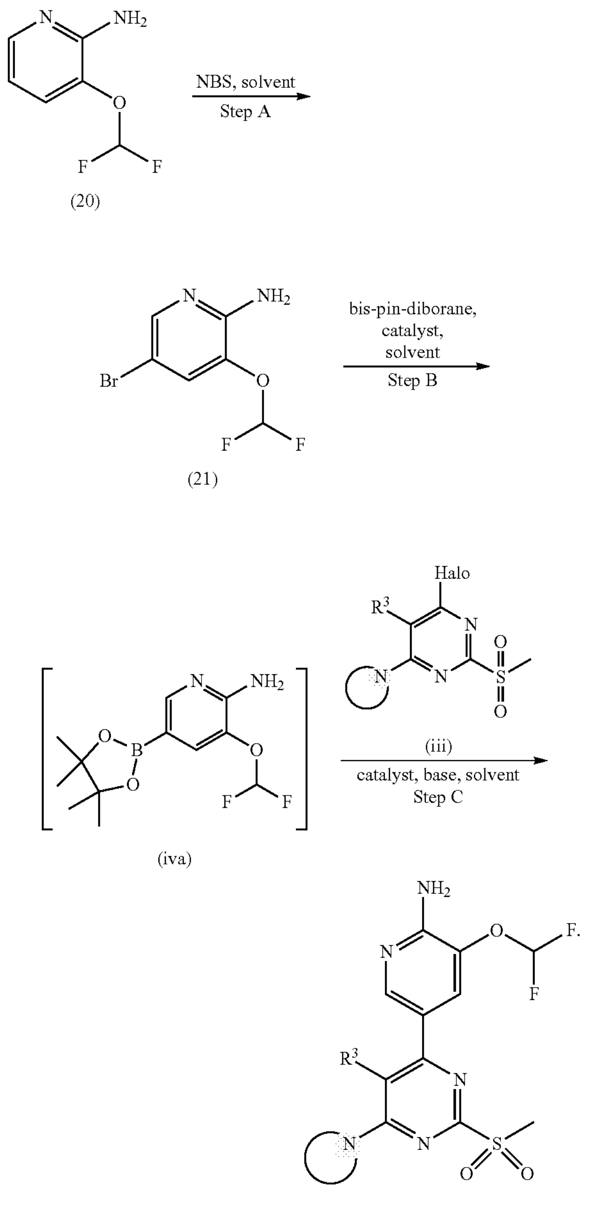

(20) (21) (iii) (iva) (va)

In some such aspects, $R^3$ is H.

In some aspects of the disclosure, compound (v) may be prepared according to the following second scheme:

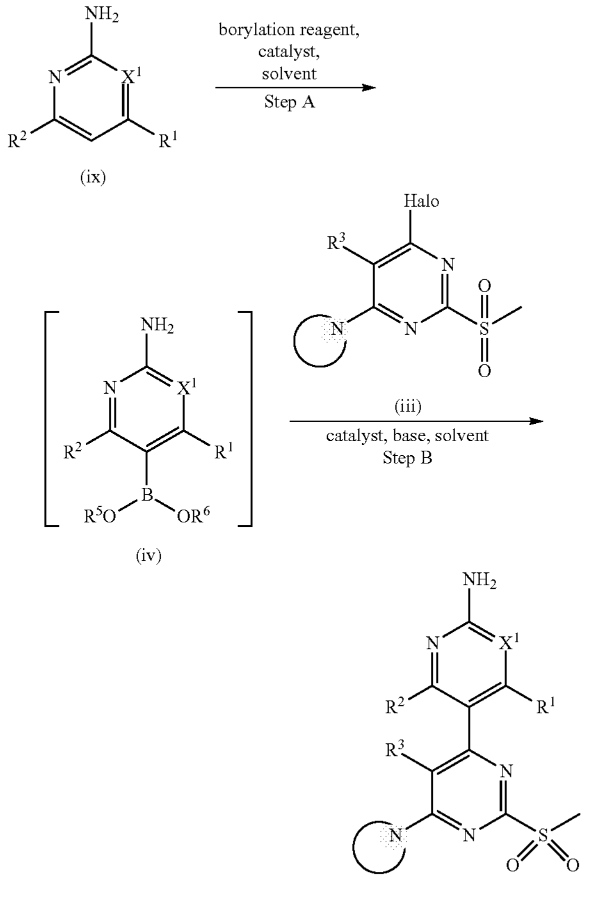

(ix) (iii) (iv)

(v)

$R^1$, $R^2$, $R^3$, $X^1$, $R^5$, $R^6$ and the borylation reagent, and are as defined elsewhere herein.

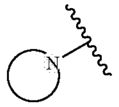

(corresponds to Cy as defined elsewhere herein. The second alternative scheme is directed to a process for preparation of compound (v) by steps A and B. In step A, compound (ix) is directly borylated with a borylation reagent to form a solution of compound (iv). The borylation solvent is as described herein. The borylation catalyst may suitably be an iridium catalyst. In Step B, a reaction mixture is formed comprising a solution of compound (iva), compound (iii), a catalyst, a base and a solvent. Compound (iii), the catalyst, the base, and the solvent are as described herein. Compounds (iii) and (iv) are reacted as described herein to form compound (v).

In some aspects, steps A and B may be done in a one-pot scheme.

In some aspects, $R^1$ and $R^2$ are each H; X is C—$R^4$ where $R^4$ is —O—$CHF_2$; the borylation reagent is bis-pin-diborane; and $R^3$ and $R^6$ together form —$C(CH_3)_2$—$C(CH_3)_2$—.

In some aspects, the second process scheme for preparing compound (v) may be used for preparing compound (I):

I

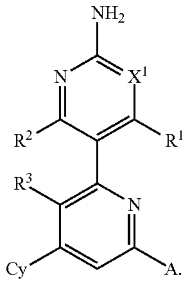

$R^1$, $R^2$, $R^3$, $X^1$, Cy and A are as defined elsewhere herein.

In some particular aspects of the disclosure, compound (va) may be prepared according to the second scheme as follows:

In some aspects of the disclosure, compound (va) may be prepared according to the following second scheme:

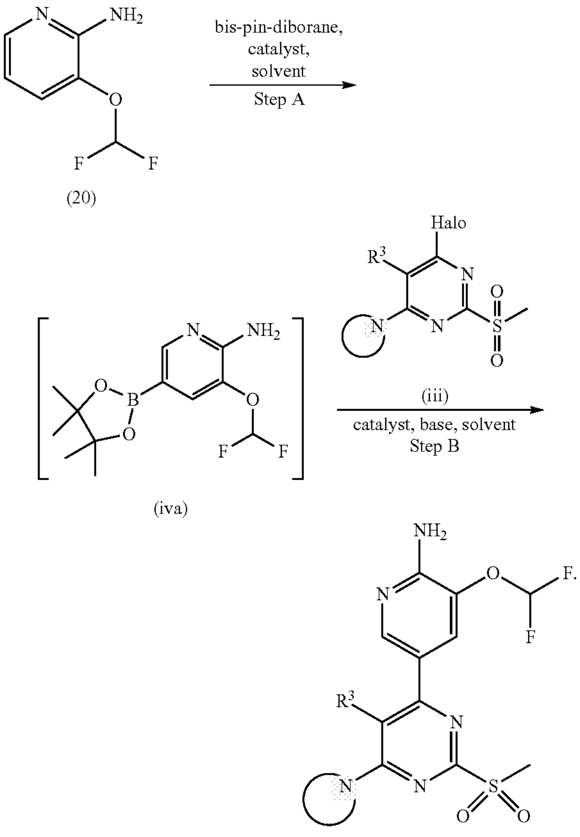

(20)

(iii)

(iva)

(va)

In some such aspects, $R^3$ is H.

In one particular aspect of the disclosure, compound 1 may be prepared by a four step process as follows.

In the first step, as described elsewhere herein, compound (vii) is reacted with compound (i) in the presence of a solvent and an organic base to form a reaction mixture comprising compound (ii) according to the following scheme

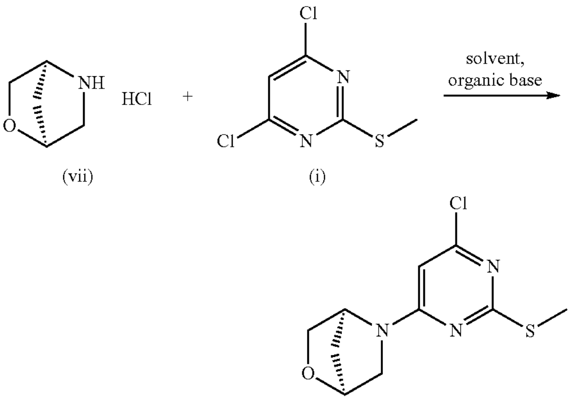

(vii) (i)

(ii)

In some aspects, the solvent is selected from the group consisting of dimethylsulfoxide, acetonitrile, and ethanol. The equivalents of organic base to compound (vii) is from about 2.2:1 to about 2.6:1, or is about 2.4:1. In some such aspects, the organic base is triethanolamine. In some such aspects, the solvent is ethanol and the reaction temperature is from about 30° C. to about 40° C.

In the second step, as described elsewhere herein, compound (ii) is oxidized with hydrogen peroxide in the presence of sodium tungstate ($Na_2WO_4$) to form a reaction product mixture comprising compound (iii) according to the following reaction scheme

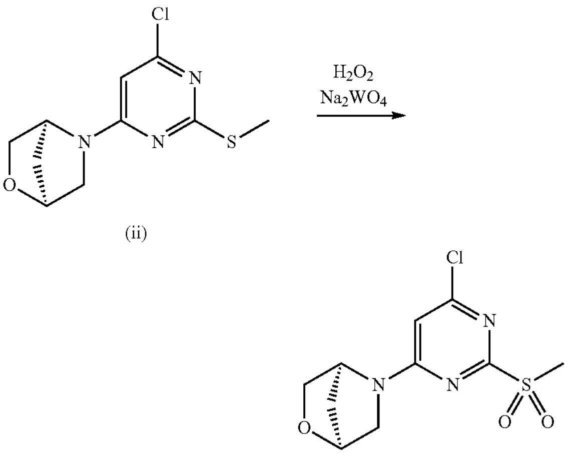

(ii)

(iii)

In some aspects, the hydrogen peroxide is added to the reaction product mixture from step (1) and the equivalent ratio of hydrogen peroxide to compound (ii) is from about 2:1 to about 3.5:1, or is about 3:1. In some aspects, the hydrogen peroxide is added over a period of from about 4 hours to about 6 hours. In some aspects, about two equivalents of hydrogen peroxide are added during a first portion of the reaction, and the remaining hydrogen peroxide is added during a second portion of the reaction.

In some aspects, the reaction temperature is from about 55° C. to about 65° C.

In some aspects, the sodium tungstate is the dihydrate. In some aspects, the $Na_2WO_4$ is $Na_2WO_4 \cdot 2H_2O$ in methanol and water.

In the third step, as described elsewhere herein, a Suzuki coupling of compound (iii) with compound (iva) is performed in the presence of an alkali metal carbonate base, a palladium catalyst, and a solvent to form a reaction product mixture compound (v). N-acetyl cysteine to the reaction product mixture to scavenge palladium. The third step reaction proceeds according to the following scheme

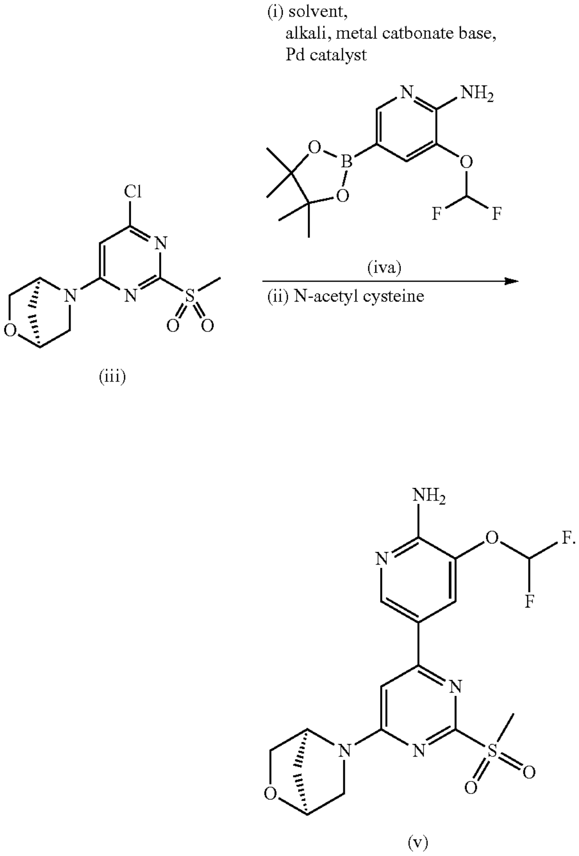 [SMILES: CS(=O)(=O)c1nc(Cl)cc(N2C[C@@H]3C[C@H]2CO3)n1 ; CC1(C)OB(c2cnc(N)c(OC(F)F)c2)OC1(C)C ; CS(=O)(=O)c1nc(-c2cnc(N)c(OC(F)F)c2)cc(N2C[C@@H]3C[C@H]2CO3)n1]

In some aspects, the solvent is tetrahydrofuran and water. In some aspects, the palladium catalyst content is about 0.5 mol % based on compound (iii). In some aspects, the palladium catalyst is $PdCl_2$(dppf). In some aspects, the equivalents of alkali metal carbonate base to compound (iii) is about 3:1, and the alkali metal carbonate base is $KCO_3$ or $NaCO_3$. In some aspects, the reaction temperature is from about 55° C. to about 65° C.

In some aspects, compound (v) is isolated from the reaction product mixture by the following order of steps: adding seed crystals to the reaction product mixture to form an admixture; adding n-heptane to the admixture; cooling the admixture to form a slurry comprising solid compound (v); and isolating solid compound (v) from the slurry.

In the fourth step, as described elsewhere herein, compound (v) is reacted with compound (vi) in the presence of at least one base, and a solvent to form a reaction product mixture comprising compound 1 according to the following reaction scheme

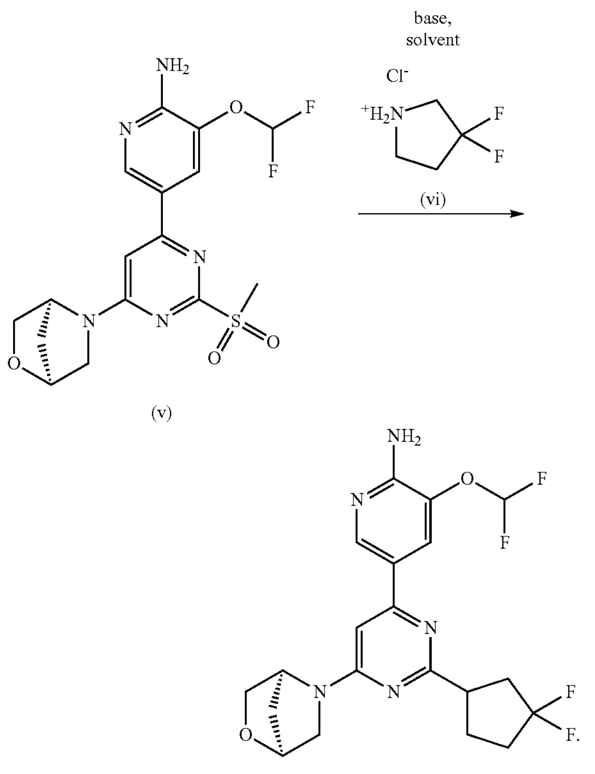

1

In some aspects, the at least one base is selected from the group consisting of 1,1,3,3-tetramethylguanidine and 1,8-diazabicyclo[5.4.0]undec-7-ene. In some aspects, the solvent is selected from the group consisting of solvent is selected from the group consisting of toluene, anisole, mesitylene, diethylamine, di-n-propylamine, di-isopropylamine, di-n-butylamine, and combinations thereof. In one such aspect, the solvent is di-n-butylamine. In some aspects, the at least one organic base further comprises a second base selected from the group consisting of 2,6-lutidine, di-isopropyl ethylamine, and 1,4-diazabicyclo[2.2.2]octane. In some aspects, the reaction temperature is from about 115° C. to about 125° C.

In some optional aspects, as described elsewhere herein, compound 1 may be isolated from the reaction product mixture by the following order of steps: adding an anti-solvent to the reaction product mixture; cooling to form a slurry comprising solid compound 1; and isolating solid compound 1. In some such aspects, the anti-solvent is selected from the group consisting of isopropanol and n-propanol. In some aspects, compound 1 may be further processed as described elsewhere herein by: forming a supersaturated solution of compound 1 and methyl isobutyl ketone; seeding the supersaturated solution with crystalline compound 1 Form A; cooling the solution to form a slurry comprising crystalline compound 1 Form A; and isolating crystalline compound 1 Form A.

In some aspects, compound 1 Form A has an X-ray powder diffraction pattern having at least two peaks at positions selected from the group consisting of 7.7±0.3 (°2θ), 12.1±0.3 (°2θ), 16.2±0.3 (°2θ), 16.4±0.3 (°2θ), 16.6±0.3 (°2θ), 17.1±0.3 (°2θ), 18.8±0.3 (°2θ), 19.4±0.3 (°2θ), 19.8±0.3 (°2θ), 20.3±0.3 (°2θ), 20.5±0.3 (°2θ), 23.3±0.3 (°2θ), 24.7±0.3 (°2θ), 25.3±0.3 (°2θ), and 26.5±0.3 (°2θ).

Pharmaceutical Compositions and Administrations

The disclosure also provides for compositions and medicaments comprising compound I Form A. The compositions of the disclosure can be used for inhibiting DLK activity in patients (e.g., humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the disclosure provides for pharmaceutical compositions (or medicaments) comprising compound I Form A (or stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the disclosure provides for preparing compositions (or medicaments) comprising compounds of the disclosure. In another embodiment, the disclosure provides for administering compound I Form A and compositions comprising compound I Form A to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit DLK activity as required to prevent or treat the undesired disease or disorder, such as for example, neurodegeneration, amyloidosis, formation of neurofibrillary tangles, or undesired cell growth. For example, such amount may be below the amount that is toxic to normal cells, or the mammal as a whole.

In one example, the therapeutically effective amount of compound I Form A administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily dose is, in certain embodiments, given as a single daily dose or in divided doses two to six times a day, or in sustained release form. In the case of a 70 kg adult human, the total daily dose will generally be from about 100 mg to about 1,400 mg. This dosage regimen may be adjusted to provide the optimal therapeutic response. Compound I Form A may be administered on a regimen of 1 to 4 times per day, preferably once or twice per day.

The compounds of the present disclosure may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

Compound I Form A may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

Compound I Form A may be formulated in accordance with standard pharmaceutical practice as a pharmaceutical composition. A typical formulation is prepared by mixing compound I Form A and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of compound I Form A or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which compound I Form A is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Compound I Form A can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21st Edition, Lippincott Williams & Wilkins, Philidelphia, PA.

Sustained-release preparations of compound I Form A can be prepared. Suitable examples of sustained-release preparations include semipermeable matrices of solid hydrophobic polymers containing compound I Form A or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988 Å). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamellar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21st Edition, Lippincott Williams & Wilkins, Philidelphia, PA. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing compound I Form A and a carrier, diluent or excipient. The formulations can be prepared using conventional dissolution and mixing procedures. For example, bulk compound I Form A is dissolved in a suitable solvent in the presence of one or more of the excipients described above. Compound I Form A may be formulated into pharmaceutical dosage forms to provide an easily controllable dosage of the drug and to enable patient compliance with the prescribed regimen.

In one example, compound I Form A or any embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, compound I Form A or an embodiment thereof is formulated in an acetate buffer, at pH 5. In another embodiment, compound I Form A or an embodiment thereof are sterile. The compound may be stored, for example, as a solid or amorphous composition, as a lyophilized formulation or as an aqueous solution.

Formulations of compound I Form A suitable for oral administration can be prepared as discrete units such as pills, capsules, cachets or tablets each containing a predetermined amount of compound I Form A.

Compressed tablets can be prepared by compressing in a suitable machine compound I Form A in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of compound I Form A therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of compound I Form A intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing compound I Form A in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet or capsule containing about 1 mg, 5 mg, 10 mg, 25 mg, 30 mg, 50 mg, 80 mg, 100 mg, 150 mg, 200 mg, 250 mg, 300 mg and 500 mg of compound I Form A compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. In embodiments, the dosage form is a capsule containing 100 mg of compound I Form A. In embodiments, the dosage form is a capsule containing 200 mg of compound I Form A.

An example of an aerosol formulation can be prepared by dissolving compound I Form A, for example 5-400 mg, in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing compound I Form A in an amount of, for example, 0.075 to 20% w/w. When formulated in an ointment, compound I Form A can be employed with either a paraffinic or a water-miscible ointment base. Alternatively, compound I Form A can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this disclosure can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the disclosure include Tween® 60, Span® 80, cetostearyl alcohol, benzyl alcohol, myristyl alcohol, glyceryl mono-stearate and sodium lauryl sulfate.

Aqueous suspensions of compound I Form A contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of compound I Form A can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg, or 100 to 500 mg, of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the disclosure provide for compound I Form A to traverse the blood-brain barrier. Certain neurodegenerative diseases are associated with an increase in permeability of the blood-brain barrier, such that compound I Form A can be readily introduced to the brain. When the blood-brain barrier remains intact, several art-known approaches exist for transporting molecules across it, including, but not limited to, physical methods, lipid-based methods, and receptor and channel-based methods.

Physical methods of transporting compound I Form A across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting compound I Form A across the blood-brain barrier include, but are not limited to, encapsulating compound I Form A in liposomes that are coupled to antibody binding fragments that bind to receptors on the vascular endothelium of the blood-brain barrier (see, e.g., U.S. Patent Application Publication No. 2002/0025313), and coating compound I Form A in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting compound I Form A across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of compound I Form A with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Compound I Form A used in the disclosure are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. Compound I Form A need not be, but is optionally formulated with one or more agent currently used to prevent or treat the disorder in question. The effective amount of such other agents depends on the amount of a compound of the disclosure present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of compound I Form A (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 μg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 μg kg to 100 mg/kg or more, depending on the factors mentioned above. For repeated administrations over several days or longer, depending on the condition, the treatment would generally be sustained until a desired suppression of disease symptoms occurs. One exemplary dosage of compound I Form A would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 μg kg to 1 mg/kg, about 1 μg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

Indications and Methods of Treatment

In another aspect, the disclosure provides for methods of inhibiting the Dual Leucine Zipper Kinase (DLK) in an in vitro (e.g., a nerve graft of nerve transplant) or in vivo setting (e.g., in a patient) by contacting DLK present in an in vitro or in vivo setting with compound I Form A. In these methods of the disclosure, the inhibition of DLK signaling or expression with compound I Form A results in a downstream decrease in JNK phosphorylation (e.g., a decrease in JNK2 and/or JNK3 phosphorylation), JNK activity (e.g., a decrease in JNK2 and/or JNK3 activity), and/or JNK expression (e.g., a decrease in JNK2 and/or JNK3 expression). Accordingly, administering compound I Form A according to the methods of the disclosure can result in decrease in activity of kinase targets downstream of the DLK signalling cascade, e.g, (i) a decrease in JNK phosphorylation, JNK activity, and/or JNK expression, (ii) a decrease in cJun phosphorylation, cJun activity, and/or cJun expression, and/or (iii) a decrease in p38 phosphorylation, p38 activity, and/or p38 expression.

Compound I Form A can be used in methods for inhibiting neuron or axon degeneration. The inhibitors are, therefore, useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurodegenerative diseases and conditions that can be prevented or treated according to the disclosure include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS demential complex (also known as HIV dementia, HIV encephalopathy, and HIV-associated dementia).

The methods of the disclosure can also be used in the prevention and treatment of ocular-related neurodegeneration and related diseases and conditions, such as glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Non-limiting examples of different types of glaucoma that can be prevented or treated according to the disclosure include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochronic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphemia and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy.

Examples of types of pain that can be treated according to the methods of the disclosure include those associated with the following conditions: chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, tom ligament, and diabetes.

Certain diseases and conditions having primary effects outside of the nervous system can lead to damage to the nervous system, which can be treated according to the methods of the present disclosure. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the disclosure can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine. Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The methods of the disclosure can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

Further, the methods of the disclosure can be used in the prevention or treatment of memory loss such as, for example, age-related memory loss. Types of memory that can be affected by loss, and thus treated according to the disclosure, include episodic memory, semantic memory, short-term memory, and long-term memory. Examples of diseases and conditions associated with memory loss, which can be treated according to the present disclosure, include mild cognitive impairment, Alzheimer's disease, Parkinson's disease, Huntington's disease, chemotherapy, stress, stroke, and traumatic brain injury (e.g., concussion).

The methods of the disclosure can also be used in the treatment of psychiatric disorders including, for example, schizophrenia, delusional disorder, schizoaffective disorder, schizophreniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the disclosure can be used to treat nerves ex vivo, which may be helpful in the context of nerve grafts or nerve transplants. Thus, the inhibitors described herein can be useful as components of culture media for use in culturing nerve cells in vitro.

Accordingly, in another aspect, the disclosure provides for a method for inhibiting or preventing degeneration of a central nervous system (CNS) neuron or a portion thereof, the method comprising administering compound I Form A to the CNS neuron.

In one embodiment, of the method for inhibiting or preventing degeneration of a central nervous system neuron or a portion thereof, the administering to the CNS neuron is performed in vitro. In another embodiment, of the method for inhibiting or preventing degeneration of a central nervous system neuron or a portion thereof, the method further comprises grafting or implanting the CNS neuron into a human patient after administration of the agent. In another embodiment, of the method for inhibiting or preventing degeneration of a central nervous system neuron or a portion thereof, the CNS neuron is present in a human patient.

In another embodiment, of the method for inhibiting or preventing degeneration of a central nervous system neuron or a portion thereof, the administering to the CNS neuron comprises administration of compound I Form A in a pharmaceutically acceptable carrier, diluent or excipient.

In another embodiment, of the method for inhibiting or preventing degeneration of a central nervous system neuron or a portion thereof, the administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device.

In another embodiment, of the method for inhibiting or preventing degeneration of a central nervous system neuron or a portion thereof, the method further comprises administering one or more additional pharmaceutical agents.

The inhibitors can be optionally combined with or administered in concert with each other or other agents known to be useful in the treatment of the relevant disease or condition. Thus, in the treatment of ALS, for example, inhibitors can be administered in combination with Riluzole (Rilutek), minocycline, insulin-like growth factor 1 (IGF-1), and/or methylcobalamin. In another example, in the treatment of Parkinson's disease, inhibitors can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, inhibitors can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The disclosure also includes pharmaceutical compositions and kits comprising combinations as described herein.

In addition to the combinations noted above, other combinations included in the disclosure are combinations of inhibitors of degeneration of different neuronal regions. Thus, the disclosure includes combinations of agents that (i) inhibit degeneration of the neuron cell body, and (ii) inhibit axon degeneration. For example, inhibitors of GSK and transcription are found to prevent degeneration of neuron cell bodies, while inhibitors of EGFR and p38 MAPK are found to prevent degeneration of axons. Thus, the disclosure includes combinations of inhibitors of GSK and EGFR (and/or p38 MAPK), combinations of transcription inhibitors and EGF (and/or p38 MAPK), and further combinations of inhibitors of dual leucine zipper-bearing kinase (DLK), glycogen synthase kinase 3β (GSK3), p38 MAPK, EGFF, phosphoinositide 3-kinase (PI3K), cyclin-dependent kinase 5 (cdk5), adenylyl cyclase, c-Jun N-terminal kinase (JNK), BCL2-associated X protein (Bax), In channel, calcium/calmodulin-dependent protein kinase kinase (CaMKK), a G-protein, a G-protein coupled receptor, transcription factor 4 (TCF4), and β-catenin. The inhibitors used in these combinations can be any of those described herein, or other inhibitors of these targets as described in WO 2011/050192, incorporated herein by reference.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

EXAMPLES

For compound genus (i) species compound 10 and compound genus (ii) species compound 11, HPLC analysis was done with: a 100×4.6 mm column; a C18, 2.7 μm (e.g., Ascentis Express C18) stationary phase; 25° C. column temperature; DAD, 298 nm, 8 nm bandwidth detection; flow rate of 1.0 mL/min; 5.0 μL injection volume; water/acetonitrile 3:7 v/v diluent; 0.05% v/v TFA in water Mobile Phase A; 0.05% v/v TFA in acetonitrile Mobile Phase B; and about 14 minute acquisition time. The gradient program was as follows and the RRT for the compound 10 and compound 11 species were 1.34 and 1.00, respectively:

| Time (min) | Mobile Phase A (%) | Mobile Phase B (%) |
|---|---|---|
| 0.0 | 80 | 20 |
| 1.0 | 80 | 20 |
| 11 | 5 | 95 |
| 14 | 5 | 95 |
| 14.1 | 80 | 20 |
| 19 | 80 | 20 |

For compound genus (ii) species compound 11 and compound genus (iii) species compound 16, HPLC analysis was done with: a 150×3.0 mm column; an Agilent Infinity Lab Poroshell HPH-C18 stationary phase, 2.7 μm; 33° C. column temperature; DAD, 260 nm, 8 nm bandwidth detection; flow rate of 0.75 mL/min; 5.0 μL injection volume; water/acetonitrile 8:2 v/v diluent; 10 mM $(NH_4)_2HPO_4$ in water, pH 7.3±0.2 Mobile Phase A; acetonitrile Mobile Phase B; and about 10.5 minute acquisition time. The gradient program was as follows and the RRT for the compound 11 and compound 16 species were 1.65 and 1.00, respectively:

| Time (min) | Mobile Phase A (%) | Mobile Phase B (%) |
|---|---|---|
| 0.0 | 88 | 12 |
| 1.5 | 88 | 12 |
| 4.0 | 79 | 21 |
| 5.0 | 79 | 21 |
| 9.5 | 20 | 80 |
| 10.5 | 20 | 80 |
| 10.7 | 88 | 12 |
| 14 | 88 | 12 |

For compound genus (iii) species compound 16, compound genus (iv) species compound 23, and compound genus (v) species compound 24, HPLC analysis was done with: a 150×3.0 mm column; an Agilent Infinity Lab Poroshell HPH-C18 stationary phase, 2.7 μm; 33° C. column temperature; DAD, 238 nm, 8 nm bandwidth detection; flow rate of 0.5 mL/min; 3.0 μL injection volume; water/acetonitrile 1:1 v/v diluent; 10 mM $(NH_4)_2HPO_4$ in water, pH 7.3±0.2 Mobile Phase A; acetonitrile Mobile Phase B; and about 25 minute acquisition time. The gradient program was as follows and the RRT for the compound 23, compound 16, and compound 24 species were 0.3, 0.79, and 1.00, respectively:

| Time (min) | Mobile Phase A (%) | Mobile Phase B (%) |
|---|---|---|
| 0.0 | 88 | 12 |
| 1.0 | 88 | 12 |
| 19.0 | 50 | 50 |
| 21.0 | 20 | 80 |
| 25.0 | 20 | 80 |
| 25.1 | 88 | 12 |
| 30.0 | 88 | 12 |

For compound 1 (crude), HPLC analysis was done with: a 150×3.0 mm column; a Poroshell HPH-C18 stationary phase, 2.7 μm; 33° C. column temperature; DAD, 276 nm, 8 nm bandwidth detection; flow rate of 0.5 mL/min; 5.0 μL injection volume; water/acetonitrile 1:1 v/v diluent; 10 mM $(NH_4)_2HPO_4$ in water, pH 7.3±0.2 Mobile Phase A; acetonitrile Mobile Phase B; and about 20 minute acquisition time. The gradient program was as follows:

| Time (min) | Mobile Phase A (%) | Mobile Phase B (%) |
|---|---|---|
| 0.0 | 88 | 12 |
| 1.0 | 88 | 12 |
| 7.0 | 50 | 50 |
| 17.0 | 35 | 65 |
| 18.0 | 20 | 80 |
| 20.0 | 20 | 80 |
| 20.1 | 88 | 12 |
| 25.0 | 88 | 12 |

The Peak table is as follows:

| Component | RRT |
|---|---|
| Compound 24 | 0.63 |
| Compound (24) substitution product impurity | 0.74 |
| Monofluoro analog impurity | 0.87 |
| n-Butyl analog impurity | 0.93 |
| Compound formula I (crude) | 1.00 |
| Des-fluoro analog impurity | 1.04 |
| n-Pentyl analog impurity | 1.07 |
| Dimer impurity | 1.22 |
| di-n-Butyl analog impurity | 1.93 |

For purified compound 1, the same method for compound 1 (crude) was done with the following gradient program:

| Time (min) | Mobile Phase A (%) | Mobile Phase B (%) |
|---|---|---|
| 0.0 | 88 | 12 |
| 1.0 | 88 | 12 |
| 19.0 | 35 | 65 |
| 21.0 | 20 | 80 |
| 25.0 | 20 | 80 |
| 25.1 | 88 | 12 |
| 30.0 | 88 | 12 |

The Peak table is as follows:

| Component | RRT |
|---|---|
| Compound 24 | 0.58 |
| Compound (24) substitution product impurity | 0.75 |
| Monofluoro analog impurity | 0.89 |

-continued

| Component | RRT |
|---|---|
| n-Butyl analog impurity | 0.95 |
| Compound formula I | 1.00 |
| Des-fluoro analog impurity | 1.03 |
| n-Pentyl analog impurity | 1.05 |
| Dimer impurity | 1.14 |
| di-n-Butyl analog impurity | 1.44 |

Example 1: Preparation of 3-(difluoromethoxy)-5-(4,4,5,5-tetramethyl-1,3,2-dioxaborolan-2-yl)pyridin-2-amine (Compound (23))

Compound (23) is a species of compound (iii).

Step 1: Preparation of 3-(difluoromethoxy)-2-nitropyridine (Compound (19))

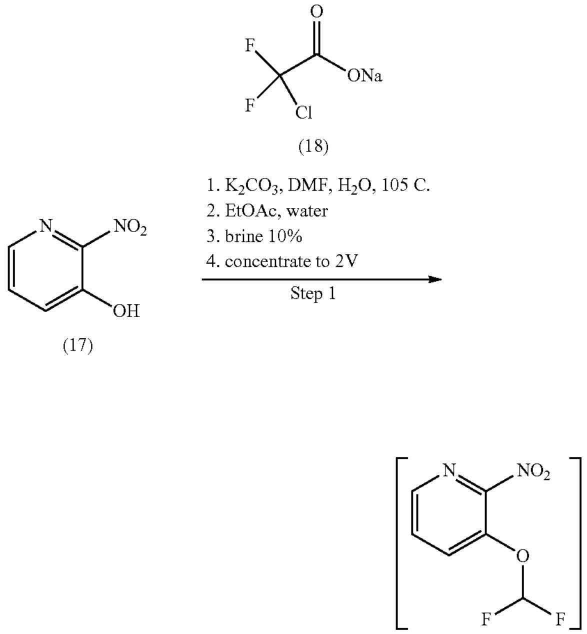

(18)

(17)

(19)

In step, 1(1), a reaction mixture was formed by combining 2-nitropyridin-3-ol (compound (17)) with sodium 2-chloro-2,2-difluoroacetate (compound (18)) and aqueous potassium carbonate in dimethyl formamide. The reaction mixture was heated to 70° C. and held at that temperature to form a reaction product mixture comprising compound (19). In step 1(2), compound (19) was extracted with ethyl acetate and water to form a solution comprising compound (19). In step 1(3), the solution of compound (19) was washed with 10% brine, and the washed solution of compound (19) was then concentrated to two volumes in step 1(4).

Step 2: Preparation of 3-(difluoromethoxy)pyridin-2-amine (Compound (20))

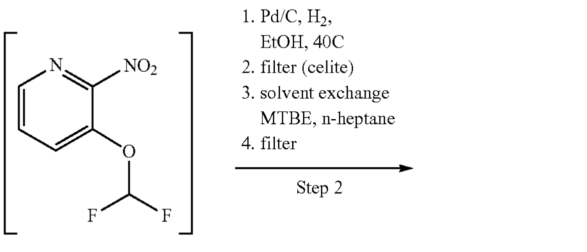

(19)

3-(difluoromethoxy)pyridin-2-amine (20)

In step 2(1), the solution of compound (19) was diluted with ethanol and catalytically hydrogenated at 40° C. with a palladium on carbon catalyst to form a solution of compound (20). In step 2(2), celite filter aid was added to the solution of compound (20) followed by filtration. In step 2(3), a solvent exchange to methyl tert-butyl ether MTBE was done, followed by the addition of n-heptane anti-solvent to precipitate compound (20) and form a slurry thereof. In step 2(4) the slurry of compound (20) was filtered to collect compound (20).

Step 3: Preparation of 5-bromo-3-(difluoromethoxy)pyridin-2-amine (Compound 21))

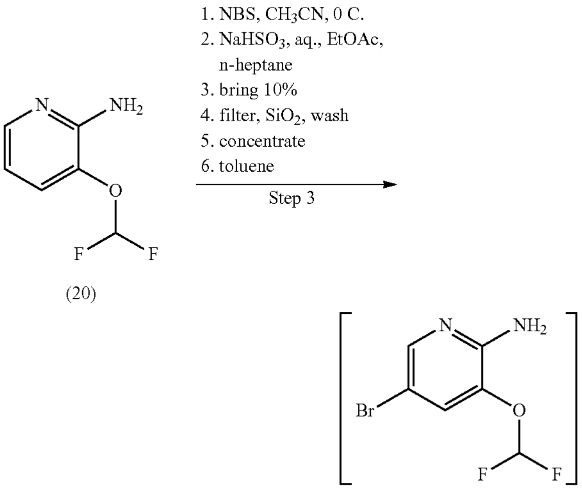

(20)

(21)

In step 3(1), compound (20) from step 2 was combined with N-bromosuccinimide (NBS) in acetonitrile and reacted at 0° C. to form a solution of compound (21). In step 3(2), compound (21) was neutralized with aqueous sodium bisulfite and extracted to ethyl acetate/n-heptane 13:1. In step 3(3), the solution of compound (21) in ethyl acetate/n-heptane was washed with 10% brine. The solution was filtered, through celite in step 3(4). In step 3(5) the filtrate containing compound (21) was concentrated, followed by dilution with toluene in step 3(6) to form a solution of compound (21).

Step 4: Preparation of 3-(difluoromethoxy)-5-(4,4,5,5-tetramethyl-1,3,2-dioxaborolan-2-yl)pyridin-2-amine maleic acid (Compound (22))

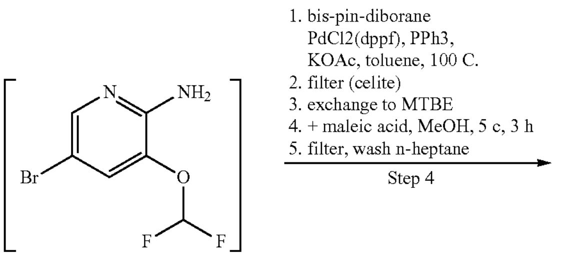

(21)

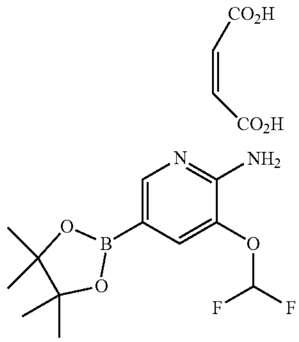

(22)

In step 4(1), the solution of compound (21) from step 3 was combined with Bis(pinacolato)diboron (bis-pin-diborane), [1,1'-Bis(diphenylphosphino)ferrocene]palladium(II) dichloride ($PdCl_2$(dppf)), triphenyphosphine ($PPh_3$), potassium acetate and toluene to form a reaction mixture. The reaction mixture was reacted at 100° C. to form a solution containing compound (22) free base. In step 4(2), the solution was filtered through celite. In step 4(3), the solvent of the solution of compound (22) was exchanged to methyl tert-butyl ether. In step 4(4), the solution of compound (22) free base was combined with maleic acid and methanol, and held at −10° C. for at least 2 hours to form a slurry of compound (22). In step 4(5), compound (22) was collected from the slurry from step 4(4) by filtration, and the collected compound (22) was washed with methyl tert-butyl ether and dried to form compound (22).

Step 5: Preparation of 3-(difluoromethoxy)-5-(4,4,5,5-tetramethyl-1,3,2-dioxaborolan-2-yl)pyridin-2-amine (Compound (23))

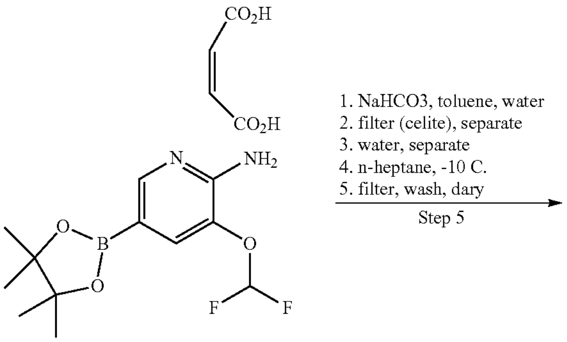

(22)

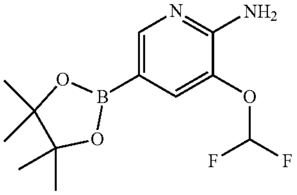

(23)

In step 5(1), compound (22) from step 4 was dissolved in toluene and neutralized with aqueous sodium bicarbonate to form compound (23) free base in solution. In step 5(2), the solution of compound (23) was filtered through celite, the filtrate was allowed to separate into organic and aqueous phases, and the aqueous phase was removed. The organic phase containing compound (23) in solution was washed with water, followed by phase separation and removal of the aqueous phase. The organic phase was concentrated, combined with n-heptane anti-solvent at −10° C. to precipitate compound (23) from solution and form a slurry. The slurry was filtered, washed with n-heptane and dried to form finished compound (23).

Example 2: Preparation of 3,3-difluoropyrrolidine hydrochloride salt (Compound (28))

Step 1: Preparation of 1-benzyl-3,3-difluoropyrrolidine hydrochloride salt (Compound (26))

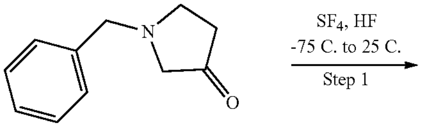

(25)

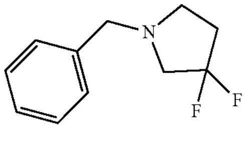

(26)

Step 2: Preparation of 1-benzyl-3,3-difluoropyrrolidine hydrochloride salt (Compound 27))

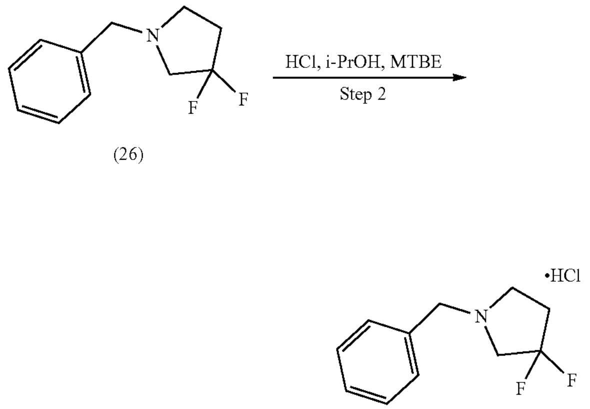

(26)

(27)

In step 1, 1-benzylpyrrolidin-3-one (compound (25)) was dissolved in dichloromethane (DCM) and cooled to −50° C. Hydrofluoric acid and sulfur tetrafluoride were added, and the reaction mixture was reacted at 0° C. to form compound (26). The reaction mixture was quenched by the addition of aqueous KOH at 0° C. The layers were separated and the organic phase was washed with 10% brine. DCM was removed by distillation, and 1-propanol was added. The solution was filtered on a C pad. In step 2, a solution of HCl in 1-propanol was charged to obtain a slurry. The slurry was heated to 40° C., then MTBE was added and the slurry was cooled to 0° C. and filtered. The solid was washed with 1-propanol/MTBE and dried.

Step 3: Preparation of 3,3-difluoropyrrolidine hydrochloride salt (Compound (28))

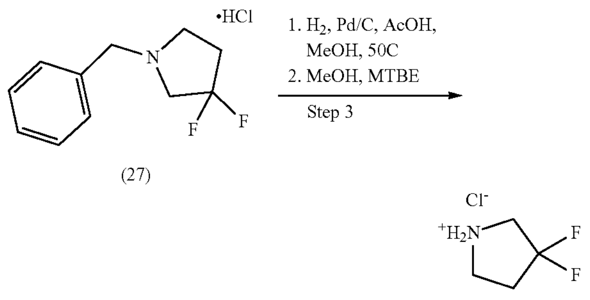

(27)

(28)

In step 3(1), compound (27) was diluted with methanol and acetic acid and catalytically hydrogenated at 40° C. with a palladium on carbon catalyst to form a solution of compound (28). In step 3(2), the suspension was filtered on decalite, methanol was exchanged for 1-propanol. At 40-45° C., MTBE was added to the suspension which was cooled to 0° C. and aged for at least 2 hours. The precipitate was filtered and washed with 1-propanol/MTBE to give compound (28).

Example 3: (1S,4S)-2-oxa-5-azabicyclo[2.2.1]heptane hydrogen chloride (Compound (5))

Compound (5) is a species of compound (vii).

Step 1: Preparation of BOC protected methyl (2S,4R)-4-(tosyloxy)pyrrolidine-2-carboxylate (Compound (2))

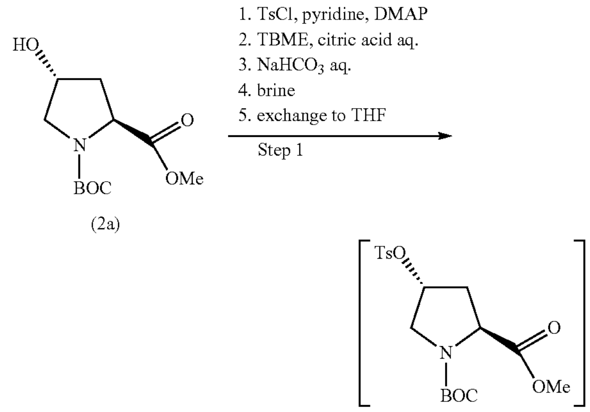

(2a)

(2)

In step 1(1), a reaction vessel was charged with BOC protected methyl (2S,4R)-4-hydroxypyrrolidine-2-carboxylate (compound (2a)), pyridine and catalytic amount of 4-dimethylaminopyridine (DMAP). The reaction mixture was cooled to 0-10° C. 4-Toluenesulfonyl chloride (TsCl), was added within 1 hour. The temperature was brought to 20-30° C. within 4-6 hours and the reaction mixture stirred for at least 16 hours at 20-30° C. to form a reaction product mixture comprising compound (2). In step 1(2), the reaction product mixture from step 1(1) was combined with methyl tert-butyl ether and aqueous citric acid. In steps 1(3) and 1(4), the solution from step 1(2) was neutralized with aqueous sodium bicarbonate and washed with brine, respectively. In step 1(5), a solvent exchange to tetrahydrofuran (THF) was done to generate a solution of compound (2).

Step 2: Preparation of BOC protected (3R,5S)-5-(hydroxymethyl)pyrrolidin-3-yl 4-methylbenzenesulfonate (Compound (3))

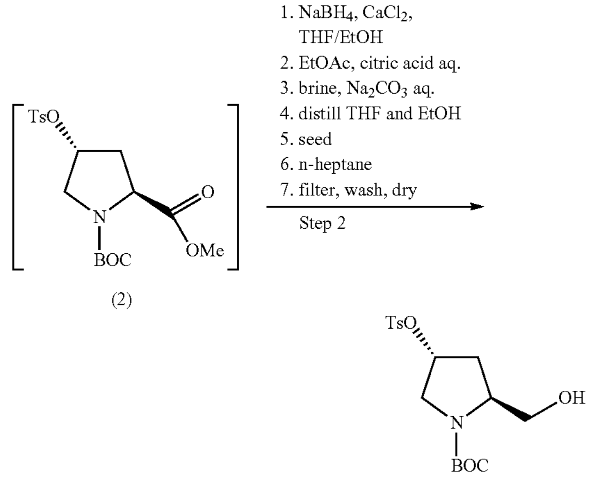

(2)

(3)

In step 2(1), the solution of compound (2) from step 1 was cooled to 10-20° C. and calcium chloride, ethanol and water were added maintaining temperature to 10-20° C. Sodium borohydride ($NaBH_4$) was added slowly in several portions. Stirring was continued for 1-2 hours at 10-20° C. then for 1-4 hours at 20-30° C. to form a solution of compound (3). In step 2(2), the solution was combined with ethyl acetate and a mixture of aqueous citric acid and brine. The aqueous phase was extracted with ethyl acetate. In step 2(3), the organic phase from step 2(3) was washed with brine, with a mixture of aqueous sodium carbonate and brine, and finally with brine. In step 2(4), the organic phase comprising compound (3) in solution was distilled to remove THF and ethanol, the resulting concentrate was seeded with BOC protected (3R,5S)-5-(hydroxymethyl)pyrrolidin-3-yl 4-methylbenzenesulfonate in step 2(5), and n-heptane anti-solvent was added to the seeded solution to form a slurry of compound (3) in step 2(6). In step 2(7), the slurry from step 2(6) was filtered, washed with n-heptane and dried to afford compound (3) in 84% yield over 2 steps.

Step 3: Preparation of BOC protected (1S,4S)-2-oxa-5-azabicyclo[2.2.1]heptane (Compound (4))

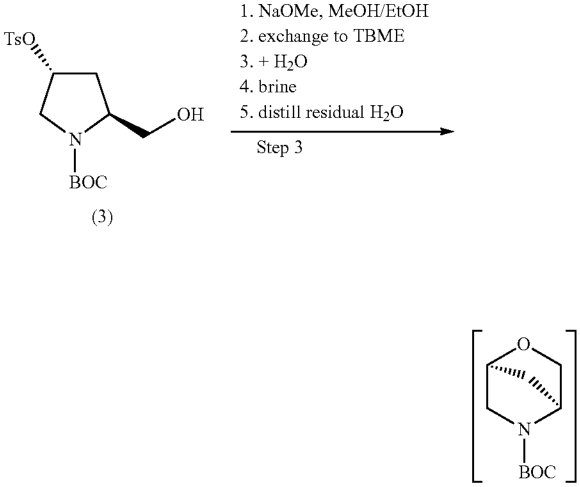

(4)

In step 3(1), compound (3) from step 2 was dissolved in a 10:1 mixture of methanol and ethanol. Sodium methoxide was added in portions at 15-30° C. then the reaction mixture was heated to 60-70° C. and stirred at this temperature for 2 hours to form BOC protected bicyclic amine compound (4) by ring closure. Solvent mixture was exchanged to methyl tert-butyl ether, and the organic solution was washed with diluted brine. The aqueous phase was extracted with TBME. The combined organic layers were washed with brine, polish filtered and concentrated under reduced pressure.

Step 4: (1S,4S)-2-oxa-5-azabicyclo[2.2.1]heptane hydrogen chloride salt (Compound (5))

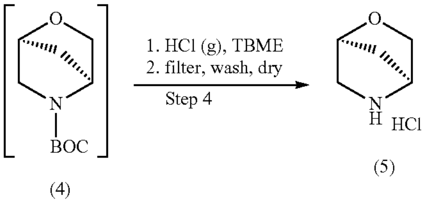

(4) (5)

In step 4(1), the solution of compound (4) was diluted with additional methyl tert-butyl ether and HCl (gas) was added at 20-30° C. in 3 portions with 1-2 hours aging after each addition to deprotect the amine and form a slurry of compound (5). Excess HCl was removed in 3 cycles of distillation and addition of MTBE. In step 4(2), the slurry from step 4(1) was cooled to 0-5° C., aged for 1-2 hours, filtered to isolate compound (5) which was then washed with TBME, and dried affording compound (5) in 84% yield.

Optionally, Compound (5) can be re-crystallized. Compound (5) is dissolved in methanol 20-30° C. and the solution is polish-filtered. The solvent is exchanged to MTBE and the suspension aged at 0-5° C. The precipitate is filtered off, washed with MTBE and dried to afford purified compound (5) in 96% yield.

Example 4: 4,6-dichloro-2-(methylthio)pyrimidine (Compound (10))

Compound (10) is a species of compound (i).

Step 1: Preparation of 2-mercaptopyrimidine-4,6-diol (Compound (8))

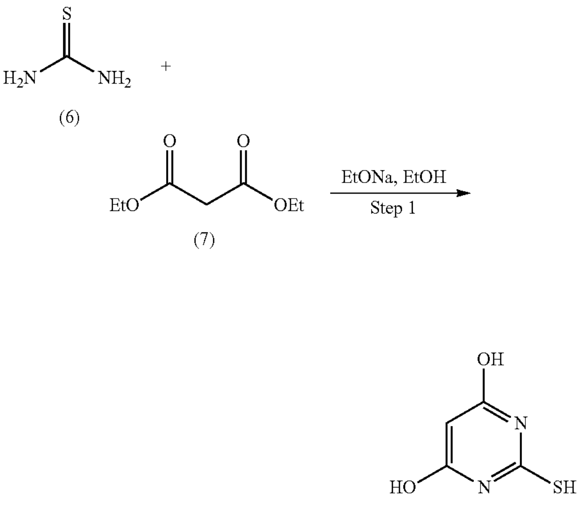

(8)

Thiourea (compound (6)) and diethyl malonate (compound (7)) were combined in ethanol with sodium ethoxide base to form compound (8).

Step 2: Preparation of 2-(methylthio)pyrimidine-4,6-diol (Compound (9))

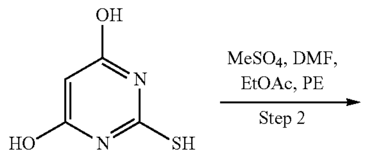

(8)

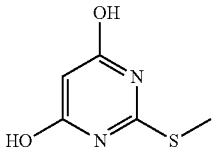

(9)

Compound (8) was combined with methyl bisulfate and petroleum ether ("PE') in DMF and ethyl acetate and reacted to form compound (9).

Step 3: Preparation of 4,6-dichloro-2-(methylthio)pyrimidine (Compound

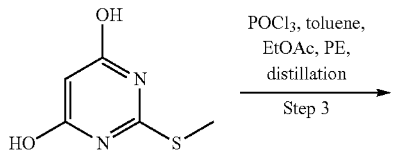

(9)

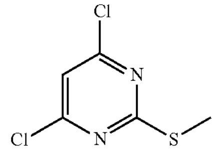

(10)

In step 3(1), compound (9) was combined with phosphoryl chloride ($POCl_3$) and PE in toluene and ethyl acetate and reacted to form a solution containing compound (10). In step 3(2), the solution of compound (10) is distilled to form finished compound (10).

Example 5: 5-(6-((1S,4S)-2-oxa-5-azabicyclo[2.2.1]heptan-5-yl)-2-(3,3-difluoropyrrolidin-1-yl)pyrimidin-4-yl)-3-(difluoromethoxy)pyridin-2-amine (Compound 1)

Step 1: Preparation of (1S,4S)-5-(6-chloro-2-(methylthio)pyrimidin-4-yl)-2-oxa-5-azabicyclo[2.2.1]heptane (Compound (11))

Compound (11) is a species of compound (ii).

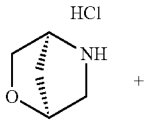

(5)

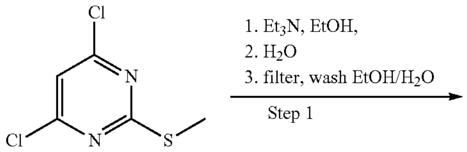

(10)

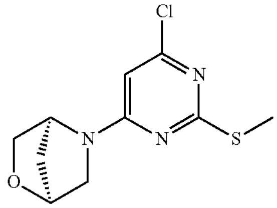

(11)

(1S,4S)-2-oxa-5-azabicyclo[2.2.1]heptane hydrochloride (23.4 grams; 172.6 mmol; 1.12 eq) (compound (5)), 4,6-dichloro-2-(methylthio)pyrimidine (compound (10)) (30.0 grams; 153.8 mmol; 1.0 eq) and ethanol (236.7 grams; 300 mL; 10 vol) were charged under an inert atmosphere to a 500 mL double jacketed reactor fitted with a mechanical stirrer, thermometer, cryostat, argon/nitrogen inlet, and suction filter. A colorless solution formed within 20 minutes upon stirring and the solution was heated to 35° C. Triethylamine (37.5 grams; 369.1 mmol; 2.4 eq) was added dropwise over a period of two hours. During addition, a precipitate formed leading to a white suspension, which was further stirred at 35° C. for about 5 hours reaction time until the amount of compound (10) remaining reached a predetermined amount as determined by in-process control testing ("IPC"). The reaction mixture was cooled to 22° C. followed by stirring at room temperature for about 16 hours. Solid compound (11) was isolated by filtration, and washed twice with 85 mL of water/EtOH 85:15. Compound (11) was dried under high vacuum for at least 14 hours to yield 37.5 grams (94.5%) as a white powder.

In embodiments, the step 1 method above is performed for 4-5 hours at a reaction temperature of 22° C., 7.5 vol ethanol and from 2.2 to 2.6 equivalents of triethylamine.

In embodiments, the step 1 method above is performed for 5 hours at a reaction temperature of 35° C., 10 vol ethanol and 2.4 equivalents of triethylamine.

Step 2: Preparation of (1S,4S)-5-(6-chloro-2-(methylsulfonyl)pyrimidin-4-yl)-2-oxa-5-azabicyclo[2.2.1]heptane (Compound (16))

Compound (16) is a species of compound (iii).

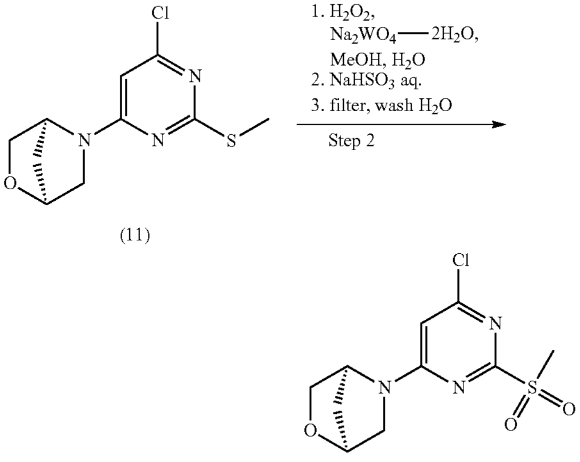

(11)

(16)

A 500 mL double-jacketed reactor was charged under inert atmosphere with methanol (200 mL) and water (100 mL) followed by addition of compound (11) (20.0 grams; 77.6 mmol; 1.0 eq) and sodium tungstate dihydrate (0.78 mmol; 0.1 eq) to form a white suspension. The suspension was heated to 60° C. followed by addition of 35% hydrogen peroxide (178.5 mmol $H_2O_2$; 2.3 eq) over a period of 4 hours. The reaction mixture was stirred at 60° C. until IPC complied.

The suspension of compound (16) was cooled to room temperature and 40% aqueous sodium bisulfite (20.2 grams sodium bisulfite; 77.6 mmol; 1.0 eq) was added over about 30 minutes, and the resulting suspension was stirred at room temperature for 3 hours. Solid compound (16) was isolated by filtration, and washed twice with 134 mL of water. Compound (16) was dried under reduced pressure for at least 14 hours to yield 20.6 grams (91.6%) as a white powder.

Step 3: Preparation of 5-(6-((1S,4S)-2-oxa-5-azabicyclo[2.2.1]heptan-5-yl)-2-(methylsulfonyl)pyrimidin-4-yl)-3-(difluoromethoxy)pyridin-2-amine (Compound 1)

Compound (24) is a species of compound (v).

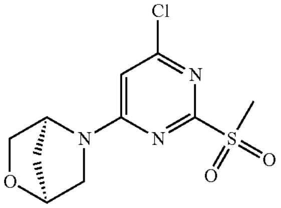

(16)

+

-continued

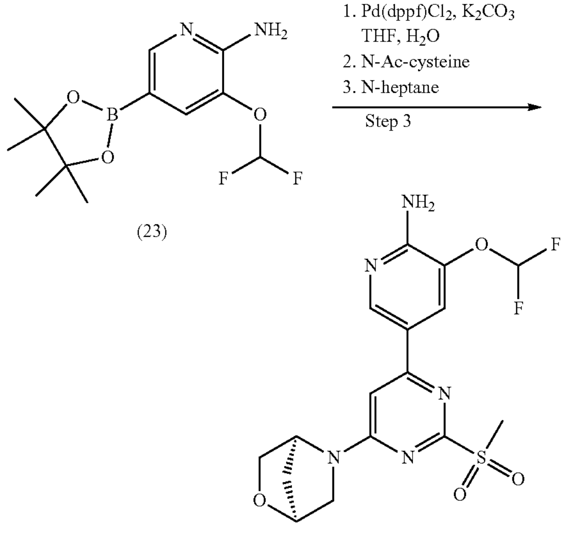

(23)

(24)

A 500 mL double-jacketed reactor was charged under argon with tetrahydrofuran (300 mL) and water (87.5 mL) followed by addition of compound (16) (25.0 grams; 86.3 mmol; 1.0 eq) and 3-(difluoromethoxy)-5-(4,4,5,5-tetramethyl-1,3,2-dioxaborolan-2-yl)pyridin-2-amine (compound (23)) (28.4 g; 99.2 mmol; 1.15 eq) to form a brown suspension. The reactor was evacuated and filled with argon 3 times. [1,1'-Bis(diphenylphosphino)ferrocene]dichloropalladium(II) ("Pd(dppf)$Cl_2$") (0.31 grams; 0.43 mmol; 0.005 eq) was then added and the suspension was heated to 60-65° C. and stirred until IPC complied. The reaction mixture was then cooled to 55-58° C. followed by addition of N-acetylcysteine (1.41 grams; 8.6 mmol; 0.1 eq) in 15 grams water. The mixture was stirred for about 30 minutes followed by addition of n-heptane (51.3 grams; 75 mL). The mixture was stirred at room temperature overnight. Solid compound (24) was collected from the mixture by filtration and then washed twice with a mixture of THF (50 grams) and water (50 grams). The washed compound (24) solids were dried under reduced pressure at RT for 16 hours for a yield of 30.75 grams (86.2%) of an off-white powder.

Step 4: Preparation of 5-(6-((1S,4S)-2-oxa-5-azabicyclo[2.2.1]heptan-5-yl)-2-(3,3-difluoropyrrolidin-1-yl)pyrimidin-4-yl)-3-(difluoromethoxy)pyridin-2-amine (Compound 1)

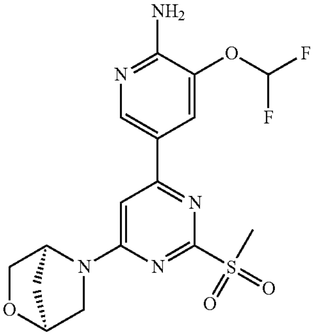

+

(24)

-continued

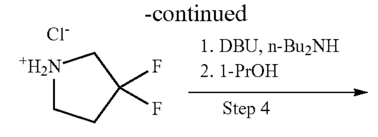

(28)

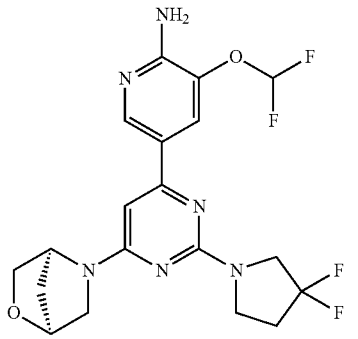

1

A 250 mL double-jacketed reactor was charged under inert atmosphere with compound (24) (20.0 g; 48.4 mmol; 1 eq), 3,3-difluoropyrrolidin-1-ium chloride (compound (28)) (10.4 g; 72.6 mmol; 1.5 eq) and di-n-butylamine (80.0 mL) followed by addition of 1,8-diazabicyclo[5.4.0]undec-7-ene ("DBU") (11.1 g; 72.6 mmol; 1.5 eq). The mixture was stirred at 125° C. for about 20 hours. The reaction was monitored by IPC for reaction completion. 1-Propanol (80 mL) was added to the reaction mixture over about 30 minutes followed by cooling to 20° C. over 6 hours to form a precipitate of crude compound formula I. Solid compound 1 was collected from the mixture by filtration and then washed twice with 1-propanol (80 mL) followed by drying at 60° C. at no more than 20 mbar for about 16 hours. 16.8 grams of crude compound 1 as an almost white to pale yellow powder with lumps was produced at a yield of 77.9%.

Example 6: 5-(6-((1S,4S)-2-oxa-5-azabicyclo[2.2.1]heptan-5-yl)-2-(3,3-difluoropyrrolidin-1-yl)pyrimidin-4-yl)-3-(difluoromethoxy)pyridin-2-amine (Compound 1)

Step 1: Preparation of 4,6-dichloro-2-(methylsulfonyl)pyrimidine (Compound (15))

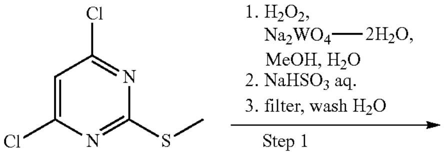

(10)

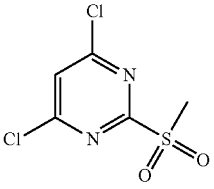

(15)

A reaction vessel was charged with 4,6-dichloro-2-(methylthio)pyrimidine (compound (10)) (25.0 g, 128.2 mmol), sodium tungstate dihydrate (426 mg, 1.29 mmol), methanol (250 mL) and water (125 mL). The reaction mixture was heated to 52° C., and $H_2O_2$ (35%, 28.3 g, 291.3 mmol) was added within 3 hours. The reaction mixture was further stirred for 2 hours, then cooled to 22° C. Aqueous sodium bisulfite 40% (25.0 mL, 127.8 mmol) was added within 30 minutes and the mixture was stirred for 1 hour at 22° C. and for 1 hour at 0° C. to form a slurry of compound (15). The slurry was filtered to isolate compound (15) which was then washed with water. The yield of compound (15) was 74% with 99.6 area % purity by HPLC.

Step 2: Preparation of (1S,4S)-5-(6-chloro-2-(methylsulfonyl)pyrimidin-4-yl)-2-oxa-5-azabicyclo[2.2.1]heptane (Compound (16))

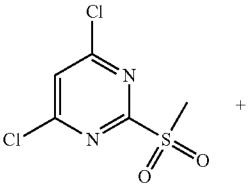

(15)

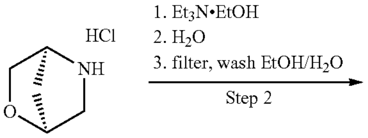

(5)

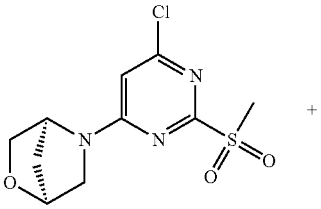

(16)

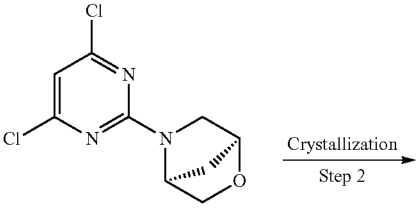

Regioisomer
(16)

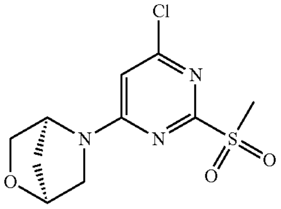

(16)

In step 2, compound (15) (3.0 g, 13.2 mmol), compound (5) (2.0 g, 14.8 mmol, 1.12 eq), and ethanol (18 mL) were charged under an inert atmosphere to a 50 mL reaction vessel. A colorless solution formed upon stirring, and the solution was heated to 35° C. Triethylamine (3.23 g, 31.7 mmol, 2.4 eq) was added dropwise over a period of two hours. The reaction mixture was further stirred at 35° C. for 3 hours to generate a reaction product mixture comprising compound (16) (about 80% HPLC area %) and regioisomer (17) (about 6-7% HPLC area %) in solution. The reaction mixture was cooled to 22° C., water (30 mL) was added, and the suspension was stirred for 1 hour at 22° C. The precipitate was filtered off and washed with water/EtOH. The isolated solids were dried under high vacuum for at least 14 hours to yield compound (16) in 98.3 area % purity and 82% yield. Water was added and the reaction mixture was cooled to 22° C. followed by stirring at room temperature for about 16 hours. Regioisomer (17) is more soluble in the solvent mixture than compound (16), and compound (16) predominantly crystallizes whereas regioisomer (17) predominantly remains in solution. Solids were isolated by filtration, and washed twice with water/EtOH. The isolated solids were dried under high vacuum for at least 14 hours to yield compound (16) in 98.3 area % purity and 82% yield.

Steps 3 and 4: Preparation of Compound 1

Crude compound 1 may be prepared from compound (16) according to steps 3 and 4 that correspond to steps 3 and 4 of Example 5.

Example 7: Purification of Crude Compound 1

Crude compound 1 was purified according to the following scheme:

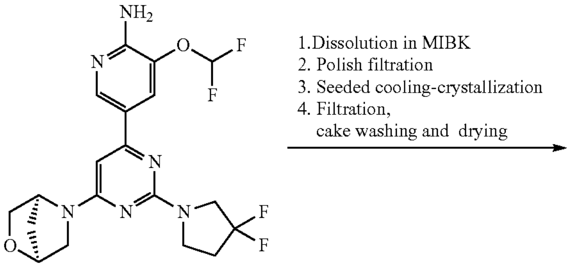

1

Crude

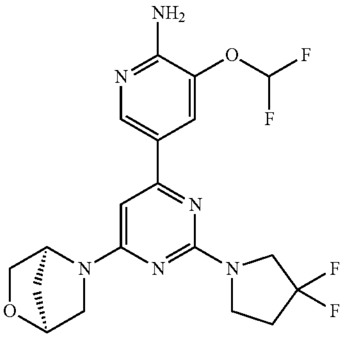

1

Purified

Step 1: Dissolution of Crude Compound Formula I

MIBK (399 mL) and crude compound 1 (25 g) were charged to a first 1000 mL double-jacketed reactor and heated with stirring to 90° C. to form a solution. The solution was filtered through a 0.2 μm PTFE polish filter to a second 1000 mL double-jacketed reactor where the temperature was maintained at 90° C. MIBK at 90° C. was rinsed through the first reactor and forwarded through the polish filter to the second reactor. A clear solution of crude compound 1 was produced. The solution was cooled to 75° C.

Step 2: Seeding and Cooling

In a glass vial, 0.1 gram of jet-milled purified crystalline compound 1 free base (form "A") was suspended with stirring for not less than 15 minutes in 3 mL MIBK at 20-25° C. The seed slurry was added to the solution of crude compound 1 with stirring to form a suspension. Following confirmation of the presence of particulate, the suspension was aged at 75° C. for one hour with stirring. The suspension was cooled to −10° C. with stirring at a rate of about 12 K/hour over about 7 hours and then aged with stirring at the final temperature for not less than 6 hours.

Step 3: Filtration, Washing and Drying

A first wash of 40 mL MIBK and a second wash of 40 mL ethanol were each cooled to 5° C. The suspension from step 2 was vacuum filtered through a Nutsche filter to collect crystallized compound 1. The wet compound 1 was washed sequentially with the MIBK wash and the ethanol wash to generate wet purified compound 1. Wet compound 1 was dried in drying cabinet at a temperature of 65° C. at a pressure of no more than 20 mbar until the weight was constant. 22.15 grams of almost-white in appearance purified compound 1 having an assay of 100% w/w was generated at a yield of 89.1%. Purified compound 1 is a crystalline free base having a melting point of from 197-200° C.

Example 8

The mono-substitution of 4,6-dichloro-2-methylsulfanyl-pyrimidine (10) by 2-oxa-5-azabicyclo[2.2.1]heptane (5) (1.12 eq.) was evaluated in different solvents in the presence of di-isopropyl-ethyl amine (2.4 eq.) at room temperature (22° C.) according to the following scheme.

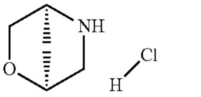

(5)
1.2 eq

+

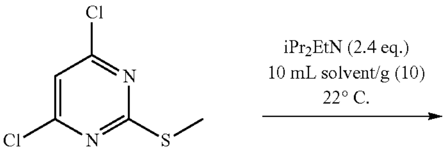

(10)

-continued

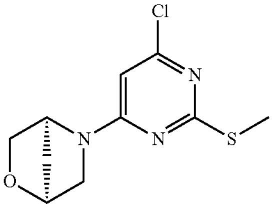

(11)

The product (11) was precipitated in the reaction medium and, after addition of 10 mL water per gram of compound (10) water to dissolve the salts, was isolated by simple filtration. The results of solvents screening are summarized in Table 1 where Trial 3 was done at 50° C. and Trial 7 used trimethylamine base.

TABLE 1

| Trial | Solvent | Reaction Time (h) | Conversion (%) | Isolated Yield (%) |
|---|---|---|---|---|
| 1 | THF | 18 | 82 | — |
| 2 | 2-Me-THF | 20 | 74 | — |
| 3 | iPrOAc | 23 | 46 | — |
| 4 | DMSO | 2 | 100 | 91.6 |
| 5 | CH3CN | 2 | 99.2 | 91.4 |
| 6 | EtOH | 2 | 98.4 | 96.4 |
| 7 | EtOH | 4 | 99.2 | |
| 8 | EtOH | 2 | 99.1 | 97.6 |
| 9 | EtOH | 4 | 99.5 | |

THF, 2-MeTHF and isopropyl acetate gave much slower reactions and conversion was still incomplete after 18 hours. DMSO, acetonitrile and ethanol afforded conversions >98% within 2-4 hours and isolated yields were >90%. Triethylamine base led to slightly faster conversion and higher isolated yield.

Trials 8 and 9 (ethanol solvent and triethylamine base) were repeated at a reaction temperature of 35° C., at 7.5 mL ethanol to gram of compound (10) and varying the equivalents of the base to compound (10) from 2.2:1 to 2.6:1. The conversion of compound (10), the isolated yield of compound (11), and the amount of the following impurity were evaluated. Impurity (proposed based on LC-MS):

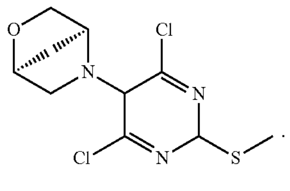 [SMILES: CSC1N=C(Cl)C(N2C[C@@H]3C[C@H]2CO3)C(Cl)=N1]

The results are summarized in Table 2.

TABLE 2

| | | 4 hours | | | 5 hours | | |
|---|---|---|---|---|---|---|---|
| Trial | Eq. $Et_3N$ | (11) (%) | (10) (%) | Imp. (%) | (11) (%) | (10) (%) | Imp. (%) |
| 1 | 2.2 | 97.4 | 1.15 | 0.82 | — | — | — |
| 2 | 2.3 | 98.9 | 0.60 | 0.42 | 95.5 | 0.40 | 1.1 |
| 3 | 2.4 | 99.3 | 0.44 | 0.25 | 99.6 | 0.25 | 0.18 |
| 4 | 2.6 | 99.3 | 0.16 | 0.35 | — | — | — |

Conversion of compound (10) increased equivalents of base, and the impurity decreased going from 2.20 to 2.40 equivalents but increased again when 2.60 equivalents were applied.

Calorimetric studies were done and showed a total adiabatic temperature rise of 68° C. when the addition of triethylamine was performed at 22° C. over 2 hours in 7.5 volumes of ethanol. In case of a complete adiabatic event, a temperature of 90° C. would be reached that was equal to the safety temperature determined for this reaction. When the base was added at 35° C. under more dilute conditions (10 volumes ethanol), the total adiabatic temperature rise was reduced to 46° C., leading to a maximum temperature of the synthetic reaction (MTSR) of 81° C., lower than the safety temperature. The diluted safer version was thus applied on scale. Desired conversion was typically reached 3 hours post addition of base. During addition of $Et_3N$, the product began to precipitate. At full conversion, the suspension was cooled to 22° C., water was added to enhance the precipitation and dissolve the salts and compound (11) was isolated by filtration. Residual compound (10) and the impurity were typically always observed below 0.05% in the isolated product. This process was successfully implemented on a scale of 50 kg of compound (10) affording pyrimidine compound (11) in 90% yield and 99.9% w/w assay.

Example 9

Prior art processes for preparing compound (16) by oxidation of compound (11) were done with 5 mol % sodium tungstate dihydrate in MeOH/water, charging 2.5 equivalents $H_2O_2$, and aging for 30 hours at 20-30° C. In process control testing showed typically 1-2% of compound (11) and intermediate sulfoxide (Scheme 3) remaining. After addition of another 0.5 equivalents $H_2O_2$ and further 48 hours aging at 55-62° C., the system was quenched with aqueous $Na_2S_2O_3$ and 90% of sulfone compound (16) was isolated by filtration. The prior art process could result in $H_2O_2$ accumulation with a concomitant risk of uncontrolled $H_2O_2$ decomposition.

Example 9 evaluated development of a safe process that minimizes the risk of $H_2O_2$ accumulation while reducing the reaction time. Room temperature was not sufficient to reach a complete conversion, so reaction testing was done at 45° C. using 3 equivalents $H_2O_2$. A similar conversion profile was observed after 20 hours with 5 mol % $Na_2WO_4 \cdot 2H_2O$ catalyst as with 1 mol % $Na_2WO_4 \cdot 2H_2O$ catalyst. Further increasing the reaction temperature to 55° C. with 1 mol % catalyst allowed more than 99.5% conversion after 4-6 hours.

The reaction scheme was as follows:

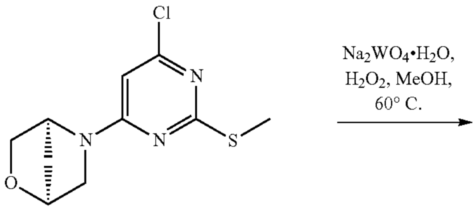

(11)

-continued

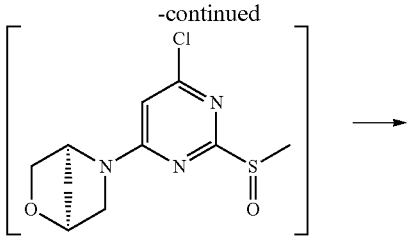

Sulfoxide intermediate

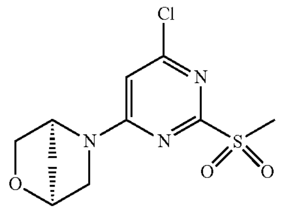

(16)

Calorimetry measurements of 4 reaction procedures were performed. The results are summarized in Table 2. The reaction conditions were 1 mol % $Na_2WO_4 \cdot 2H_2O$ and MeOH/water 2:1 solvent. Equivalents of $H_2O_2$ and $H_2O_2$ dosing regimen are shown in Table 2. In Table 2: Td is the temperature during dosing; Tr is the temperature of the reaction; ΔrH is the enthalpy of the reaction; Acc is the $H_2O_2$ accumulation; ΔadiaTmax us the total adiabatic temperature rise; and MTSR is the maximum temperature of the synthetic reaction calculated as Tr+Acc x ΔadiaTmax. Residual sulfoxide intermediate was measured at a total reaction time of 19-22 hours and is reported in area % HPLC.

TABLE 2

| Trial | 1 | 2 | 3 | 4 |
|---|---|---|---|---|
| Td (° C.) | 23 | 55 | 60 | 60 |
| Tr (° C.) | 55 | 55 | 60 | 60 |
| $H_2O_2$ (eq.) | 3.0 | 3.0 | 3.0 | 2.3 |
| $H_2O_2$ Dosing time (min) | 30 | 120 | 160 + 80 | 240 |
| ArH (kj/mol compound (11) | -460 | -505 | -446 | -455 |
| Acc (%) | 97 | 68 | 15 | 13 |
| AadiaTmax (° C.) | 38 | — | — | 37 |
| MSTR (° C.) | 93 | — | — | 65 |
| Residual sulfoxide intermediate (%) | 0.36 | 0.45 | 0.29 | 0.3 |

The batch process with addition of 3 equivalents $H_2O_2$ at 23° C. within 30 minutes followed by heating to 55° C. and aging for 20 hours at 55° C. was clearly not a safe process with 97% accumulation of $H_2O_2$ and a MTSR of 93° C. (trial 1). Changing from a full batch to a semi-batch process by dosing 3 equivalents $H_2O_2$ at 55° C. for 2 hours followed by 2 hours aging gave residual sulfoxide intermediate of 0.57%, which reduced only to 0.45% within the next 17 hours. The $H_2O_2$ accumulation was still 68% (trial 2). Increasing the reaction temperature to 60° C., 2 equivalents $H_2O_2$ were first dosed within 160 minutes leading to complete conversion of compound (11) and 25% remaining residual sulfoxide intermediate. After 30 minutes, a third equivalent of $H_2O_2$ was added within 80 minutes bringing residual sulfoxide intermediate to 0.29%. This level did not change in the next 15 hours. At this temperature, $H_2O_2$ accumulation was reduced to 15% (trial 3). Reducing the total amount of $H_2O_2$ to 2.3 equivalents dosed within 4 hours led to 2.2% residual sulfoxide intermediate at the end of addition and a level of 0.30% after 16 hours aging. The maximum accumulation for this process reached only 13% and MTSR was 65° C. (trial 4), about 10° C. below the boiling point of the solvent mixture, making this procedure a safe process for the standpoint of $H_2O_2$ accumulation.

Example 10

Suzuki Coupling Reaction

Prior art processes teach preparing compound (24) by the Suzuki coupling of boronate (23) with compound (16) in the presence of 1 mol % $PdCl_2(PCy_3)_2$ and 3 equivalents $K_2CO_3$ in THF/water at 65° C. to afford pyrido-pyrimidine (24), which precipitated from the reaction mixture in the organic phase and was isolated by simple filtration after removal of the aqueous phase. In order to obtain an acceptable yield (>80%) from this process, the organic layer had to be dried azeotropically prior to filtration which required large solvent volumes. Isolation and purification was a combination of aqueous work-up and treatment with silica gel and charcoal followed by crystallization. Preliminary assays showed that the catalyst amount could be reduced to 0.5 mol % still providing a complete conversion within 5 hours, but reducing the catalyst amount further to 0.25 mol % resulted in an incomplete conversion even after 20 hours. The reaction was further optimized with 0.5 mol % $PdCl_2(PCy_3)_2$. Changing the solvent to 2-MeTHF led to a slower conversion, about 4% compound (16) remaining after 5 hours at 65° C., the phase separation was not improved, and the filtration for isolation was very slow. In toluene or isopropyl acetate solvent, no product was formed. Thus, further development was done with THF.

Compound (23) produced by Example 1, steps 4 and 5 provided for incomplete conversion of compound 16 after 5 hours at 65° C., with the reaction stalling at about 10% unconverted compound (16). Increasing the amount of catalyst back to 1 mol % allowed an increase in conversion to about 97% after 20 hours, with the reaction being slower than with the previous batch. Without being bound to any particular theory, it was speculated that some residual catalyst in compound (23) had led to a more effective catalyst in the Suzuki coupling. Therefore, the boronate formation in the Suzuki coupling reaction was tested on purified boronate compound (23) with 0.5 mol % $PdCl_2(dppf)$ catalyst to provide the desired conversion after 3 hours at 60-65° C. Reducing the amount of catalyst to 0.1 mol % gave an incomplete conversion even after 20 hours. For the isolation of compound (24), it was observed with the reactions run with $PdCl_2(PCy_3)_2$, that the addition of n-heptane after separation of the phases, skipping the azeotropic distillation, and aging at 10° C. led to 80% yield of compound (24). The same procedure applying the azeotropic distillation before adding n-heptane afforded 83% yield of compound (24). Further just adding the n-heptane at 60° C. without separating the phases and cooling to room temperature gave 85% compound (24). The last process was repeated with reactions run with $PdCl_2(dppf)$ and observed that the aging time had a significant impact on the yield. Aging for only 1 hour afforded only 82% compound (24), whereas 15 hours aging gave 87% compound (24). The Pd level observed in the product was around 100-150 ppm. As the material was for clinical studies, the Pd level in active pharmaceutical ingredient was limited to a maximum of 10 ppm. A treatment with 0.1 equivalent N-acetyl-cysteine at 60° C. for 30 minutes before adding n-heptane reduced the Pd level to below 10 ppm. The hydrolyzed product impurity, which was observed at levels up to 0.52% with $PdCl_2(PCy_3)_2$ was always below 0.08% in the reactions run with $PdCl_2(dppf)$. The boronate dimer impurity was observed <50 ppm in isolated compound (24). The sulfoxide impurity (see Example 9), present at 0.2% in compound (16), reacted much slower than compound (16) under the conditions of the Suzuki reaction. The Suzuki product of the sulfoxide impurity was observed at level <0.1% in compound (24), and sulfoxide impurity content was below the reporting limit. At 40 kg scale, the crystallization did not happen spontaneously, and seeding after N-acetyl cysteine addition was implemented. The pyrido-pyrimidine compound (24) was isolated in 84% yield, 99.3%-w/w assay, with Pd levels of 5 ppm or lower.

The impurities are as follows:

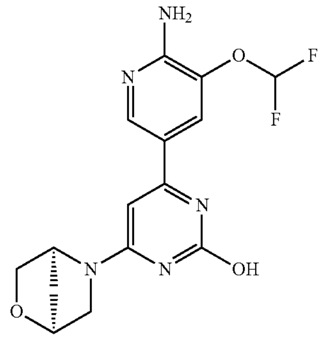

Hydrolyzed Product Impurity

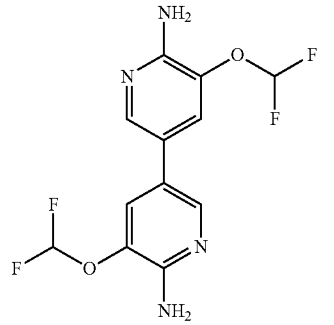

Boronate Dimer Impurity

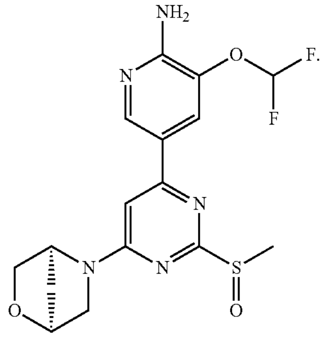

Sulfoxide Impurity

Example 11

Nucleophilic Aromatic Substitution (SNAr)

Prior art processes performed the substitution of pyrido-pyrimidine compound (24) with the difluoropyrrolidine compound (28) in the presence of $K_3PO_4$ in NMP at 130° C. and the product compound (1) was isolated by precipitation by addition of a large amount of water. This reaction was heterogeneous, and the particle size of $K_3PO_4$ had an impact on the impurity profile of crude compound (1). NMP has been identified as a SVHC. Experiments were done to find an alternative solvent and a combination of base and solvent that would generate a homogeneous reaction mixture. A base screening in NMP was first conducted: pyridine and triethylamine led to only moderate conversion after 17 hours and high amount of hydrolyzed product impurity. Tetramethylguanidine (TMG) and 1,8-diazabicyclo[5.4.0]undec-7-ene (DBU) conferred a complete conversion within 20 hours. The reaction mixture containing TMG was a dark brown turbid suspension, and after addition of water, only 19% product of moderate purity was isolated. The reaction mixture with DBU was a light beige suspension and addition of water led to 42% of a cleaner material. Thus, DBU was selected as base for further optimization according to the following scheme:

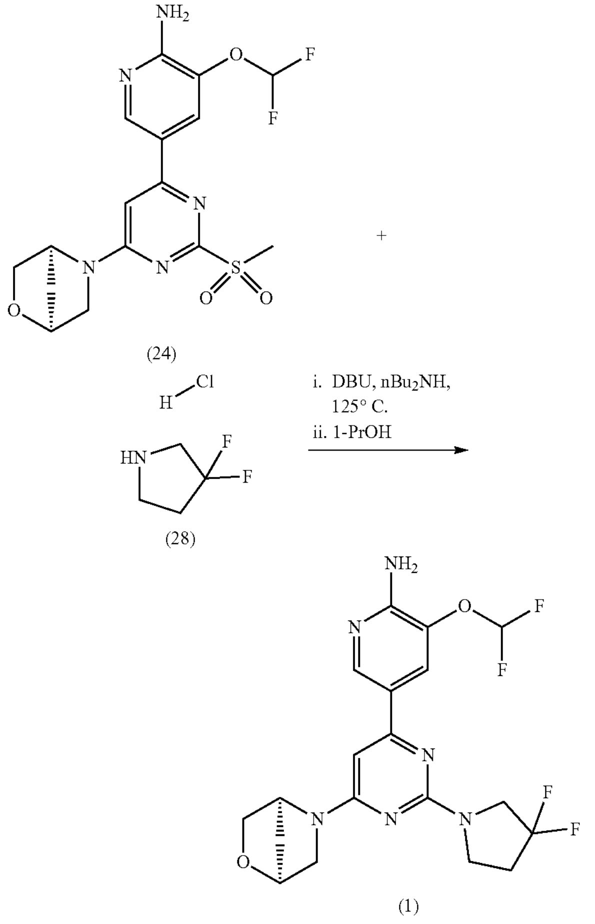

(24) (28) (1)

A solvent screen with DBU was performed and the results are reported in Table 3. Trials 1 to 10 used 2.5 eq. of compound (28), 5.0 eq. DBU in 4 mL solvent/g of compound (24). Trial 9 was done in a closed vessel. Trial 11 used 2.5 eq. of compound (28), 2.4 eq. DBU in 4 mL solvent/g of compound (24). The remainder of the trials used 2.1 eq. of compound (28), 2.0 eq. DBU in 6 mL solvent/g of compound (24). Acetonitrile provided <50% conversion after 18 hours (trial 1). Without being bound to any particular theory, it is believed that the low boiling point of acetonitrile led to the low conversion. DMSO at 125° C. gave >90% conversion in 8.5 hours, but safety concerns regarding reaction of DMSO and base at elevated temperature limited the further development at temperature below 100° C. and at this temperature the conversion was only 90% after 24 hours (trials 2 and 3). In benzonitrile, cyclohexanone, 1,3-dichlorobenzene and xylene at 125° C. the conversion was below 90% after 17 hours (trials 4 to 7). Toluene and anisole at 120° C. (trials 9 and 10) and mesitylene (trial 11) at 125° C. led to more than 95% conversion after 20, 23 and 22 hours respectively.

TABLE 3

| Trial | Solvent | Reaction Temp (° C.) | Time (h) | Residual compound (24) |
|---|---|---|---|---|
| 1 | Acetonitrile | 82 (reflux) | 18 | 54 |
| 2 | DMSO | 135 | 8.5 | 4 |
| 3 | DMSO | 100 | 24 | 10 |
| 4 | Benzonitrile | 125 | 15 | 15 |
| 5 | Cyclohexanone | 125 | 17 | 27 |
| 6 | 1,3-Dichlorobenzene | 125 | 17 | 13 |
| 7 | Xylene (technical) | 125 | 18 | 10 |
| 8 | Toluene | 110 | 20 | 5.6 |
| 9 | Toluene | 120 | 20 | 2.1 |
| 10 | Anisole | 120 | 23 | 2.2 |
| 11 | Mesitylene | 125 | 22 | 1.1 |
| 12a | Tributylamine | 110 | 23 | 12.5 |
| 12b | Tributylamine | 110 | 38 | 6.5 |
| 13a | Dibutylamine | 110 | 23 | 5.4 |
| 13b | Dibutylamine | 110 | 38 | 1.1 |
| 14 | Dibutylamine | 125 | 23 | <1 |

In toluene, anisole, and mesitylene, the reaction mixture was bi-phasic with a lower product phase and an upper solvent phase. Isolation of the product from the reaction in toluene was performed by adding water after cooling to 50° C. and further cooling to room temperature. The suspension formed was very dense and difficult to stir and some experiments to identify a more appropriate crystallization solvent were conducted. The phases of a reaction mixture in toluene were separated and the product phase was diluted with acetonitrile, isopropanol and acetone at 80° C. followed by treatment with water and cooling. Acetonitrile and isopropanol gave rise to suspensions that formed clumps upon cooling and acetone afforded a sticky precipitate. Addition of only isopropanol or n-propanol to the product phase led to nice suspensions. n-Propanol afforded a slightly higher yield and purity, which were also obtained when n-propanol was simply added to the biphasic mixture and n-propanol was selected for further optimization of the reaction.

Because higher temperatures provide for a faster conversion, mesitylene was selected over toluene for further optimization and experiments with addition of some bases additives are summarized in Table 4. In trials 1 to 4, 2.5 eq. compound (28) in 4V mesitylene at 125° C. for 19-22 h, additive used in equimolar amount versus DBU, addition of n-PrOH and cooling to room temperature, age for overnight. Trial 5 was similarly done except 2.0 eq. compound (28) as used. Running the reaction with 2.5 equivalents of compound (28) and 2.4 equivalents DBU yielded, after precipitation with n-propanol, 55% of crude compound (1) (trial 1). Adding equimolar (based on DBU) amount of DABCO (trial 2) led to complete conversion, however a lower yield was isolated. 2,6-Lutidine (trial 3) had a slightly positive effect on the yield. $iPr_2EtN$ (trial 4) induced both complete conversion and a significantly better yield of 80%. Reducing the amount of bases to 1.9 eq. and of compound (28) to 2.0 eq. resulted in a conversion >98% and an isolated yield of 75% (trial 5). Following this observation, a liquid amine base was tried as solvent.

TABLE 4

| Trial | DBU (eq.) | Additive Base | Conversion (%) | Yield (%) | Purity (%) |
|---|---|---|---|---|---|
| 1 | 2.4 | — | 98.9 | 55 | 97.9 |
| 2 | 2.4 | DABCO | >99.9 | 47 | 98.2 |
| 3 | 2.4 | 2,6-lutidine | 98.9 | 64 | 98.5 |
| 4 | 2.4 | $iPr_2EtN$ | >99.9 | 80 | 99.0 |
| 5 | 1.9 | $iPr_2EtN$ | 98.3 | 75 | 98.8 |

Tri-n-butylamine and di-n-butylamine were tested at 110° C. (Table 3, trials 12 and 13). The conversion was faster in di-n-butylamine affording close to 95% conversion in 23 hours whereas tri-n-butylamine showed less than 90% conversion. Increasing the temperature to 125° C. in di-n-butylamine (Table 3, trial 14) provided a complete conversion in 15 hours and 81.5% of compound (1) was isolated by crystallization after addition of n-propanol in close to 98.3% area purity. The crystals were off-white offering the perspective to avoid the charcoal filtration before the final crystallization. Reducing the amount of compound (28) and DBU to 1.5 equivalents the desired conversion was achieved at 125° C. after 20 hours and a comparable yield was obtained. The starting materials were mixed in only 4 volumes di-n-butylamine. The reaction mixture was a suspension at lower temperatures but turned into a clear emulsion at reaction temperature. Crystallization was induced by slow addition of n-propanol at 95° C. and further cooling to 20° C. Further cooling to 0° C. did not improve the yield. The crystallization purged efficiently the residual starting material compound (24). Levels of up to 1.75% were purged below 0.20%. Several impurities were formed in this step and are depicted below. The di-n-butyl analog impurity formed in levels up to 6% was purged below 0.10%. n-Butyl and n-pentyl analog impurities arising from impurities present in di-n-butylamine were formed in low levels and purged below 0.20% in the isolated product. The monofluoro and des-fluoro analog impurities were downstream products of impurities present in 3,3-difluoropyrrolidine, the des-fluoro analog impurity being also potentially formed in the reaction, and were always observed below reporting limit in crude compound (1). The substitution product impurity of compound (24) with 1-(3-aminopropyl)azepan-2-one, a hydrolysis product of DBU (likely present as impurity in DBU), and the dimer impurity formed as a side-product of the reaction were also observed. Both were present below 0.1% in crude compound (1). On 50 kg scale, the optimized process applying 1.5 equivalents of each of compound (28) and DBU in di-n-butylamine at 125 TC for 20 hours followed by addition of n-propanol to induce crystallization led to 75% compound (1) in 99.5%-w/w assay with all impurities below 0.10%.

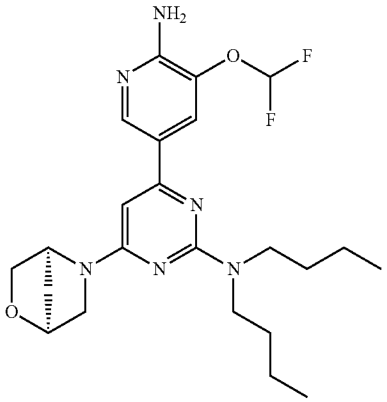

di-n-butyl analog impurity

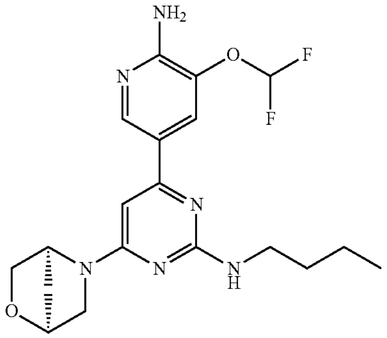

n-butyl analog impurity

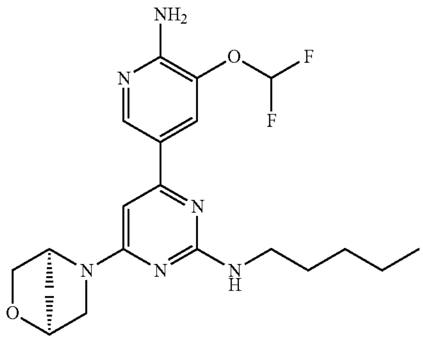

n-pentyl analog impurity

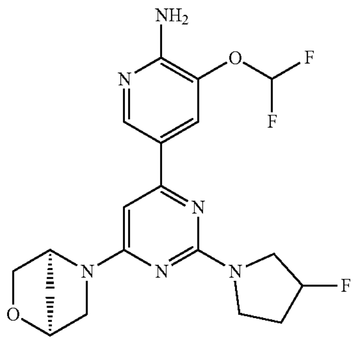

monofluoro analog impurity

-continued

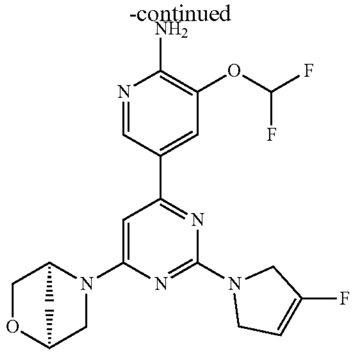

des-fluoro analog impurity

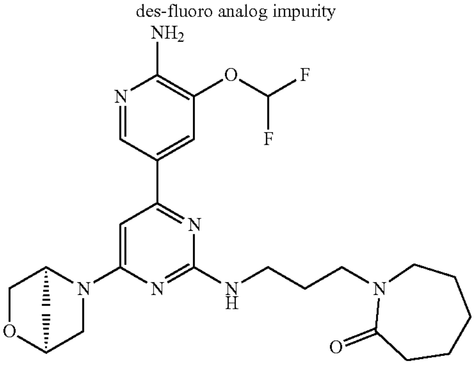

compound (24) substitution product impurity

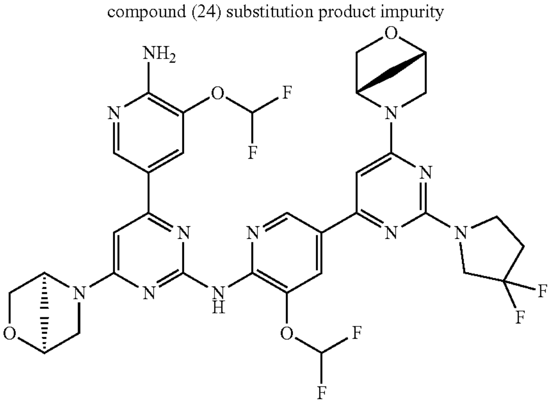

dimer impurity

Example 12: Recrystallization

Form A is the only known crystalline modification of the free base of compound (1), and the solubilities given in Table 5 below refers to this form. Moreover, a crystal structure prediction (CSP) ranked a structure equal to Form A as the thermodynamically most stable modification at ambient conditions. The risk to obtain another form was considered as very low. Nevertheless, seeding was used as a method to allow for consistent crystal growth conditions and to obtain reproducible particle size distributions at the end of the crystallization.

Prior art processes for preparing compound (1) used isopropyl acetate for final crystallization, having a yield of 84% at a relatively low concentration of 3.0%-w/w. Hence, efforts were made to identify another solvent or solvent mixture, respectively, in order to improve the productivity of the final step. It was known from previous qualitative experimental data as well as solubility prediction (numerical simulation) that the possible list is reduced since the solubility of GDC-0134 in alcohols is too low. From a process design perspective, a simple cooling crystallization is preferred over other designs like antisolvent or evaporative crystallization especially because of easier process control. Hence, a large ratio in solubility between the two temperature levels is desired. Mainly esters but also acetonitrile, methyl isobutyl ketone (MIBK), and 2-MeTHF were on the shortlist for precise solubility determination. The solubility of compound (1) in these solvents is Table 5 for 0° C. and the respective maximum process temperatures. The calculated maximum solids concentration and the theoretical yield are listed in Table 6. For MeOAc, EtOAc, n-PrOAc and 2-MeTHF, the solubility at 0° C. is rather high and they do not represent a good alternative compared to iPrOAc from the EiH process with respect to yield and concentration. While the solubility in acetonitrile is very low even for high temperatures, mixtures of 2-MeTHF and acetonitrile show a synergistic effect at least for a 1:1 mixture. The solubility at 70° C. is the highest among the investigated systems, and the theoretical yield is close to 90%. Due to concerns with regard to the efficient removal of acetonitrile to acceptable levels after drying, 2-MeTHF/acetonitrile-mixtures were not further investigated, though. MIBK offered the highest theoretical yield plus a significant increase in concentration compared to iPrOAc and it was selected for a more detailed investigation

TABLE 5

Solubility of compound (1) in solvents at 0° C. and the respective maximum process temperature

| Solvent | Solubility at 0° C. (w/w %) | Max Temp (° C.) | Solubility at max temp (w/w %) |
|---|---|---|---|
| 2-MeTHF:MeCN (3:1) | 1.7 | 70 | 2.2 |
| 2-MeTHF:MeCN (1:1) | 0.8 | 70 | 7.3 |
| 2-MeTHF | 1.6 | 70 | 5.2 |
| MIBK | 0.4 | 80 | 5.2 |
| i-propyl acetate | 0.4 | 80 | 4.2 |
| n-propyl acetate | 0.8 | 80 | 4.3 |
| Ethylacetate | 0.9 | 70 | 4.8 |
| Methylacetate | 1.3 | 50 | 4.9 |
| Acetonitrile | 0.5 | 70 | 1.4 |

TABLE 6

Theoretical outcome for a cooling crystallization based on the data reported in Table 5

| Solvent | Theoretical max compound (1) solids concentration (% w/w) | Theoretical yield (%) |
|---|---|---|
| 2-MeTHF:MeCN (3:1) | 0.6 | 27.3 |
| 2-MeTHF:MeCN (1:1) | 6.5 | 89.0 |
| 2-MeTHF | 3.6 | 69.2 |
| MIBK | 4.8 | 92.3 |
| i-propyl acetate | 3.8 | 90.5 |
| n-propyl acetate | 3.5 | 81.4 |
| Ethylacetate | 3.9 | 81.3 |
| Methylacetate | 3.6 | 73.5 |
| Acetonitrile | 1.1 | 73.3 |

Seeded cooling crystallizations was conducted to directly compare experimental yield. Results are shown in Table 7. For a cooling rate of 12 K/h, short equilibration times at isolation temperature led to yields which were significantly below the expected yields for both isopropyl acetate (trial 1) and MIBK (trial 2). When equilibration time was extended (trials 3 and 4), the yields were much higher. The crystallization study demonstrates that the use of MIBK is superior to isopropyl acetate with respect to yield. Apart from productivity, impurity rejection was another very important aspect. For purity evaluation, crude compound (1) of poor quality (98.9 area % HPLC) was used. The cooling rate for trial 6 was 3° K/h from 80° C. to 40° C. and 6° K/h from 40° C. to 0° C. It is known that the crystallization conditions can have a considerable influence on product quality. For example, use of another solvent, rapid cooling or the exceeding of a critical yield can negatively impact purity. However, in the experiments shown in Table 7 was small. Consequently, there is no data connecting MIBK with poorer depletion of impurities.

TABLE 7

Effect of cooling rate and final equilibrium time on yield and purity

| Trial | Solvent | Cooling rate (K/h) | Time to 0° C. (h) | Yield (%) | Purity (%) |
|---|---|---|---|---|---|
| 1 | i-PrOAc | 12 | 4 | 75.6 | 99.4 |
| 2 | MIBK | 12 | 10 | 82.8 | 99.5 |
| 3 | i-PrOAc | 12 | 68 | 83.6 | 99.3 |
| 4 | MIBK | 12 | 68 | 87.8 | 99.4 |
| 5 | MIBK | 6 | 57 | 87.2 | 99.6 |
| 6 | MIBK | 3/6 | 51 | 85.8 | 99.5 |

Examples 8 to 12 are summarized in the following scheme:

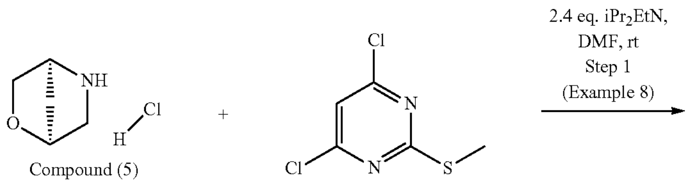

Compound (5)

Compound (10)

-continued

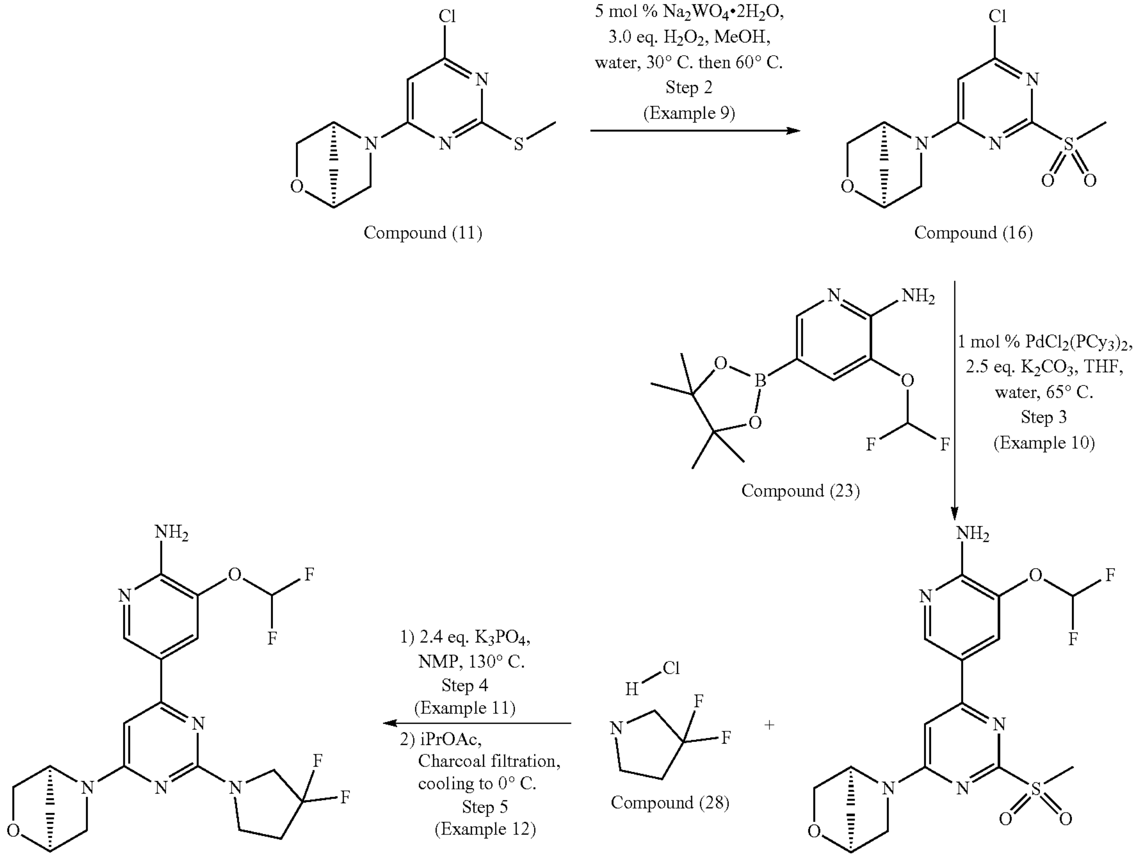

Compound (11)

Compound (16)

Compound (23)

Compound (28)

Compound (24)

Compound (1)

The greenness improvement from the prior art processes to the present disclosed and exemplified process was evaluated. The PMI of both processes were calculated and the results are shown in Table 8. The total input of material was reduced by more than 40% in the present process. The $S_NAr$ step and the final crystallization were the major contributors to that improvement as the material input was reduced by 60% and 50% respectively. Looking closer to the solvent used, both SVHC solvents DMF and NMP were removed in the present process, only water and sustainable solvents were implemented. The total amount of solvents used was reduced by ¼ and the total input of water was reduced by ⅔.

TABLE 8

| | Prior art processes (kg/kg API) | Present process (kg/kg API) | % Change |
|---|---|---|---|
| PMI | 230 | 131 | -43 |
| Solvents | 120 | 89 | -26 |
| Water | 100 | 37 | -63 |

PMI was calculated for each of steps 1 to 5 shown in the process scheme above. The results are shown in Table 9.

TABLE 9

| | Prior art processes (kg/kg API) | Present process (kg/kg API) |
|---|---|---|
| Step 1 | 36 | 22 |
| Step 2 | 44 | 22 |

TABLE 9-continued

| | Prior art processes (kg/kg API) | Present process (kg/kg API) |
|---|---|---|
| Step 3 | 45 | 26 |
| Step 4 | 44 | 16 |
| Step 5 | 58 | 26 |

The present process for the manufacturing of compound (1), as compared to prior art processes, provides for enhanced safety and greenness while delivering the compound (1) in 43.5% overall yield (steps 1 through 5) and with an excellent purity. DMF used in prior art processes in the first $S_NAr$ reaction was replaced with environmentally benign ethanol. Safety and rate of the oxidation to the sulfone was increased by dosing at higher temperature avoiding accumulation of highly reactive hydrogen peroxide and reducing the reaction time from more than 3 days to 6 hours. A more efficient catalyst for the Suzuki coupling was identified and the azeotropic distillation was obviated by adding n-heptane without separating the phases. NMP in the second prior art $S_NAr$ reaction was replaced with di-n-butylamine providing for a cleaner reaction and yielding a crude compound (1) of high purity. Finally, crystallization to pure compound (1) was performed from MIBK without prior charcoal treatment. The use of MIBK instead of isopropyl acetate allowed the final crystallization to be conducted at higher temperature. The present process has a significantly lower environmental impact than the prior art processes with a PMI reduced by more than 40%. It was utilized successfully to produce 150 kg API to support clinical studies as per Example 13 below.

Example 13

Steps 1 to 5 of Examples 8 to 12 were scaled up.

Example 13A: Synthesis of (1S,4S)-5-(6-chloro-2-methylsulfanyl-pyrimidin-4-yl)-2-oxa-5-azabicyclo [2.2.1]heptane (Compound 11)

To a solution of (1S,4S)-2-oxa-5-azabicyclo[2.2.1]heptane (compound 5) (40.6 kg, 0.30 kgmol) and 4,6-dichloro-2-methylsulfanyl-pyrimidine (compound 10) (52.0 kg, 0.27 kgmol) in ethanol (395 kg) at 31-34° C., triethylamine (65.0 kg, 0.64 kgmol) was added within 120 minutes and the addition vessel was rinsed with ethanol (9.0 kg). The resulting suspension of compound 11 was stirred at 32-34° C. for at least 3 hours. When in process control testing (IPC) indicated that the reaction was essentially complete, the suspension was cooled to 22° C. within 3 hours and water (315.0 kg) was added within 40 minutes with stirring. The suspension was further stirred at 22° C. for at least 3 hours, the precipitate was isolated by centrifugation, washed with a mixture of ethanol (28.0 kg) and water (213.0 kg) and dried under reduced pressure at 45° C. for 7 hours to afford 61.6 kg of compound 11 (90% yield, 99.9%-w/w, HPLC assay) as a white solid. $^1$H NMR (600 MHz, $CDCl_3$) δ ppm 5.72-6.28 (m, 1H), 5.21 (br s, 1H), 4.72 (br s, 1H), 3.78-3.93 (m, 2H), 3.18-3.48 (m, 2H), 2.49 (s, 3H), 1.80-2.13 (m, 2H). $^{13}$C NMR (151 MHz, $CDCl_3$) δ ppm 172.1, 160.2, 159.1, 97.0, 76.1, 73.8, 56.6, 55.2, 36.4, 14.1. HRMS calcd. for $C_{10}H_{12}ClN_3OS$ 257.0395; found: 297.0395. The $^1$H NMR, $^{13}$C NMR and $^{19}$F NMR spectra were measured on Bruker 600 MHz NMR spectrometers at 600, 150 and 565 MHz, respectively. The relative chemical shifts are reported in ppm relative to TMS.

Example 13B: Synthesis of (1S,4S)-5-(6-chloro-2-methylsulfonyl-pyrimidin-4-yl)-2-oxa-5-azabicyclo [2.2.1]heptane (Compound 16)

To a suspension of compound 11 (47.3 kg, 0.18 kgmol) and $Na_2WO_4 \cdot 2H_2O$ (0.61 kg, 1.85 mol) in methanol (368 kg) and water (241 kg) in a feed tank at 60° C., $H_2O_2$ 35% (40.8 kg, 0.42 mol) was added within 4 hours. The 02 level within the reactor was controlled with a limit of no more than 5%. The feed tank was rinsed with water (10.6 kg) into the reaction vessel and the suspension was stirred at 60° C. for 3 hours. At IPC compliance, the reaction mixture was cooled to 22° C. within 75 minutes. A solution of 38% aqueous $NaHSO_3$ (47.8 kg) was added within 20 minutes, the feed tank was rinsed with water (5.4 kg) into the vessel. The suspension was stirred at 22° C. for 3 hours. The compound 16 precipitate was collected by centrifugation, water (168 kg) was used to ensure complete transfer and the filter cake was washed with water (483 kg). Compound 16 was dried under reduced pressure (45-7 mbar) at 45° C. for 5 hours to furnish 47.6 kg of compound 16 (89.3% yield, 99.6% w/w HPLC assay) as a white solid. $^1$H NMR (600 MHz, $CDCl_3$), major rotamer: 8 ppm 6.31 (s, 1H), 5.33 (s, 1H), 4.79 (s, 1H), 3.80-4.01 (m, 2H), 3.37-3.45 (m, 2H), 3.28 (s, 3H), 1.78-2.07 (m, 2H). Minor rotamer: 8 ppm 6.51 (s, 1H), 4.75 (br s, 1H), 4.51 (br s, 1H), 3.80-4.01 (m, 2H), 3.37-3.45 (m, 2H), 3.28 (s, 3H), 1.98-2.16 (m, 2H). $^{13}$C NMR (151 MHz, $CDCl_3$) δ ppm 165.7, 160.8, 160.5, 159.9, 104.0, 103.5, 75.9, 75.5, 73.7, 72.9, 57.7, 57.6, 56.6, 55.6, 38.8, 38.7, 37.1, 36.5. HRMS calcd. for $C_{10}H_{12}ClN_3O_3S$ 289.0288; found: 289.0292.

Example 13C: Synthesis of 3-(difluoromethoxy)-5-[2-methylsulfonyl-6-[(1S,4S)-2-oxa-5-azabicyclo [2.2.1]heptan-5-yl]pyrimidin-4-yl]pyridin-2-amine (Compound 24)

To a suspension of compound 16 (47.5 kg, 0.164 kgmol), 3-(difluoromethoxy)-5-(4,4,5,5-tetramethyl-1,3,2-dioxaborolan-2-yl)pyridin-2-amine (compound 23) (54.0 kg, 0.189 kgmol) and $K_2CO_3$ (68.0 kg, 0.492 kgmol) in THF (510 kg) and water (165.0 kg) in a feed tank was added at 20° C., $PdCl_2$(dppf) (0.60 kg, 0.82 mol), and the reaction mixture was heated to 63° C. within 1 hour and stirred at this temperature for 3 hours. At compliant IPC, the reaction mixture was cooled to 58° C. and a solution of N-acetyl-cysteine (2.8 kg, 0.017 kgmol) in water (20.2 kg) was added within 15 minutes. The feed tank was rinsed into the vessel with water (9.6 kg) and stirring was pursued for 2 hours. The reaction mixture was seeded with compound 24 (160 g) and stirring was continued for 75 minutes. n-Heptane (97.0 kg) was added with stirring within 40 minutes, the suspension was cooled to 22° C. within 3 hours and stirred at 22° C. for 6 hours to form a precipitate of compound 24. The precipitate was isolated by centrifugation, washed with a mixture of THF (189.2 kg) and water (191.2 kg) and dried under reduced pressure at 45° C. for 9.5 hours to furnish 57.0 kg of compound 24 (84% yield, 99.3%-w/w HPLC assay) as a white solid. $^1$H NMR (600 MHz, $CDCl_3$) δ ppm 8.56 (d, J=2.0 Hz, 1H), 7.96 (s, 1H), 6.51 (br s, 1H), 6.46-6.74 (m, 1H), 5.38 (br s, 1H), 5.08 (s, 2H), 4.80 (br s, 1H), 3.88-3.94 (m, 2H), 3.41-3.61 (m, 2H), 3.34 (s, 3H), 2.06 (br d, J=8.7 Hz, 1H), 1.94 (br d, J=9.4 Hz, 1H). $^{13}$C NMR (151 MHz, $CDCl_3$) δ ppm 165.7, 160.9, 160.7, 153.3, 144.0, 133.1, 124.8, 122.9, 116.0, 98.0, 76.1, 73.9, 57.1, 55.6, 38.7, 36.5. $^{19}$F NMR (565 MHz, $CDCl_3$) δ ppm −80.61 (d, J=73.0 Hz, 2 F) HRMS calcd. for $C_{16}H_{17}F_2N_5O_4S$ 413.0969; found: 413.0975.

Example 13D: Synthesis of Crude Compound 1

To a suspension of compound 24 (64.0 kg, 0.155 kgmol) and 3,3-difluoropyrrolidine hydrochloride salt (compound 28) (33.2 kg, 0.231 kgmol) in di-n-butylamine (197.4 kg) at 25° C., DBU (35.5 kg, 0.233 kgmol) was added within 20 minutes (exothermic). A formed suspension was heated to 125° C. within 10 hours and aged at this temperature for 20 hours. At IPC compliance, n-propanol (205.0 kg) was added within 35 minutes keeping the internal temperature >90° C. to form a solution. The solution was heated to 103° C. and stirred for 15 minutes, then cooled to 20° C. within 7 hours. After an additional 30 minutes stirring at 20° C., the solids were isolated by centrifugation, washed with n-propanol (114 kg) and dried under reduced pressure at 45° C. for 6 hours to furnish 51.9 kg of compound 1 (76% yield, 99.5% w/w HPLC assay) as a yellow-white solid. $^1$H NMR (600 MHz, $CDCl_3$) δ ppm 8.52 (d, J=1.8 Hz, 1H), 7.96 (s, 1H), 6.55 (7, J=73.3 Hz, 1H), 5.98 (br s, 1H), 4.96 (s, 3H), 4.71 (s, 1H), 3.96 (br t, J=13.3 Hz, 2H), 3.88 (s, 2H), 3.84 (br t, J=7.3 Hz, 2H), 3.50 (br d, J=9.1 Hz, 2H), 2.43 (tt, J=13.8, 7.1 Hz, 2H), 1.87-2.07 (m, 2H). $^{13}$C NMR (151 MHz, $CDCl_3$) δ ppm 161.6, 160.3, 160.1, 152.4, 143.5, 133.2, 128.1, 125.6, 124.8, 116.2, 88.2, 76.4, 73.7, 56.3, 55.4, 53.5, 43.8, 36.4, 34.2. $^{19}$F NMR (565 MHz, $CDCl_3$) δ ppm −80.19

(d, J=73.0 Hz, 2 F), −100.65 (quin, J=13.2 Hz, 2 F) HRMS calcd. for $C_{19}H_{20}F_4N_6O_2$ 440.1584; found: 440.1588.

Example 13E: Compound 1 Purification

Compound 1 crude (42.9 kg, 97.4 kgmol) was charged together with MIBK (610.0 kg) to a reactor. The reactor contents were heated to 90° C. upon which a solution was formed. The solution was polish-filtered and the filter was flushed with MIBK (120.4 kg). This portion of solvent was then substantially removed by vacuum distillation. The solution was cooled to 75° C. to generate supersaturation and subsequently a seed suspension was added (0.17 kg of compound 1 Form A in 4.2 kg MIBK). The suspension was aged for 1 hour at 75° C., then cooled to −10° C. within 7 hours, followed by aging for 6 hours. Compound 1 wet cake was isolated by centrifugation. The wet cake was washed with MIBK (109.8 kg) in a first step and with ethanol (54.0 kg) in a second step. The wet compound 1 product was dried at full vacuum for two hours at 45° C. and further four hours at 60° C. until the endpoint in residual solvents was reached. The process delivered 36.8 kg of purified compound 1 (85% yield, 99.9%-w/w HPLC assay) as an almost white solid.

Example 14: Crystallinity and Thermoanalytic Evaluation

In Example 14, X-ray powder diffraction ("XRPD"), a sample of compound 1 was prepared in an open quartz glass capillary with a diameter of 0.9 mm (and was not further processed, such as by grinding). A Stoe high-low temperature attachment (working range −50 to 300) with a NiCr/Ni thermocouple for temperature measurement controlled the respective temperature conditions. The measurements were carried out with a rotating capillary and the following parameters. STOE STADI diffractometer; MYTHEN 1K detector; CuKα, 1.5406 Å radiation; Ge monochromator; 40 kV, 40 mA; moving scan; 1800 seconds per step; 2θ=3-42 degrees; 5° C./min ramp rate; and 5° C. temperature step.

Compound 1 was prepared from crude compound 1 according to the following procedure. Crude compound 1 (46 kg) was dissolved in 1080 kg of isopropyl acetate at 88.6° C. After cooling to 71° C., the solution was passed through a pre-washed and pre-heated charcoal filter. The charcoal filter was rinsed with 400 kg of hot isopropyl acetate. Under reduced pressure, the volume of the combined filtrates was concentrated to a total of 760 to 780 L. The resulting suspension was heated to 88° C. Isopropyl acetate was then added in portions (85 kg in total) to achieve complete dissolution at 88° C. The solution was cooled to 69° C. leading to a suspension which was then cooled to 0° C. within 190 minutes, and stirred at this temperature for 900 minutes. The product was isolated by filtration and rinsed with portions of cold isopropyl acetate (400 kg in total). After drying at 465° C./10 mbar for about 40 hours, 38.5 kg (approx. 84% of theoretical yield) of crystallized compound 1 was obtained.

Crystalline compound 1 was evaluated. Crystallization study procedures were done based on the solubility of compound 1 in the solvent under evaluation as follows. For a solubility of greater than 50 mg/mL at 22° C., crystallization was evaluated for each of: evaporative crystallization at 22° C.; anti-solvent (n-heptane) addition at 22° C.; and cooling crystallization from 22° C. to 0° C., or to −20° C., over 8 hours. For a solubility of less than 50 mg/mL at 22° C. but greater than 50 mg/mL at 65° C., crystallization was evaluated for each of: evaporative crystallization at 65° C.; anti-solvent (n-heptane) addition at 65° C.; and cooling crystallization from 65° C. to from 22° C., or to −20° C., over 8 hours. For a solubility of less than 50 mg/mL at 22° C. and at 65° C., crystallization was evaluated for each of: slurry equilibration at 22° C. for greater than 14 days; and slurry equilibration at 65° C. for greater than 14 days.

The results are presented below in Table 10 where: * refers to compound 1 prepared as described above; and ** refers to compound 1 prepared as described above and further incubated at 100% relative humidity at 22° C. for 17 days.

TABLE 10

| Solvent | Solubility at 22° C. | Solubility at 65° C. | Crystalline Form |
|---|---|---|---|
| Methanol | <50 mg/ml | <50 mg/mL | Form A |
| 5% water in methanol | <50 mg/mL | <50 mg/mL | Form A |
| 15% water in methanol | <50 mg/ml | <50 mg/ml | Form A |
| 50% water in methanol | <50 mg/mL | <50 mg/mL | Form A |
| Ethanol | <50 mg/mL | <50 mg/mL | Form A |
| 5% water in ethanol | <50 mg/mL | <50 mg/mL | Form A |
| 15% water in ethanol | <50 mg/mL | <50 mg/ml | Form A |
| 50% water in ethanol | <50 mg/mL | <50 mg/mL | Form A |
| Propanol | <50 mg/mL | <50 mg/mL | Form A |
| 5% water in propanol | <50 mg/mL | <50 mg/mL | Form A |
| 15% water in propanol | <50 mg/mL | <50 mg/mL | Form A |
| 50% water in propanol | <50 mg/mL | <50 mg/mL | Form A |
| Isopropanol | <50 mg/mL | <50 mg/mL | Form A |
| 5% water in isopropanol | <50 mg/mL | <50 mg/mL | Form A |
| 15% water in isopropanol | <50 mg/mL | <50 mg/mL | Form A |
| 50% water in isopropanol | <50 mg/mL | <50 mg/mL | Form A |
| Butanol | <50 mg/mL | <50 mg/mL | Form A |
| i-Butanol | <50 mg/mL | <50 mg/mL | Form A |
| s-butanol | <50 mg/mL | <50 mg/mL | Form A |
| Water | <50 mg/mL | <50 mg/mL | Form A |
| DMF | >100 mg/mL and <200 mg/ml | — | Form A |
| DMA | >200 mg/mL | — | Form A |
| NMP | >200 mg/mL | — | Form A |
| Nitromethane | <50 mg/mL | >50 mg/mL | Form A |
| Acetone | <50 mg/mL | >50 mg/mL | Form A |
| 15% water in acetone | <50 mg/mL | >50 mg/mL | Form A |
| MEK | <50 mg/mL | <50 mg/mL | Form A |
| MIBK | <50 mg/mL | <50 mg/mL | Form A |
| Ethyl acetate | <50 mg/mL | >50 mg/mL | Form A |
| Isopropyl acetate | <50 mg/mL | <50 mg/mL | Form A |
| Acetonitrile | <50 mg/mL | >50 mg/mL | Form A |
| 20% water in acetonitrile | <50 mg/mL | >50 mg/mL | Form A |
| 50% water in acetonitrile | <50 mg/mL | <50 mg/mL | Form A |
| 80% water in acetonitrile | <50 mg/mL | <50 mg/ml | Form A |
| DMSO | >100 mg/mL and <200 mg/mL | — | Form A |
| MTBE | <50 mg/mL | <50 mg/mL | Form A |
| THF | >50 mg/mL and <100 mg/mL | — | Form A |
| 15% water in THF | >50 mg/mL and <100 mg/ml | — | Form A |
| 2-methyl THF | <50 mg/mL | >50 mg/mL | Form A |
| Dioxane | >50 mg/mL and <100 mg/mL | — | Form A |
| Toluene | <50 mg/mL | <50 mg/mL | Form A |
| n-Heptane | <50 mg/mL | <50 mg/mL | Form A |
| Dichloromethane | <50 mg/mL | >50 mg/mL | Form A |
| Chloroform | <50 mg/mL | >50 mg/mL | Form A |
| Dimethyl carbonate | <50 mg/mL | >50 mg/mL | Form A |
| Acetic acid | >100 mg/mL and <200 mg/ml | — | Form A |
| Diisopropylamine | <50 mg/ml | <50 mg/ml | Form A |
| Compound 1 * | — | — | Form A |
| Compound 1 ** | — | — | Form A |

Single crystals of compound 1, form A were prepared as follows. 98 mg of recrystallized compound 1 were suspended in 5 mL of isopropyl acetate at ambient temperature. 1 mL of the clear supernatant was transferred into a 2 mL vial. This 2 mL vial was then put into a 15 mL vial containing of 2 mL of ethanol as the anti-solvent. After closure of the 15 mL vial, the system was stored for 12 days for the vapor diffusion crystallization. Single crystals were then isolated and analyzed by single crystal X-ray diffraction, confirming Form A.

Amorphous Compound 1

Amorphous compound 1 may be prepared by rapidly cooling a melt of compound 1. 194 mg of compound 1 was melted in a glass vial by heating to from about 214° C. to about 224° C. The molten material was rapidly cooled by submerging the glass vial in liquid nitrogen to form amorphous compound 1 as confirmed by XRPD.

Amorphous compound 1 may be converted to Form A by heating to a temperature greater than 70° C., a temperature above the glass transition temperature, followed by cooling and crystallization.

Compound 1 Mechanical Stress Evaluation

Micronization

Compound 1, produced generally according to the method of Example 5, was evaluated for changes induced mechanical stress conditions, where crystallinity was evaluated by XRPD and where thermoanalytic characteristics were measured by differential scanning calorimetry ("DSC"), thermogravimetric analysis ("TGA") and dynamic vapor sorption ("DVS").

In a first evaluation, compound 1 was micronized by jet milling and evaluated by XRPD and DSC. Jet milling was determined to have no significant influence on crystallinity as determined by SRPD and only minor influence of thermoanalytic data as indicated in Table 11 below.

TABLE 11

| Compound 1 thermoanalytic data before and after jet milling | | | |
|---|---|---|---|
| Milled | $T_{onset}$ | Extrapolated Peak | Enthalpy of Fusion |
| Yes | 197.9° C. | 199.9° C. | 110.4 J/g |
| No | 197.6° C. | 198.7° C. | 107.9 J/g |

Dry Granulation

About 500 mg of compound 1 was dry grinded for about 5 minutes at ambient conditions with a mortar and pestle in order to simulate shear stresses encountered during a dry granulation. No reduction of crystallinity was found in the samples after such treatment according to XRPD analysis as shown in pattern (d) of FIG. 2 as compared to untreated compound 1 (FIG. 2 pattern(a)). Furthermore, thermoanalytic data as measured by DSC, TGA, and DVS was only marginally different from compound 1 starting material (see Table 12 below).

Tableting

Figure 2:
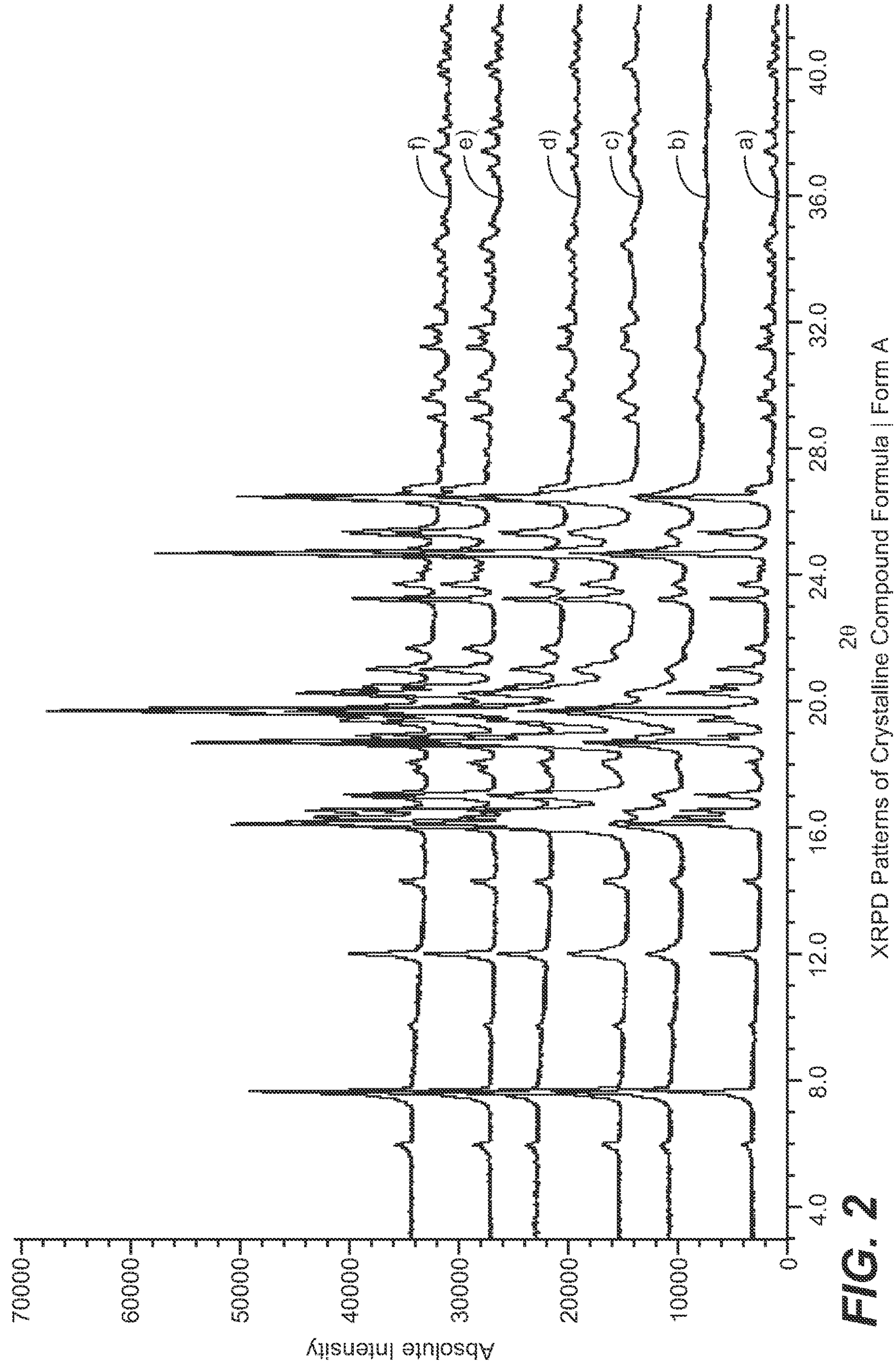
FIG. 2 shows XRPD patterns for: crystalline compound 1 Form A (pattern (a)); compound 1 tableted under 900 MPa pressure followed by tablet crushing (pattern (b)); compound 1 tableted under 900 MPa pressure followed by tablet crushing (pattern (c)); compound 1 after manual dry grinding (pattern (d)); compound 1 after manual wet grinding (pattern (e)); and compound 1 after manual wet grinding followed by drying thereof (pattern (f)).

The effect of pressure on compound 1 was performed to investigate whether phase transformation could occur during tableting. The conditions were 1.8 T/5 mm compact, 900 MPa, about 30 mg of compound 1, and a dwell time of about 6 seconds). The tablets were analyzed without further treatment and after gentle crushing of the tablets with a pestle. With and without crushing of the tablets, some reduction of crystallinity was observed by XRPD analysis. FIG. 2 pattern (b) is the XRPD pattern for crushed tablets. FIG. 2 pattern (c) is the XRPD pattern for tablets that were not crushed.

Thermoanalytic analysis shows that the total weight losses during TGA measurements were somewhat higher than of the starting material, while DVS measurements did not show a significant increase of hygroscopicity for the compacted samples (see Table 12 below).

Wet Milling

To simulate wet milling, wet manual grinding experiments were done. About 500 mg of compound 1 and about 0.5 mL water were kneaded for about 5 minutes with a mortar and pestle. About 100 mg of the wet material was analyzed by XRPD. The remainder of the material was dried overnight in an oven at 50° C. and ambient pressure. The dried material was analyzed by SRPD, DSC, TGA, and DVS.

No reduction in the crystallinity of the compounds was indicated by XRPD after manual wet milling (see FIG. 2, pattern (e)) and after hot drying of wet milled material (see FIG. 2, pattern (f)). Furthermore, thermoanalytic data as measured by DSC, TGA, and DVS was only marginally different from compound 1 starting material (see Table 12 below).

TABLE 12

| | DSC $T_{onset}$ | $\Delta H_f$ | TGA Total wt. loss | DVS $\Delta m$ (0-90% RH) |
|---|---|---|---|---|
| Compound 1 | 197.9° C. | 110.4 J/g | 0.1% m/m | <0.1% m/m |
| Dry Granulation | 197.0° C. | 109.9 J/g | 0.2% m/m | 0.1% m/m |
| Tableting (900 MPa) | 198.2° C. | 109.4 J/g | 0.3% m/m | <0.1% m/m |
| Tableting (crushing) | 197.7° C. | 108.4 J/g | 0.3% m/m | 0.1% m/m |
| Wet Granulation | 198.0° C. | 109.1 J/g | 0.2% m/m | <0.1% m/m |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It is to be understood that the invention is not limited to the particular embodiments and aspects of the disclosure described above, as variations of the particular embodiments and aspects may be made and still fall within the scope of the appended claims. All documents cited to or relied upon herein are expressly incorporated by reference.

What is claimed is:

1. A crystalline form of compound I

1

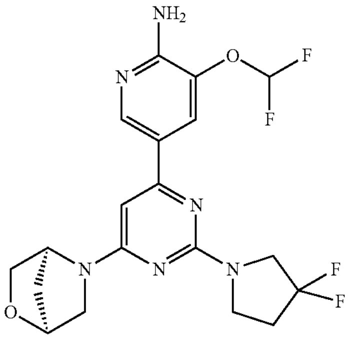

wherein the crystalline form has an X-ray powder diffraction pattern having at least two peaks at positions selected from the group consisting of 7.7±0.3 (°2θ), 12.1±0.3 (°2θ), 16.2±0.3 (°2θ), 16.4±0.3 (2θ), 16.6±0.3 (2θ), 17.1=0.3 (°2θ), 18.8±0.3 (°2θ), 19.4±0.3 (2θ), 19.8±0.3 (2θ), 20.3±0.3 (°2θ), 20.5±0.3 (°2θ), 23.3±0.3 (°2θ), 24.7±0.3 (°2θ), 25.3±0.3 (°2θ), and 26.5±0.3 (°2θ).

2. The crystalline form of claim 1, wherein said crystalline form has the X-ray powder diffraction pattern of FIG. 1.

3. A pharmaceutical composition comprising the crystalline form of claim 1 and at least one excipient.

4. A method of treating a neurodegenerative condition comprising administering an effective amount of the crystalline form of claim 1.

* * * * *